(12) United States Patent
Helmling et al.

(10) Patent No.: US 7,750,140 B2
(45) Date of Patent: Jul. 6, 2010

(54) GHRELIN BINDING NUCLEIC ACIDS

(75) Inventors: Steffen Helmling, Boston, MA (US); Dirk Eulberg, Berlin (DE); Christian Maasch, Berlin (DE); Sven Klussmann, Berlin (DE)

(73) Assignee: NOXXON Pharma AG, Berlin (DE)

( * ) Notice: Subject to any disclaimer, the term of this patent is extended or adjusted under 35 U.S.C. 154(b) by 432 days.

(21) Appl. No.: 10/522,582

(22) PCT Filed: Aug. 1, 2003

(86) PCT No.: PCT/EP03/08542

§ 371 (c)(1),
(2), (4) Date: May 24, 2006

(87) PCT Pub. No.: WO2004/013274

PCT Pub. Date: Feb. 12, 2004

(65) Prior Publication Data

US 2006/0257867 A1      Nov. 16, 2006

(30) Foreign Application Priority Data

| Aug. 1, 2002 | (EP) | 02017317 |
| Oct. 19, 2002 | (EP) | 02023637 |
| Jun. 23, 2003 | (EP) | 03014111 |

(51) Int. Cl.
C07H 21/04       (2006.01)
A61K 31/70       (2006.01)

(52) U.S. Cl. ............ 536/24.5; 536/23.1; 514/44

(58) Field of Classification Search ............... None
See application file for complete search history.

(56) References Cited

U.S. PATENT DOCUMENTS 5,847,258 A * 12/1998 Ryals et al. .......... 800/301

6,110,900 A * 8/2000 Gold et al. .......... 514/44
2003/0211967 A1 * 11/2003 Bryant et al. .......... 514/2
2006/0258607 A1 11/2006 Jarosch
2007/0031840 A1 2/2007 Klussmann

FOREIGN PATENT DOCUMENTS

| DE | 19808591 | 9/1999 |
| WO | WO 96/34879 | 11/1996 |
| WO | WO 01/87335 | 11/2001 |
| WO | WO 01/92292 | 12/2001 |

OTHER PUBLICATIONS

Nolte et al. Nature Biotechnology 1996, vol. 14, pp. 1116-1119.*
Klussmann et al. Nature Biotechnology 1996, vol. 14, pp. 1112-1115.*
Sun et al. Molecular and Cellular Biology 2003, vol. 23, pp. 7973-7981.*
Shuto, et al., Hypothalamic Growth Hormone Secretagogue Receptor Regulates Growth Hormone Secretion, Feeding, and Adiposity, The Journal of Clinical Investigation, Jun. 2002, vol. 109, No. 11, pp. 1429-1435.
Leva et al., GnRH Binding RNA and DNA Spiegelmers: A Novel Approach Toward GnRh Antagonism, Chemistry & Biology, vol. 9, pp. 351-359, Mar. 2002.
Wood, "DNA-DNA hybridization . . . BIAcore" Microchem J 47:330-337, 1993.
Helmling et al., "Inhibition of . . . Spiegelmer" PNAS 101:13174-13179, 2004.
Raghavan et al., "BIAcore . . . complexes" Structure 3:331-333, 1995.
Bednarek et al., J Med Chem 43:4370-4376, 2000.
Eaton et al., Bioorganic & Medicinal Chemistry 5(6)1087-1096, 1997.

* cited by examiner

*Primary Examiner*—Tracy Vivlemore
(74) *Attorney, Agent, or Firm*—MDIP LLC

(57) ABSTRACT

The present invention is related to an antagonist of ghrelin, wherein the antagonist is a nucleic acid, and whereby preferably the nucleic acid is binding to ghrelin.

18 Claims, 61 Drawing Sheets

| matrix | 1. round | 2. round | 3. round | 4. round | 5. round | 6. round | 7. round | 8. round | 9. round | 10. round | 11. round | test for binding 11.-round | CR (I) 12.-round | DR (1) | test for binding | CR (J) 13.-round | DR (2) | test for binding | CR (J) 14.-round | DR (3) |
|---|---|---|---|---|---|---|---|---|---|---|---|---|---|---|---|---|---|---|---|---|
|  | NA | NA | NA | UL | UL | NA | UL | UL | NA | NA | UL | UL | UL | UL | UL | UL | UL | UL | UL | UL |
| C (ghrelin) |  |  |  |  |  |  |  |  |  |  |  |  |  |  |  |  |  |  |  |  |
| 3nM | 34 |  |  |  |  |  |  |  |  |  |  |  |  |  |  |  |  |  |  |  |
| 7nM |  | 43 |  |  | 440 |  |  |  |  |  |  |  | 1354 |  |  | 725 |  |  |  |  |
| 50nM |  |  |  | 3 | 25 | 57 |  |  |  |  |  |  |  |  |  |  |  |  |  |  |
| 250nM |  |  |  | 2 |  | 13 | 30 |  |  |  |  |  |  |  |  |  |  |  |  |  |
| 100nM |  |  |  |  |  |  | 31 | 25 | 38 |  | 14 | 39 |  |  | 362 |  |  |  |  |  |
| 50nM |  |  |  |  |  |  |  | 23 | 13 |  | 8 | 27 |  | 10 |  |  | 134 |  |  | 120 |
| 10nM |  |  |  |  |  |  |  |  | 14 | 77 |  |  |  |  |  |  |  |  |  |  |

Fig1 Tab 1A: signal/noise ratio for the RNA selection for D-ghrelin binding aptamers abbreviations:
NA - neutravidin agarose
UL - streptavidin ultralink CR - collection round
DR - double round (selection round without amplification with RNA from CR)

Fig. 1

Fig 2 Tab1B: signal/noise ratio for the 2'-F-RNA selection for D-ghrelin binding aptamers abbreviations:
NA - neutravidin agarose
UL - streptavidin ultralink CR - collection round
DR - double round (selection round without amplification with RNA from CR)

Fig. 2

|  | round 1 | round 2-5 | round 6-11/12 | collection rounds |
|---|---|---|---|---|
| RNA | 6nmol | 1nmol | 500pmol | 1000pmol |
| 2'F-RNA | 3nmol | 1nmol | 500pmol | 1000pmol |

Fig 3: amount of RNA/2'F-RNA used in the selection process

Fig. 3

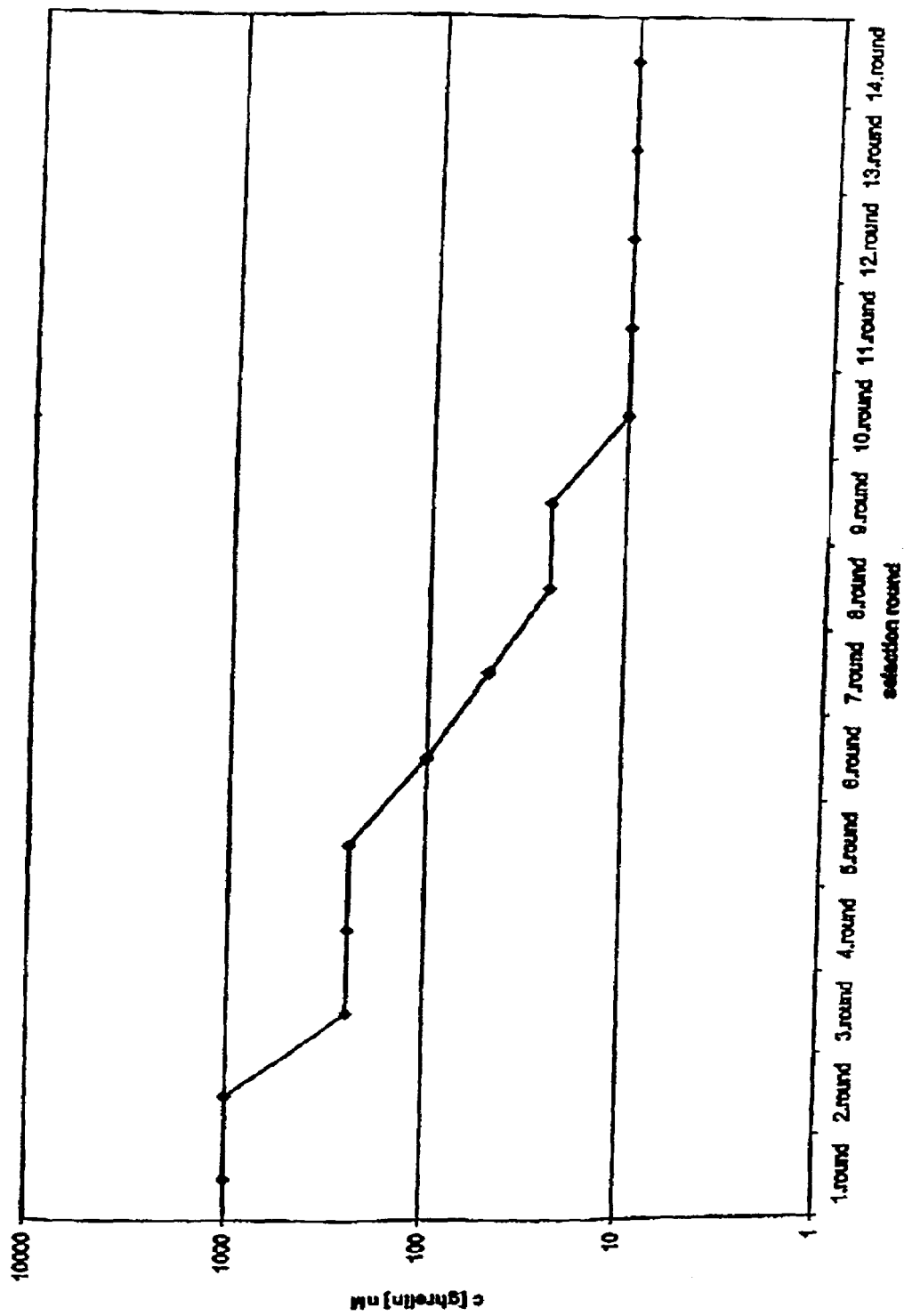
Fig. AA: course of the ghrelin peptide concentration for the RNA selection

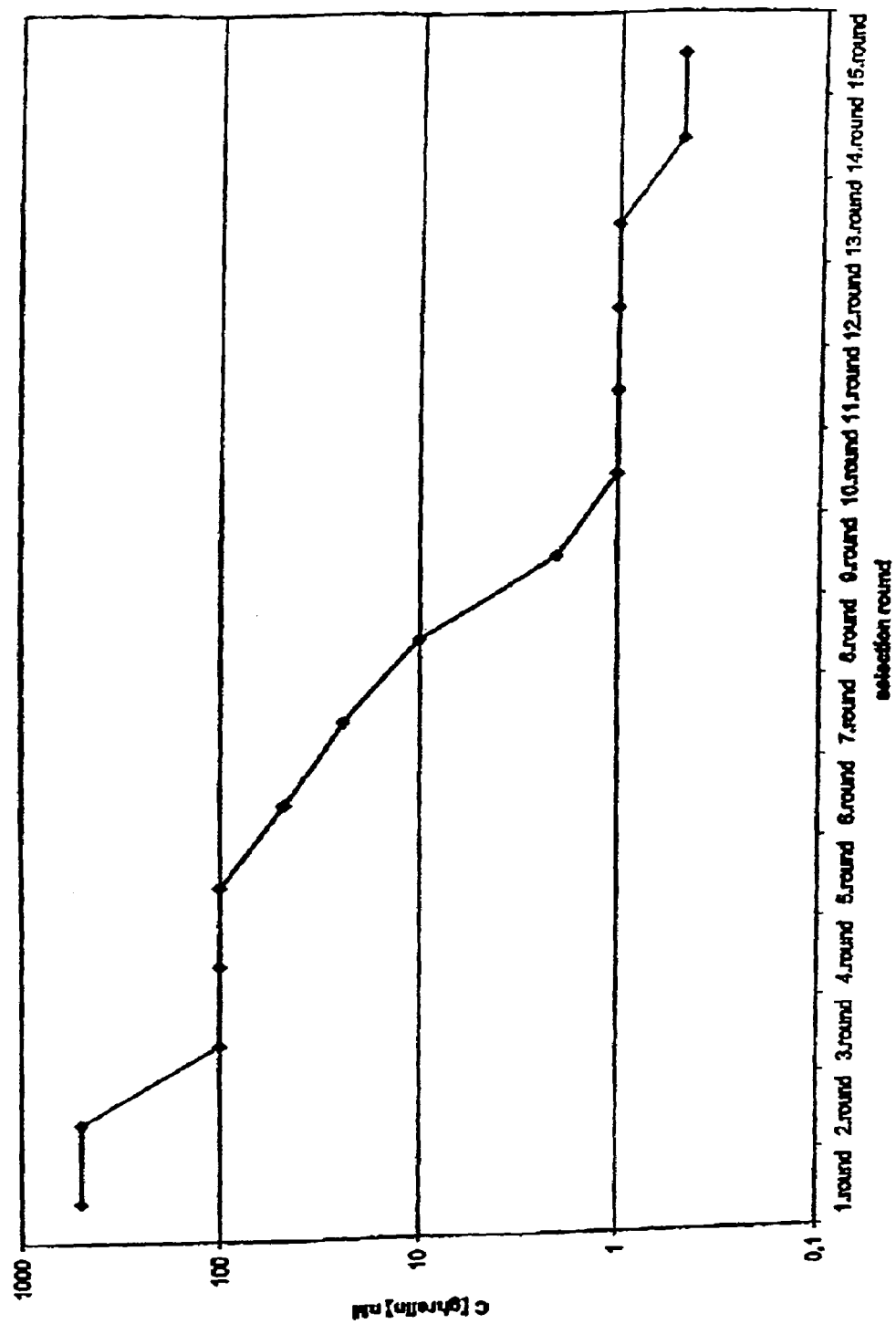
Fig.4B: course of the ghrelin peptide concentration for the 2'F-RNA selection

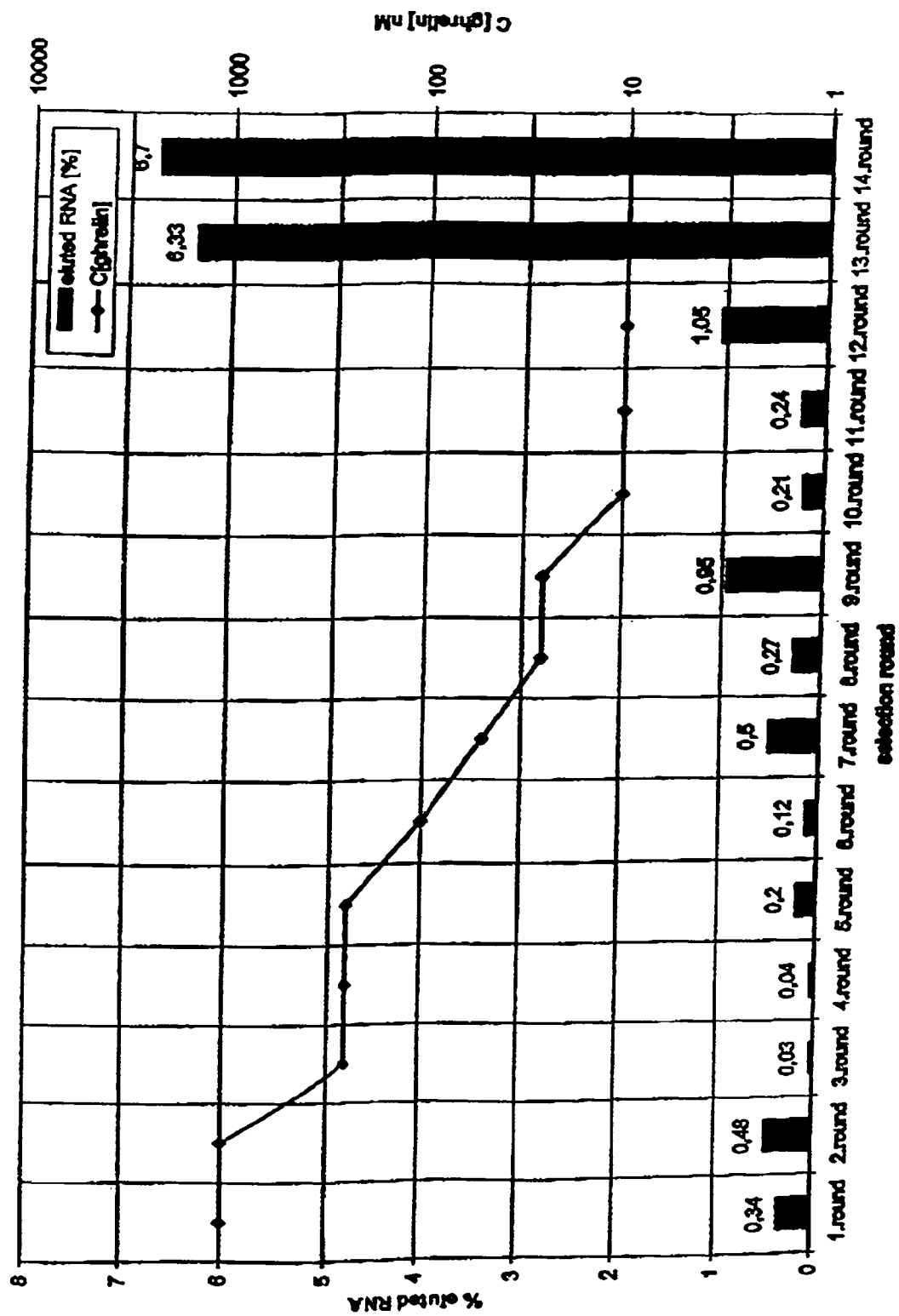
Fig. 5: Course of eluted RNA in percent of total used RNA and peptide concentration

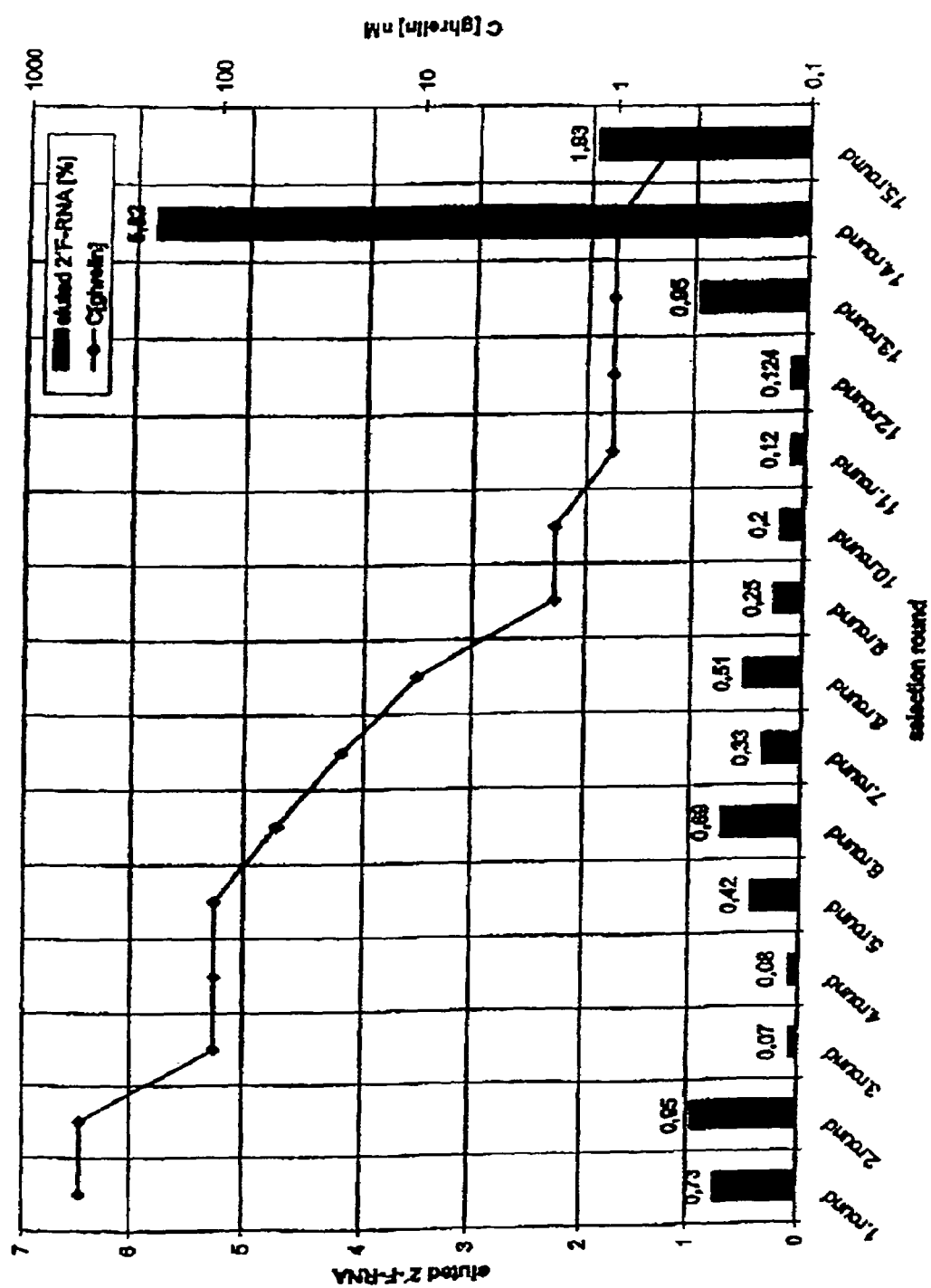
Fig.6: course of eluted 2'-F-RNA in percent of total used 2'F-RNA and peptide concentration

| | test for binding | CR (1) | DR (1) | test for binding | SCR (2) | DR (2) | test for binding | CR (3) | DR (3) |
|---|---|---|---|---|---|---|---|---|---|
| round | 12 | 12 | 12 | 13 | 13 | 13 | 14 | 14 | 14 |
| C [ghrelin] | | | | | | | | | |
| 3µM | | 31,6 | | | | | | | |
| 1µM | 22,6 | | | 32,5 | 14,5 | | 53,8 | | |
| 300nM | 4,98 | | | 15,6 | | | 35,7 | 25,3 | |
| 100nM | 0,78 | | | 7,9 | | | 28,2 | | |
| 30nM | 0,15 | | | 3,1 | | | 9,9 | | |
| 10nM | 0,13 | | 1,05 | 1,55 | | 6,33* | 3,5 | | 6,7* |

Fig. 7A Tab.3: double rounds and binding assays performed from round 12 to 14 for the RNA selection; data in percent binding to D-ghrelin, * sequenced

Fig. 7A

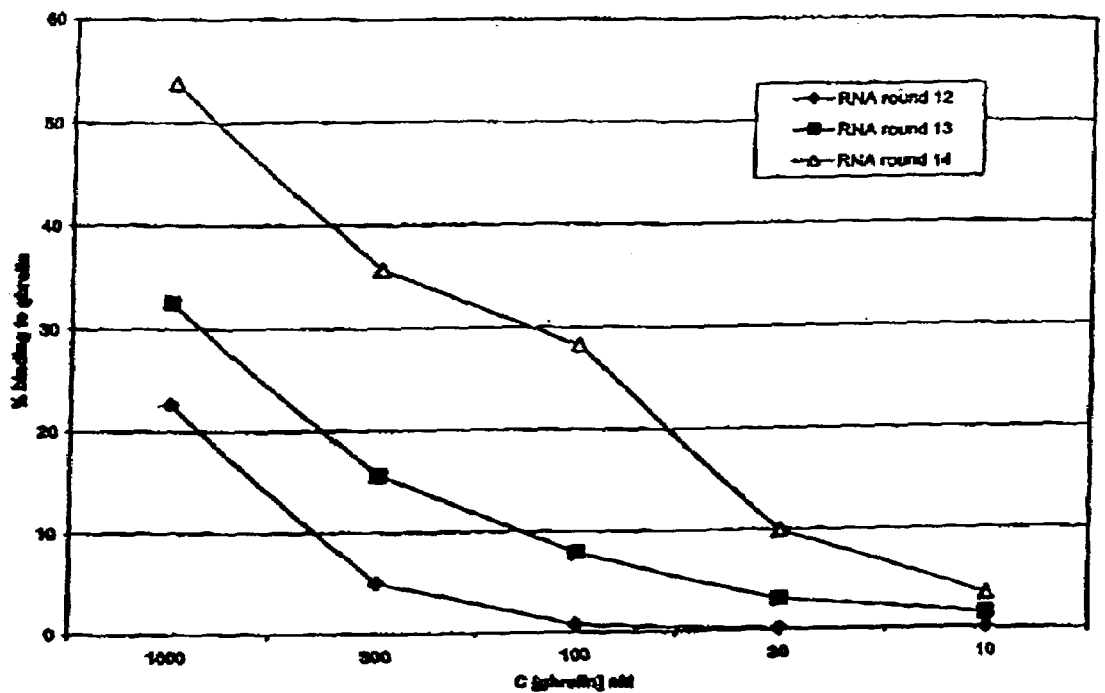
Fig.7B: Improvement of the RNA pool binding to D-ghrelin monitored over the double rounds

| | test for binding | CR (1) | DR (1) | test for binding | CR(2) | DR (2) | test for binding | CR (3) | DR (3) |
|---|---|---|---|---|---|---|---|---|---|
| round | 13 | 13 | 13 | 14 | 14 | 14 | 15 | 15 | 15 |
| C [ghrelin] | | | | | | | | | |
| 3µM | 42,4 | 31,4 | | | | | | | |
| 1µM | 28,8 | | | 45 | 28,7 | | 32,7 | 19,6 | |
| 300nM | 16,5 | | | 35,2 | | | 26,5 | | |
| 100nM | 8,49 | | | 29 | | | 18,1 | | |
| 30nM | 3,76 | | | 9,4 | | | 9,1 | | |
| 10nM | 0,72 | | | 3,9 | | | 1,7 | | |
| 1nM | | | 0,95 | | | 5,82* | | | 5,75 |
| 500pM | | | 0,43 | | | 0,75 | | | 1,93* |

Fig.8A Tab4: double rounds and binding assays performed from round 13 to 15 for the 2'F-RNA selection; data in percent binding to D-ghrelin, * sequenced

Fig. 8A

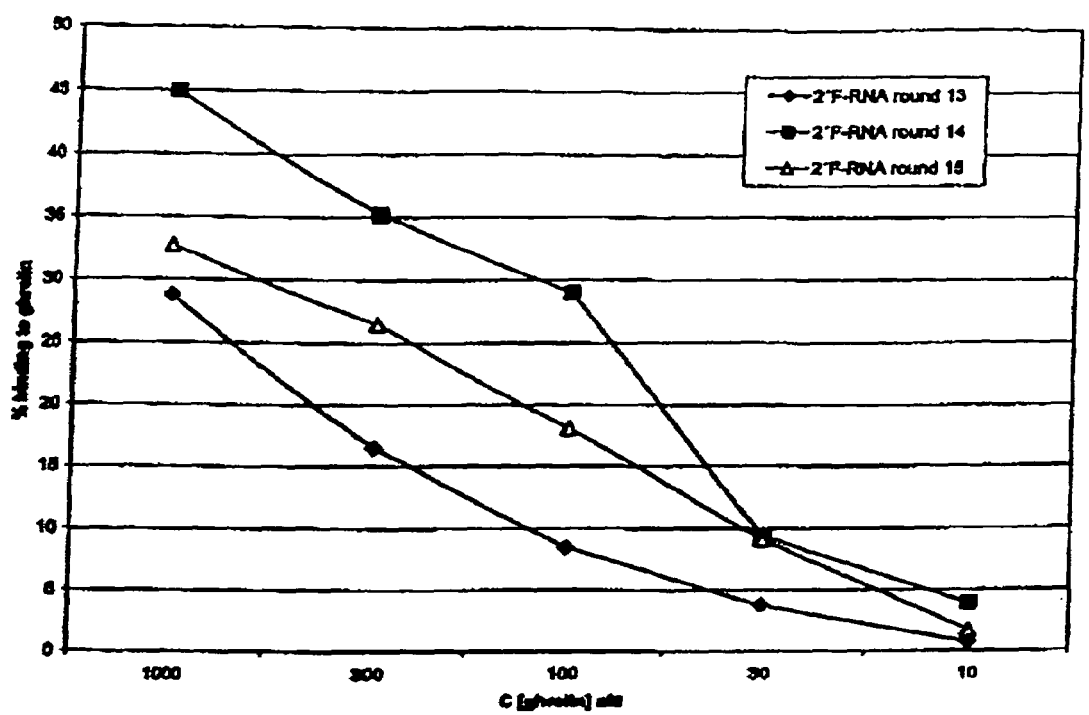
Fig.8B: Improvement of the 2'F-RNA pool binding to D-ghrelin monitored over the double rounds

Automated in vitro-Selection against Rat D-Ghrelin

| Round No. | A | B | C | Void | Remarks |
|---|---|---|---|---|---|
| 1 | 1 µM | | | | manual round |
| 2 | 1 µM | | | | manual round |
| 3 | 5 W | 10 W | 15 W | void 5 W | wash volume: 90 µl per wash (W) |
| 4 | 5 W | 10 W | 15 W | void 5 W | [D-Ghrelin] = 500 nM |
| 5 | 500 nM | 167 nM | 56 nM | void | 15 washes from round 5 |
| 6 | 500 nM | 167 nM | 56 nM | void | |
| 7 | 500 nM | 167 nM | 56 nM | void | |
| 8 | 500 nM | 167 nM | 56 nM | void | |
| 9 | 167 nM | 56 nM | 19 nM | void | |
| 10 | 167 nM | 56 nM | 19 nM | void | |
| 11 | 167 nM | 56 nM | 19 nM | void | |
| 12 | 56 nM | 19 nM | 6.2 nM | void | |
| 13 | 56 nM | 19 nM | 6.2 nM | void | |
| 14 | 56 nM | 19 nM | 6.2 nM | void | |
| 15 | 56 nM | 19 nM | 6.2 nM | void | |
| 16 | 19 nM | 6.2 nM | 2.1 nM | void | |
| 17 | 19 nM | 6.2 nM | 2.1 nM | void | |
| 18 | 6.2 nM | 2.1 nM | 0.7 nM | void | |
| 19 | 6.2 nM | 2.1 nM | 0.7 nM | void | |

Fig. 9

Table 5

| Position in Fig. 13 | Identifier | Total Occurrence | Occurrence Round 17 | Occurrence Round 19 |
|---|---|---|---|---|
| 1 | B11 | 65 | 35 | 30 |
| 7 | E3 | 5 | | 5 |
| 13 | F12 | 2 | 1 | 1 |
| 4 | B7 | 2 | | 2 |
| 5 | A8 | 2 | | 2 |
| 9 | C11 | 2 | | 2 |
| 10 | A3 | 2 | 2 | |
| 15 | G5 | 1 | 1 | |
| 11 | F5 | 1 | 1 | |
| 2 | G2 | 1 | 1 | |
| 6 | B12 | 1 | | 1 |
| 12 | A12 | 1 | | 1 |
| 3 | E12 | 1 | | 1 |
| 8 | C12 | 1 | | 1 |

Fig. 12

Sequences of the (+) strand complete forms:

```
                                                                                      Seq. ID
GGAGCUCAGACUUCACUCGUGUG---AGGCAAU----------AAAACU--UAAGUCCGAAGGUAACCAAUCCUAC--ACGUACCACUGUCGGUUCCAC    B11    7
GGAGCUCAGACUUCACUCGUGUG---AGGCAGU----------AAAACU--UAAGUCCGAAGGUAACCAAUCCUAC--ACGUACCACUGUCGGUUCCAC    G2     9
GGAGCUCAGACUUCACUCGUGUG---AGGCAAU----------AAAACU--UAAGUCCGAAGGUAACCAAUCCUGC--ACGUACCACUGUCGGUUCCAC    E12    11
GGAGCUCAGACUUCACUCGUGUG---AGGCAAU----------AAAACU--UAAGUCCGAAGGUAACCAAUCCUAC--ACGUACCACUGUCGGUUCCAC    B7     13
GGAGCUCAGACUUCACUCGUGUG---AGGCAAU----------AAAACA--UAAGUCCGAAGGUAACCAAUCCUAC--ACGUACCACUGUCGGUUCCAC    A8     15
GGAGCUCAGACUUCACUCGUGUG---AGGCAAU----------AAAACG--UAAGUCCGAAGGUAACCAAUCCUAC--ACGUACCACUGUCGGUUCCAC    B12    17
GGAGCUCAGACUUCACUCGUGUG---AGGCAAU----------AAAACUUGUAAGUCCGAAGGUAACCAAUCCUAC--ACGUACCACUGUCGGUUCCAC    E3     19
GGAGCUCAGACUUCACUCGUGUG---AGGCAAUA---------AAAACU--UAAGUCCGAAGGUAACCAAUCCUAC--ACGUACCACUGUCGGUUCCAC    C12    21
GGAGCUCAGACUUCACUCGUGCGGUGAGGCA------------AAAAC---GUAAGACCGAAGGUAACCAUUCCUACCACGUACCACUGUCGGUUCCAC    C11    23
GGAGCUCAGACUUCACUCGUGUG---AGGUAGUAAA-------AAAAC---GUAAAUCCGAAGGUAACCAAUCCUAC--ACGUACCACUGUCGGUUCCAC    A3     25
GGAGCUCAGACUUCACUCGUGUG---AGGUAGUAAAAA-----AAAAC---GUAAAUCCGAAGGUAACCAGUCCUAC--ACGUACCACUGUCGGUUCCAC    F5     27
GGAGCUCAGACUUCACUCGUGUG---AGGUAGUAAAAAAA---AAAAC---GUAAAUCCGAAGGUAACCAAUCCUAC--ACGUACCACUGUCGGUUCCAC    A12    29
GGAGCUCAGACUUCACUCGUGUG---AGGUAGUAAAAAAAA--AAAAC---GUAAAUCCGAAGGUAACCAAUCCUAC--ACGUACCACUGUCGGUUCCAC    F12    31
GGAGCUCAGACUUCACUCGUGUG---AGGUAGUAAAAAAAAAAAAAAAC--AURAAUCCGAAGGUAACCAAUCCUAC--ACGUACCACUGUCGGUUCCAC    G5     33
```

GGAGCUCAGACUUCACUCG
DE.40F-Primer (Seq. ID No. 35)

CGUACCACUGUCGGUUCCAC
DE.40R-Primer (rev. und
compl.)(Seq. ID No. 36)

Primer moieties underlined and in bold

Fig. 13-1

| core forms: | | Seq. ID. |
|---|---|---|
| CGUGUGAGGCAAUAAAACUUAAGUCCGAAGGUAACCAAUCCUACACG | B11 | 8 |
| CGUGUGAGGCAGUAAAACUUAAGUCCGAAGGUAACCAAUCCUACACG | G2 | 10 |
| CGUGUGAGGCAAUAAAACUUAAGUCCGAAGGUAACCAAUCCUGCACG | E12 | 12 |
| CGUGUGAGGCAAUAAAACAUAAGUCCGAAGGUAACCAAUCCUACACG | B7 | 14 |
| CGUGUGAGGCAAUAAAAGUCCGAAGGUAACCAAUCCUACACG | A8 | 16 |
| CGUGUGAGGCAAUAAAACUUGUAAGUCCGAAGGUAACCAAUCCUACACG | B12 | 18 |
| CGUGUGAGGCAAUAAAACUUAAGUCCGAAGGUAACCAAUCCUACACG | E3 | 20 |
| CGUGUGAGGCAAUAAAACUUAAGUCCGAAGGUAACCAUUCCUACCCACG | C12 | 22 |
| CGUGCGGUGAGGCAAAAACUAAGACCGAAGGUAACCAAUCCUACACG | C11 | 24 |
| CGUGUGAGGUAGUAGUAAAACGUAAAACGUAAAACCAAUCCAAUCCUACACG | A3 | 26 |
| CGUGUGAGGUAGUAGUAAAACGUAAAACGAAGGUAACCAGUCCUACACG | F5 | 28 |
| CGUGUGAGGUAGUAGUAAAAAAAACGUAAACGUAAACCGAAGGUAACCAAUCCUACACG | A12 | 30 |
| CGUGUGAGGUAGUAGUAAAAAAAAACGAAACCGAAGGUAACCAAUCCUACACG | F12 | 32 |
| CGUGUGAGGUAGUAGUAAAAAAAAAAAAAACAUAAAUCCGAAGGUAACCAAUCCUACACG | G5 | 34 |

Fig. 13 -2

Table 6

Clone B11

| [D-Ghrelin] in nM | % RNA bound |
|---|---|
| 0 | 0 |
| 3 | 2 |
| 10 | 8 |
| 30 | 35 |
| 100 | 62 |
| 300 | 76 |
| 1000 | 75 |
| 3000 | 83 |

Clone F12

| [D-Ghrelin] in nM | % RNA bound |
|---|---|
| 0 | 0 |
| 3 | 3 |
| 10 | 10 |
| 30 | 29 |
| 100 | 46 |
| 300 | 64 |
| 1000 | 91 |
| 3000 | 88 |

Clone E3

| [D-Ghrelin] in nM | % RNA bound |
|---|---|
| 0 | 0 |
| 3 | 1 |
| 10 | 5 |
| 30 | 20 |
| 100 | 54 |
| 300 | 65 |
| 1000 | 89 |
| 3000 | 85 |

Fig. 15

Table 7

| Clone | K$_D$ [nM] |
|---|---|
| A3 | 203 |
| A8 | 98 |
| A12 | 237 |
| B7 | 139 |
| B11 | 205 |
| B12 | 135 |
| C11 | 135 |
| C12 | 17 |
| E3 | 227 |
| E12 | 171 |
| F5 | 142 |
| F12 | 111 |
| G2 | 207 |
| G5 | 164 |

Fig. 17

Table 8

| Clone | $K_D$ [nM] |
|---|---|
| D-B11 | 205 |
| L-B11 trunc. | 104 |
| D-B11 trunc. | 122 |

Fig. 20

Sequences derived from the RNA selection (round 13)

Seq. RNA round 13
ID. group1
    1.1 main clone
38  'SOT-R04-BR13-E5  GGAGCTCAGACTTCACTCGTGCGGTGAGGCAGACG-TAAGACCGAAGGTAACCATTCCTACCCACGTACCACTGTCGGGTTCCAC group2
    2.1 main clone
39  'SOT-R04-BR13-A2  GGAGCTCAGACTTCACTCGTGCGGTGAGGCTAACG-TAAGACCGAAGGTAACCATTCCTACCCACGTACCACTGTCGGGTTCCAC
    variations of 2.1
40  'SOT-R04-BR13-C4  GGAGCTCAGACTTCACTCGTGTGGTGAGGCTAACG-TAAGACCGAAGGTAACCATTCCTACCCACGTACCACTGTCGGGTTCCAC group3
    3.1 main clone
41  'SOT-R04-BR13-C1  GGAGCTCAGACTTCACTCGTGTGAGGTAATAAAAC-TAAATCCGAAGGTAACCAATCCTAC--ACGTACCACTGTCGGGTTCCAC group4
    4.1 main clone
42  'SOT-R04-BR13-G2  GGAGCTCAGACTTCACTCGTGCCTACCGTTATAAAGGGAGTCCTGCAGACTGATGCCAGGCCACGTACCACTGTCGGGTTCCAC

Fig. 22

Sequences derived from the RNA selection (round 14)

| Seq. ID. | RNA round 14 | | |
|---|---|---|---|
| | group1 | | |
| | 1.1 (main clone) | | |
| 43 | 'SOT-R04-DR14-F7 | GGAGCTCAGACTTCACTCGTCGCGGTGAGGCAGA--CGTAAGACCGAAGGTAACCATTCCTACCACGTACCACTGTCGGTTCCAC |
| | variations of clone 1.1 | | |
| 44 | 'SOT-R04-DR14-C11 | GGAGCTCAGACTTCACTCGTGCGGTGAGGCAAA--CGTAAGACCGAAGGTAACCATTCCTACCACGTACCACTGTCGGTTCCAC |
| 45 | 'SOT-R04-DR14-A8 | GGAGCTCAGACTTCACTCGTGCGGTGAGGCTAA--CGTAAGACCGAAGGTAACCATTCCTACCACGTACCACTGTCGGTTCCAC |
| 46 | 'SOT-R04-DR14-C12 | GGAGCTCAGACTTCACTCGTGCGGTGAGGCAAAAACCTAAGACCGAAGGTAACCATTCCTACCACGTACCACTGTCGGTTCCAC |
| | group3 | | |
| | 3.1 (main clone) | | |
| 47 | 'SOT-R04-DR14-C7 | GGAGCTCAGACTTCACTCGTGTGAGGTAATAAAAC---TAAATCCGAAGGTAACCAATCCTAACGTACCACTGTCGGTTCCAC |
| | variations of clone 3.1 | | |
| 48 | 'SOT-R04-DR14-E11 | GGAGCTCAGACTTCACTCGTGTGAGGCAGTAAAACTT--AAGTCCGAAGGTAACCAATCCTAAGGTACCACTGTCGGTTCCAC |
| 49 | 'SOT-R04-DR14-H11 | GGAGCTCAGACTTCACTCGTGTGAGGCAATAAACTTG-AAGTCCGAAGGTAACCAATCCTAACGTACCACTGTCGGTTCCAC |
| 50 | 'SOT-R04-DR14-E8 | GGAGCTCAGACTTCACTCGTGTGAGGCGATAAAACTTGTAAGTCCGAAGGTAACCAATCCTAACGTACCACTGTCGGTTCCAC |

Fig. 23

Sequences derived from the 2'F-RNA selection (round 14)

Seq. 2'-F-RNA round 14
ID. group1
   1.1 (main clone)
51  'SOT-F03-DR14-G6  GGAGCTCAGACTCACTCGTGGAATAGGAATGACTCAGACTTTCT--CATACGTCGCCGCAACGTACCACTGTCGGTTCCAC mutations of clone 1.1
   1.2
52  'SOT-F03-DR14-F2  GGAGCTCAGACTCACTCGTGGAATAGGAATGACTCAGACCTTTCT--CATAGGTCGCCGCAACGTACCACTGTCGGTTCCAC
   1.3
53  'SOT-F03-DR14-F4  GGAGCTCAGACTCACTCGTGGAATAGGAATGACTCAGACCTTTC---ATAGGTCGCCGCAACGTACCACTGTCGGTTCCAC
   1.4
54  'SOT-F03-DR14-D5  GGAGCTCAGACTCACTCGTGGAATAGGAATGACTCAGAOGTTTCTC-CATAGGTCGCCGCAACGTACCACTGTCGGTTCCAC
   1.6
55  'SOT-F03-DR14-G3  GGAGCTCAGACTCACTCGTGGAATAGGAATGACTCAGACGTTTCTC-CAAACGTCGCCGCAACGTACCACTGTCGGTTCCAC
   1.7
56  'SOT-F03-DR14-B5  GGAGCTCAGACTCACTCGTGGAATAGGAATGACTCAGACGT-CTC-CATACGTCGCCGCAACGTACCACTGTCGGTTCCAC
   1.8
57  'SOT-F03-DR14-C2  GGAGCTCAGACTCACTCGTGGAATAGGAATGACTCAGACCTTTCTC-CATAGGTCGC---CAACGTACCACTGTCGGTTCCAC
   1.9
58  'SOT-F03-DR14-F3  GGAGCTCAGACTCACTCGTGGAATAGGAATGACTCAGACGTTTCTT-CATACGTCGCCGCAACGTACCACTGTCGGTTCCAC
   1.10
59  'SOT-F03-DR14-B6  GGAGCTCAGACTCACTCGTGGAATAGGAATGATTCAGACCTTTC----CATACGTCGCCGCAACGTACCACTGTCGGTTCCAC
   1.11
60  'SOT-F03-DR14-H1  GGAGCTCAGACTCACTCGTGGAATAGGAATGACTCAGACCTTTC----ATAGGTCGCCGCAACGTACCACTGTCGGTTCCAC
   1.12
61  'SOT-F03-DR14-F6  GGAGCTCAGACTCACTCGTGGTGGAATAGGAATGACTCAGACGTTT-----CATACGTCGCCGCAACGTACCACTGTCGGTTCCAC
   1.13
62  'SOT-F03-DR14-B1  GGAGCTCAGACTCACTCGTGGAATAGGAATGACTCAGACGT----C---CATACGTCGCCGCAACGTACCACTGTCGGTTCCAC
   1.14
63  'SOT-F03-DR14-C1  GGAGCTCAGACTCACTCGTGGAATAGGAATGACTCAGACGTTTTCCCATACGTCGCCGCAACGTACCACTGTCGGTTCCAC
   1.15
64  'SOT-F03-DR14-H5  GGAGCTCAGACTCACTCGTGGAATAGGAATGACTCAGACGTTTTC--CATACGTCGCCGCAACGTACCACTGTCGGTTCCAC

Fig. 24 - 1

| Seq. ID. | group2 | |
|---|---|---|
| 65 | 2.1 (main clone) *SOT-F03-DR14-G5 | GGAGCTCAGAGACTTCACTCGTGCGCTTTCTGTTAGCTGCCGACCGTCAGTGCGGCACGAGATACGTACCACTGTCGGTTCCAC |
| | variations of clone 2.1 | |
| 66 | 2.2 *SOT-F03-DR14-D3 | GGAGCTCAGAGACTTCACTCGTGCGCTTTCTGTTAGCTGCTGACCGTCAGTGCGGCACGAGATACGTACCACTGTCGGTTCCAC |
| 67 | 2.3 *SOT-F03-DR14-H2 | GGAGCTCAGAGACTTCACTCGTGCGCTTTCTGTTAGCT--CCGACCGTCAGTGCGGCAGAGATACGTACCACTGTCGGTTCCAC |
| 68 | 2.4 *SOT-F03-DR14-D1 | GGAGCTCAGAGACTTCACTCGTGCGCTTTCTGTTAGCT--CAGACCGTCAGTGCGGCACGAGATACGTACCACTGTCGGTTCCAC |
| 69 | 2.5 *SOT-F03-DR14-A2 | GGAGCTCAGAGACTTCACTCGTGCGCTTT-TGTTAGCT--CAGACCGTCAGTGCGGCACGAGATACGTACCACTGTCGGTTCCAC |
| 70 | 2.6 *SOT-F03-DR14-G2 | GGAGCTCAGAGACTTCACTCGTGCGCTTTCT---AGCTCTTAACCGACCGACCGTCGGCACGAG---ACGTACCACTGTCGGTTCCAC |

| | group3 | |
|---|---|---|
| 71 | 3.1 main clone *SOT-F03-DR14-H6 | GGAGCTCAGAGACTTCACTCGTGTGCCGCCCTTATTGTCAGGGAGCTTGAGCCGACACTGCGGACGTACCACTGTCGGTTCCAC |

Fig. 24-2:

Sequences derived from the 2'F-RNA selection (round 15)

| Seq. ID. | 2'-F-RNA round 15 | |
|---|---|---|
| | group1 | |
| 72 | 1.1 (main clone) | GGAGCTCAGACTTCACTCGTGGAATAGGAATGACTCAGAGCGTTTCT--CATACGT--CGCCGCAACGTACCACTGTCGGTTCCAC |
| 73 | 1.2 | GGAGCTCAGACTTCACTCGTGGAATAGGAATGACTCAGAGCGTTTCT--CAAACGT--CGCCGCAACGTACCACTGTCGGTTCCAC |
| 74 | 'SOT-F03-DR15-G7 1.3 | GGAGCTCAGACTTCACTCGTGGAATAGGAATGACTCAGAGCGTTTC---CATACGT--CGCCGCAACGTACCACTGTCGGTTCCAC |
| 75 | 'SOT-F03-DR15-F10 1.4 | GGAGCTCAGACTTCACTCGTGGAATAGGAATGACTCAGAGCGTTTC------ATGT--CGCCGCAACGTACCACTGTCGGTTCCAC |
| 76 | 'SOT-F03-DR15-D9 1.5 | GGAGCTCAGACTTCACTCGTGGAATAGGAATGACTCAGAGCGTTT-----CATACGT--CGCCGCAACGTACCACTGTCGGTTCCAC |
| 77 | 'SOT-F03-DR15-F12 1.6 | GGAGCTCAGACTTCACTCGTGGAATAGGAATGACTCAGAGCGTTT-----CATACGT--CGCCGCAACGTACCACTGTCGGTTCCAC |
| 78 | 'SOT-F03-DR15-G12 1.7 | GGAGCTCAGACTTCACTCGTGGAATAGGAATGACTCAGAGCGTTTC---CATACGT----CGCCGCAACGTACCACTGTCGGTTCCAC |
| 79 | 'SOT-F03-DR15-H7 1.8 | GGAGCTCAGACTTCACTCGTGGAATAGGAATGACTCAGAGCGTTTC---CATAGGT--CGCCGCAACGTACCACTGTCGGTTCCAC |
| 80 | 'SOT-F03-DR15-A11 1.9 | GGAGCTCAGACTTCACTCGTGGAATAGGAATGACTCAGAGACCTTCT--CATAGGT--CGCCGCAACGTACCACTGTCGGTTCCAC |
| 81 | 'SOT-F03-DR15-A8 1.10 | GGAGCTCAGACTTCACTCGTGGAATAGGAATGACTCAGAGACCTTTC--TCCATACGT--CGCCGCAACGTACCACTGTCGGTTCCAC |
| 82 | 'SOT-F03-DR15-F8 1.11 | GGAGCTCAGACTTCACTCGTGGAATAGGAATGACTCAGAGGCCTTC--TCTTCATAGGT--CGCCGCAACGTACCACTGTCGGTTCCAC |
| 83 | 'SOT-F03-DR15-C9 1.12 | GGAGCTCAGACTTCACTCGTGGAATAGGAATGACCCAGAGCGTTTT---CATACGT--CGCCGCAACGTACCACTGTCGGTTCCAC |
| 84 | 'SOT-F03-DR15-C12 1.13 | GGAGCTCAGACTTCACTCGTGGAATAGGAATGACTCAGAGACCTTTT---CATAGGT--CGCCGCAACGTACCACTGTCGGTTCCAC |
| 85 | 'SOT-F03-DR15-F7 | GGAGCTCAGACTTCACTCGTGGAATAGGAATGACTCAGAGCCTTTTT--CATAGGT--CGCCGCAACGTACCACTGTCGGTTCCAC |
| | group2 | |
| 86 | 'SOT-F03-DR15-C7 2.1 | GGAGCTCAGACTTCACTCGTGCGCTTTCTCTTAGCTGCGACCGTCAGTGCGGCACGAGATACGTACCACTGTCGGTTCCAC |

Fig. 25:

| SEQ ID NO | Identifier | Sequence |
|---|---|---|
| 101 | SOT-108-H3 | 5'-X-GGTGGGTGAGGCACACCCGTAAGTCCGAAGGTAACCAATCCTACCCACC-Y-3' |
| 102 | SOT-108-A6 | 5'-X-GGTGGGTGAGGCATTAACGTAAGACCGAAGGTAACCAATCCTACCACC-Y-3' |
| 103 | SOT-108-B7 | 5'-X-GGTGGGTGAGGCAGTTATGTAAGACCGAAGGTACCAATCCTACCACC-Y-3' |
| 104 | SOT-108-C2 | 5'-X-GGTGGGTGAGGCAGTCTTGTAAGACCGAAGGTAACCAATCCTACCCACC-Y-3' |
| 105 | SOT-108-C3 | 5'-X-GGTGGGTGAGGCATAAACGTAAGACCGAAGGTAACCAATCCTACCACC-Y-3' |
| 106 | SOT-108-A1 | 5'-X-GGTGGGTGAGGCAATGTCGTAAGTCCGAAGGTAACCAATCCTACCGCC-Y-3' |
| 107 | SOT-108-A3 | 5'-X-GGTGGGTGAGGCACTAAAATAAGACCGAAGGTAACCAATCCTACCACC-Y-3' |
| 108 | SOT-108-A4 | 5'-X-GGTGGGTGAGGCACGCAAATAAGACCGAAGGTAACCAATCCTACCACC-Y-3' |
| 109 | SOT-108-A5 | 5'-X-GGTGGGTGAGGCGGTTCACATAAGTCCGAAGGTAACCAATCCTACCACC-Y-3' |
| 110 | SOT-108-B1 | 5'-X-GGTGGGTGAGGCAGTAATGTAAGTAAGTCCGAAGGTAACCAATCCTACCCACC-Y-3' |
| 111 | SOT-108-B3 | 5'-X-GGTGGGTGAGGCAATTAAGTAAGTCCGAAGGTAACCAATCCTACCACC-Y-3' |
| 112 | SOT-108-B6 | 5'-X-GGTGGGTGAGGCATGCAAGTAAGTACCGAAGGTACCAATCCTACCACC-Y-3' |
| 113 | SOT-108-C4 | 5'-X-GGTGGGTGAGGCATTAACGTAAGACCGAAGGTAACCAATCTACCACC-Y-3' |
| 114 | SOT-108-C6 | 5'-X-GGTGGGTGAGGCACACAAATAAGTCCGAAGGTATCCAATCCAGTCCTACCACC-Y-3' |
| 115 | SOT-108-C8 | 5'-X-GGTGGGTGAGGCAGACACGTAAGACCGAAGGTAACCAATCCTACCACC-Y-3' |
| 116 | SOT-108-D5 | 5'-X-GGTGGGTGAGGCCTACAAATAAGTCCGAAGGTAACCAATCCTACCACC-Y-3' |
| 117 | SOT-108-E6 | 5'-X-GGTGGGTGAGGCGTACAAATAAGTAAGACCGAAGGTAACCAATCCGTCCTACCACC-Y-3' |
| 118 | SOT-108-F1 | 5'-X-GGTGGGTGAGGCAATAAAGTAAGACCGAAGGTAACCAATCCTACCTACC-Y-3' |
| 119 | SOT-108-F2 | 5'-X-GGTGGGTGAGGCAGCTATGTAAGTCCGAAGGTAACCAATCCTACCCACC-Y-3' |
| 120 | SOT-108-F7 | 5'-X-GGTGGGTGAGGCAATCCGATAAGTAAGACCGAAGGTAACCAATCCTACCCACC-Y-3' |
| 121 | SOT-108-G3 | 5'-X-GGTGGGTGAGGCAATCAAGTAAGTAAGACCGAAGGTAACCAATCCTACCCACC-Y-3' |
| 122 | SOT-108-G7 | 5'-X-GGTGGGTGAGGCATACAAGTAAGTCCGAAGGTAACCAATCCTACCACC-Y-3' |
| 123 | SOT-108-H4 | 5'-X-GGTGGGTGAGGCAGTTCAGTAAGTAAGACCGAAGGTAACCAATCCTACCACC-Y-3' |
| 124 | SOT-108-H5 | 5'-X-GGTGGGTGAGGCAGTAAAATAAGTCCGAAGGTATCCAATCCTACCCACC-Y-3' |
| 125 | SOT-108-D4 | 5'-X-GGTGGGTGAGGCAATCTGTGTGAAGACCAGATGTAAGACCGAAGGTAACCAATCCTACCCACC-Y-3' |

Fig. 31

| Seq ID | name | Sequence | size (nt) | Original clone |
|---|---|---|---|---|
| 87 | sot_d_1r_054 | GGTGGGTGAGGCAGTAATGTAAGTCCGAAGGTAACCAATCCTACCCACC | 49 | SOT-108-B1 |
| 88 | sot_d_1r_055 | GGGTGAGGCAGTAATGTAAGTCCGAAGGTAACCAATCCTACCC | 43 | SOT-108-B1 |
| 89 | sot_d_1r_056 | GGGTGAGGCAGCAGAGACACGTAAGTCCGAAGGTAACCAATCCTACCC | 43 | SOT-108-C8 |
| 90 | sot_d_1r_057 | GGTGGGTGAGGCAGCTATGTAAGTCCGAAGGTAACCAATCCTACCCACC | 49 | SOT-108-F2 |
| 91 | sot_d_1r_058 | GGGTGAGGCAGCTATGTCAAGTAAGTCCGAAGGTAACCAATCCTACCC | 43 | SOT-108-F2 |
| 92 | sot_d_1r_059 | GGGTGAGGCAGCCATGCAAGTTATGTAAGACCGAAGGTACCAATCCTACCC | 43 | SOT-108-B6 |
| 93 | sot_d_1r_060 | GGGTGAGGCAGTTATGTAAGACCGAAGGTAACCAATCCTACCC | 43 | SOT-108-B7 |
| 94 | sot_d_1r_061 | GGTGGGTGAGGCACACCCATAAGTCCGAAGGTAACCAATCCTACCCACC | 49 | SOT-108-D5 |
| 95 | sot_d_1r_062 | GGGTGAGGCACACCCATAAGTCCGAAGGTAACCAATCCTACCC | 43 | SOT-108-D5 |
| 96 | sot_d_1r_063 | GGGTGAGGCAATCCGATAAGTCCGAAGGTAACCAATCCTACCC | 43 | SOT-108-F7 |
| 97 | sot_d_1r_064 | GGGTGAGGCAGTAAATCCGAAGTAAGACCGAAGGTAACCAATCCTACCC | 43 | SOT-108-G3 |
| 98 | sot_d_1r_065 | GGGTGAGGCAGTTCAGTAACAAATAGTCCGAAGGTAACCAATCCTACCC | 43 | SOT-108-H4 |
| 99 | sot_d_1r_066 | GGGTGAGGCACGTACAACAAATAGTCCGAAGGTAACCAGTCCTACCC | 43 | SOT-108-E6 |
| 100 | sot_d_1r_067 | GGGTGAGGCACACAAATAAGTCCGAAGGTATCCAGTCCTACCC | 43 | SOT-108-C6 |

Fig. 33

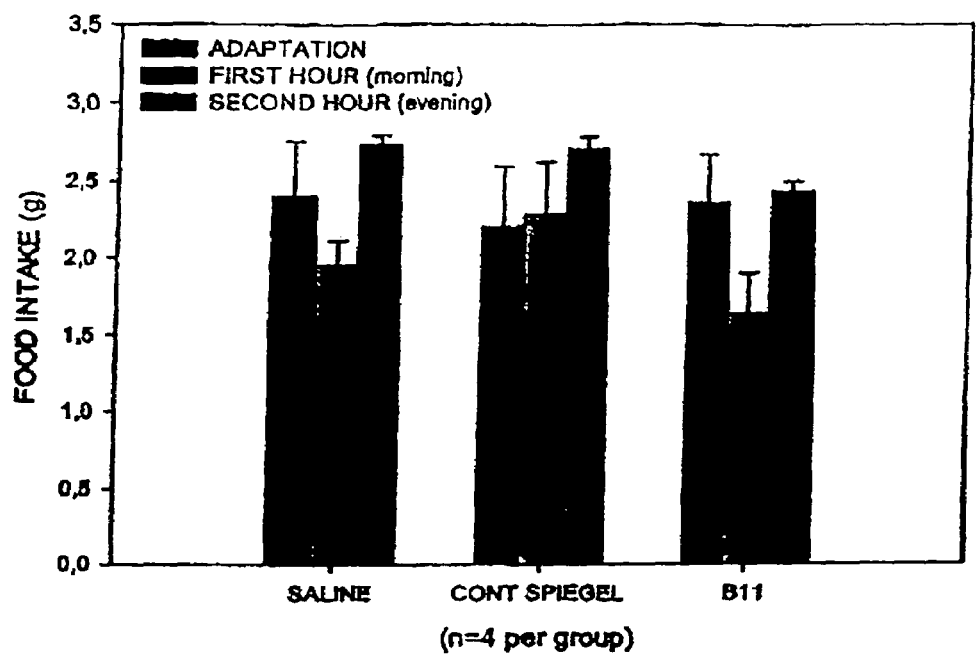
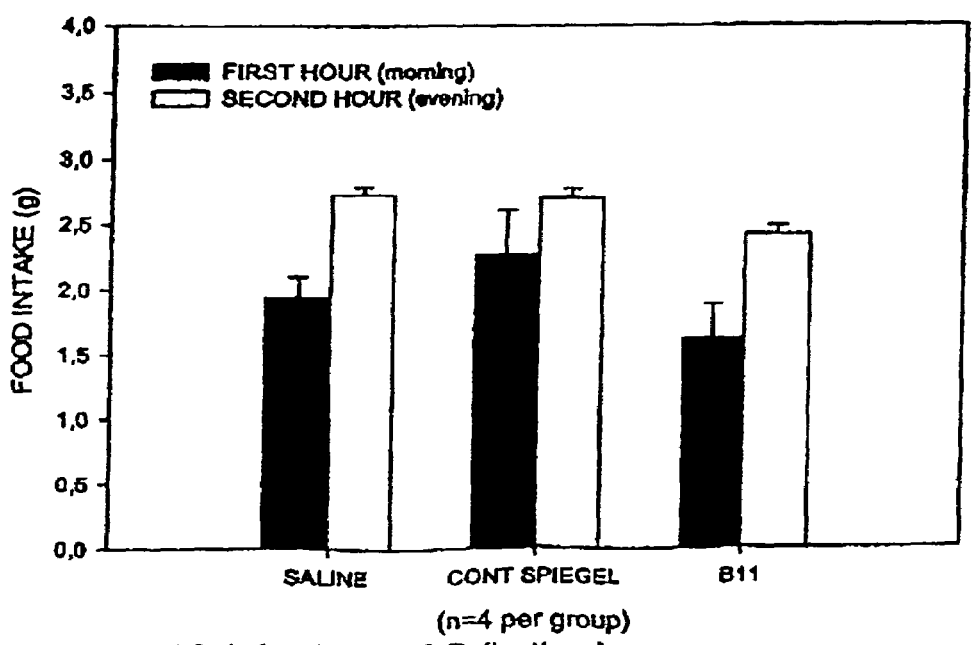
Figs. 39 A (top) and 39 B (bottom)

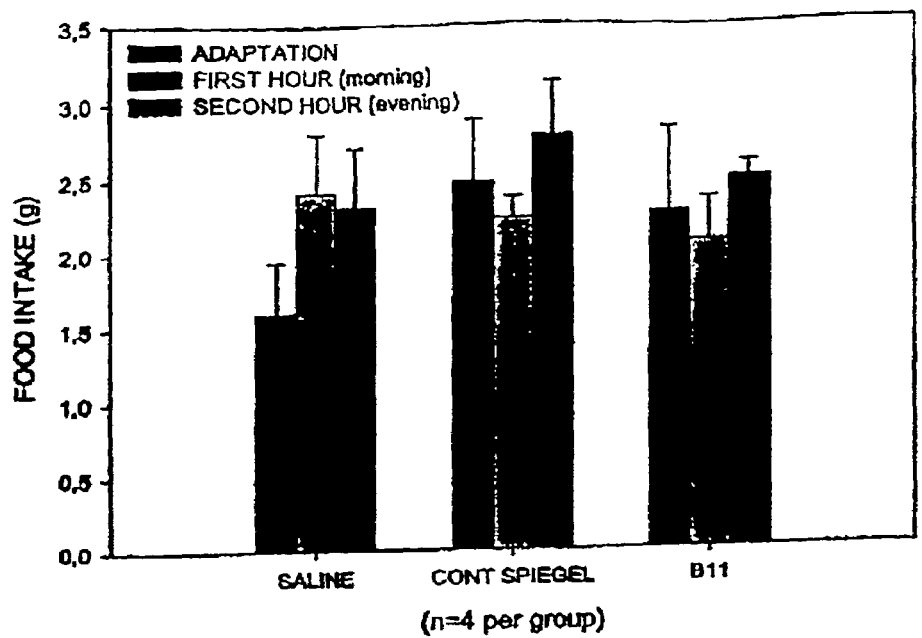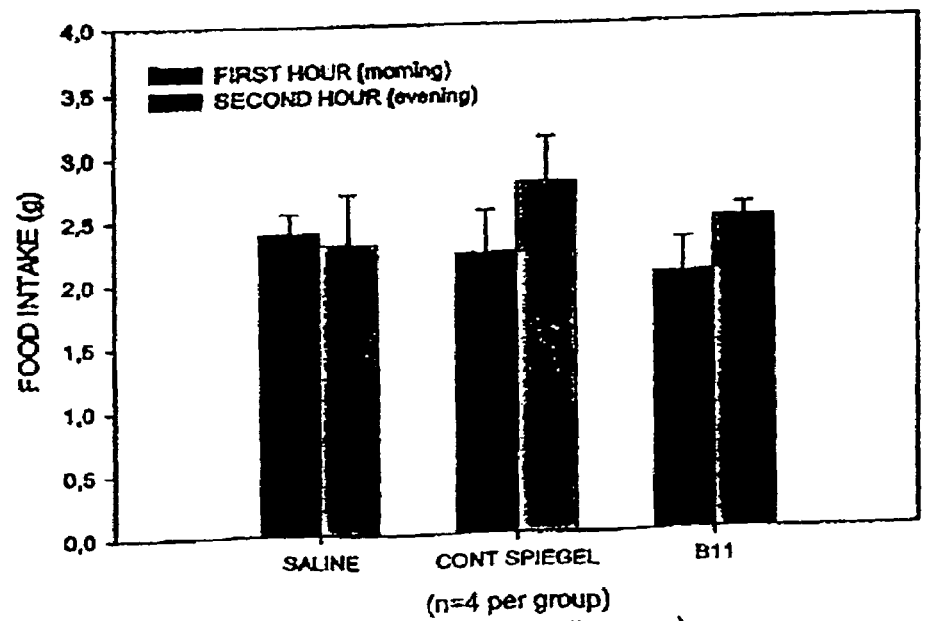
Figs. 40 A (top) and 40 B (bottom)

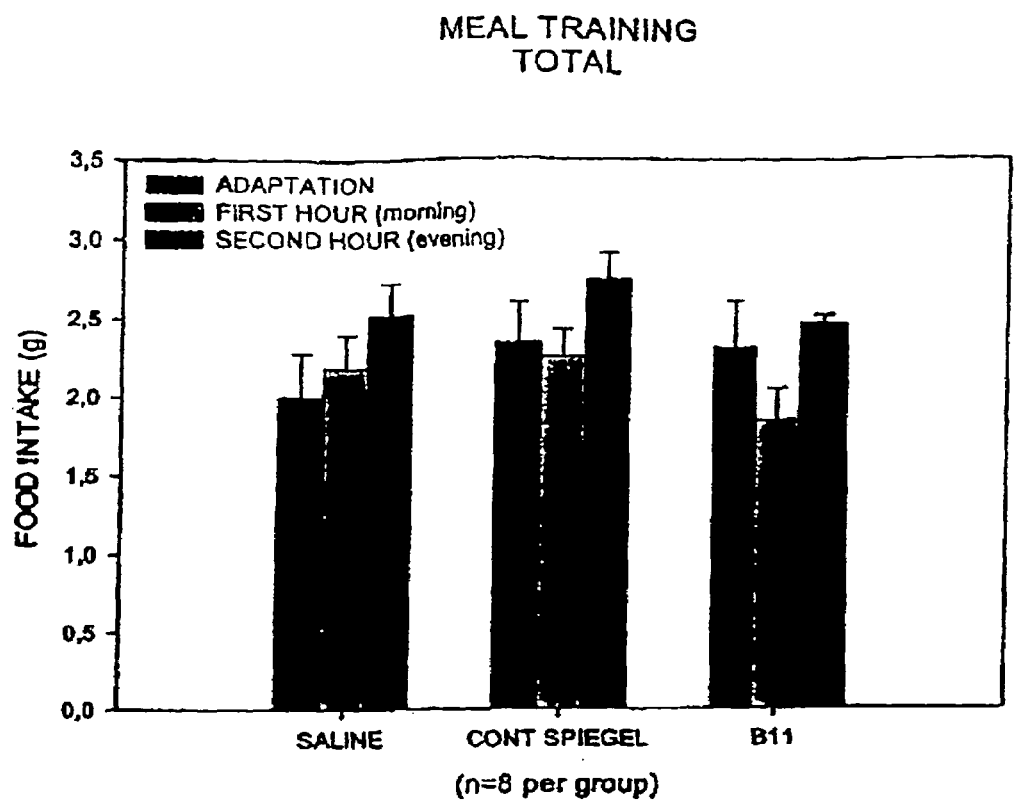
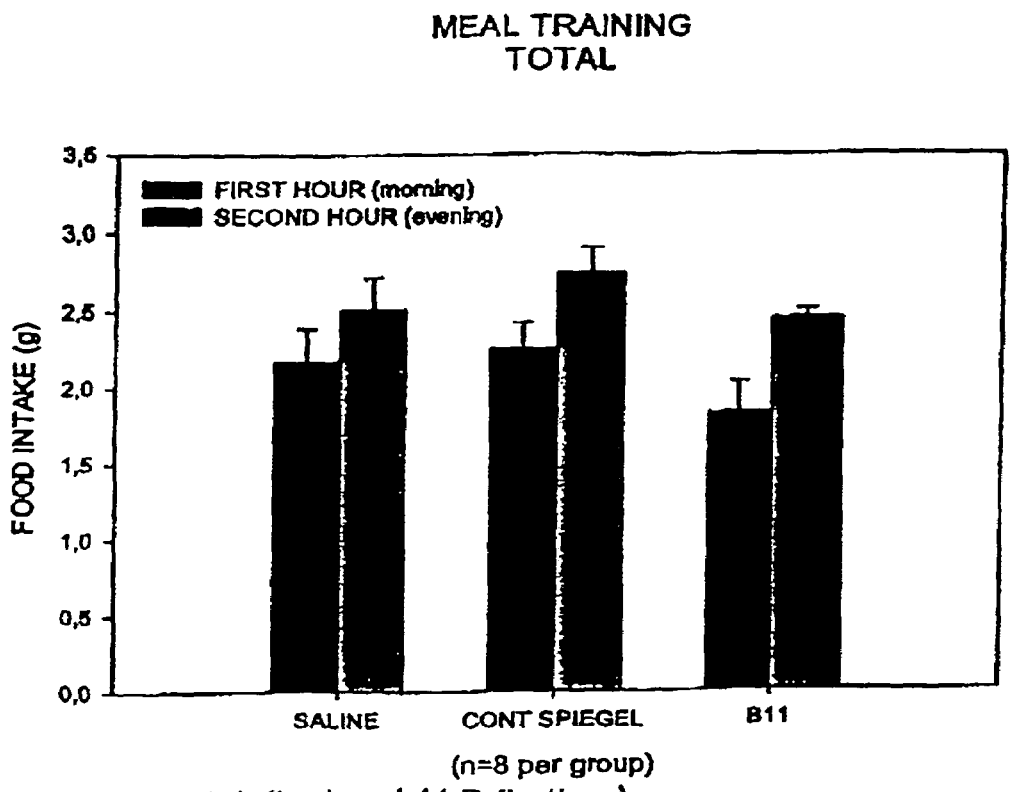
Figs. 41 A (top) and 41 B (bottom)

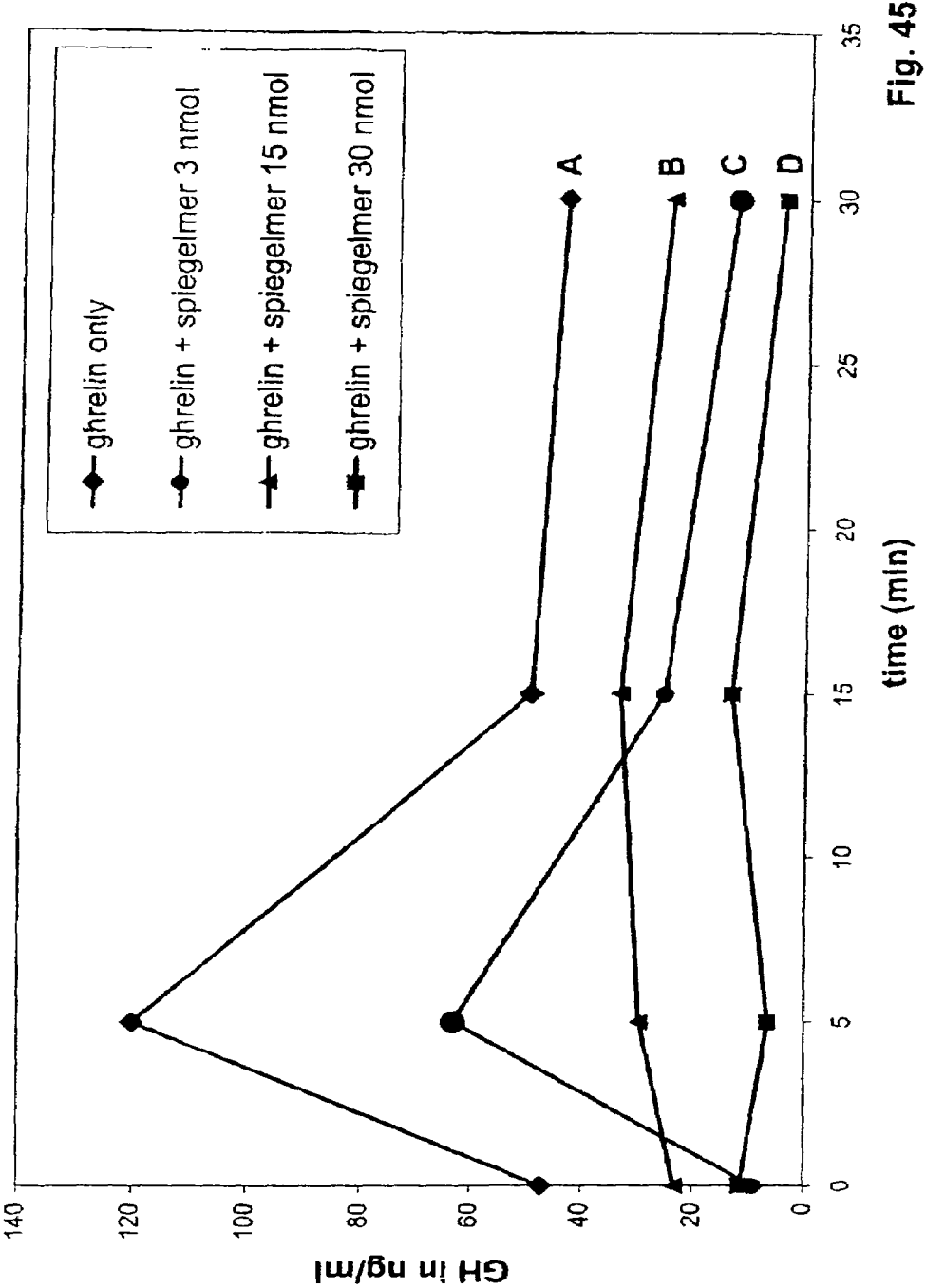

SEQUENCE LISTING

```
<160> NUMBER OF SEQ ID NOS: 130

<210> SEQ ID NO 1
<211> LENGTH: 28
<212> TYPE: PRT
<213> ORGANISM: Rattus rattus

<400> SEQUENCE: 1

Gly Ser Ser Phe Leu Ser Pro Glu His Gln Lys Ala Gln Gln Arg Lys
1               5                   10                  15

Glu Ser Lys Lys Pro Pro Ala Lys Leu Gln Pro Arg
            20                  25

<210> SEQ ID NO 2
<211> LENGTH: 83
<212> TYPE: RNA
<213> ORGANISM: Artificial Sequence
<220> FEATURE:
<223> OTHER INFORMATION: RNA pool
<220> FEATURE:
<221> NAME/KEY: misc_feature
<222> LOCATION: (22)..(61)
<223> OTHER INFORMATION: nucleotide = a, g, c or u

<400> SEQUENCE: 2
ggagcucaga cuucacucgu gnnnnnnnnn nnnnnnnnnn nnnnnnnnnn nnnnnnnnnn      60
```
ncacguacca cugucgguuc cac                                                    83

<210> SEQ ID NO 3
<211> LENGTH: 83
<212> TYPE: RNA
<213> ORGANISM: Artificial Sequence
<220> FEATURE:
<223> OTHER INFORMATION: RNA pool (reverse complementary strand)
<220> FEATURE:
<221> NAME/KEY: misc_feature
<222> LOCATION: (23)..(62)
<223> OTHER INFORMATION: nucleotide = a,g,c or u

<400> SEQUENCE: 3
guggaaccga cagugguacg ugnnnnnnnn nnnnnnnnnn nnnnnnnnnn nnnnnnnnnn            60
nncacgagug aagucugagc ucc                                                    83

<210> SEQ ID NO 4
<211> LENGTH: 38
<212> TYPE: DNA
<213> ORGANISM: Artificial Sequence
<220> FEATURE:
<223> OTHER INFORMATION: primer
<220> FEATURE:
<221> NAME/KEY: promoter
<222> LOCATION: (1)..(19)
<223> OTHER INFORMATION: T7 promoter

<400> SEQUENCE: 4
tctaatacga ctcactatag gagctcagac ttcactcg                                    38

<210> SEQ ID NO 5
<211> LENGTH: 20
<212> TYPE: DNA
<213> ORGANISM: Artificial Sequence
<220> FEATURE:
<223> OTHER INFORMATION: primer

<400> SEQUENCE: 5
gtggaaccga cagtggtacg                                                        20

<210> SEQ ID NO 6
<211> LENGTH: 102
<212> TYPE: DNA
<213> ORGANISM: Artificial Sequence
<220> FEATURE:
<223> OTHER INFORMATION: DNA pool
<220> FEATURE:
<221> NAME/KEY: misc_feature
<222> LOCATION: (41)..(80)
<223> OTHER INFORMATION: nucleotide is a, g, c or t

<400> SEQUENCE: 6
tctaatacga ctcactatag gagctcagac ttcactcgtg nnnnnnnnnn nnnnnnnnnn            60
nnnnnnnnnn nnnnnnnnnn cacgtaccac tgtcggttcc ac                              102

<210> SEQ ID NO 7
<211> LENGTH: 82
<212> TYPE: RNA
<213> ORGANISM: Artificial Sequence
<220> FEATURE:
<223> OTHER INFORMATION: Ghrelin-binding nucleic acid

<400> SEQUENCE: 7
ggagcucaga cuucacucgu gugaggcaau aaaacuuaag uccgaaggua accaauccua            60
cacguaccac ugucgguucc ac 82

<210> SEQ ID NO 8
<211> LENGTH: 47
<212> TYPE: RNA
<213> ORGANISM: Artificial Sequence
<220> FEATURE:
<223> OTHER INFORMATION: Ghrelin-binding nucleic acid

<400> SEQUENCE: 8
cgugugaggc aauaaaacuu aaguccgaag guaaccaauc cuacacg 47

<210> SEQ ID NO 9
<211> LENGTH: 82
<212> TYPE: RNA
<213> ORGANISM: Artificial Sequence
<220> FEATURE:
<223> OTHER INFORMATION: Ghrelin-binding nucleic acid

<400> SEQUENCE: 9
ggagcucaga cuucacucgu gugaggcagu aaaacuuaag uccgaaggua accaauccua 60
cacguaccac ugucgguucc ac 82

<210> SEQ ID NO 10
<211> LENGTH: 47
<212> TYPE: RNA
<213> ORGANISM: Artificial Sequence
<220> FEATURE:
<223> OTHER INFORMATION: Ghrelin-binding nucleic acid

<400> SEQUENCE: 10
cgugugaggc aguaaaacuu aaguccgaag guaaccaauc cuacacg 47

<210> SEQ ID NO 11
<211> LENGTH: 82
<212> TYPE: RNA
<213> ORGANISM: Artificial Sequence
<220> FEATURE:
<223> OTHER INFORMATION: Ghrelin-binding nucleic acid

<400> SEQUENCE: 11
ggagcucaga cuucacucgu gugaggcaau aaaacuuaag uccgaaggua accaauccug 60
cacguaccac ugucgguucc ac 82

<210> SEQ ID NO 12
<211> LENGTH: 47
<212> TYPE: RNA
<213> ORGANISM: Artificial Sequence
<220> FEATURE:
<223> OTHER INFORMATION: Ghrelin-binding nucleic acid

<400> SEQUENCE: 12
cgugugaggc aauaaaacuu aaguccgaag guaaccaauc cugcacg 47

<210> SEQ ID NO 13
<211> LENGTH: 82
<212> TYPE: RNA
<213> ORGANISM: Artificial Sequence
<220> FEATURE:
<223> OTHER INFORMATION: Ghrelin-binding nucleic acid

<400> SEQUENCE: 13
ggagcucaga cuucacucgu gugaggcaau aaaacauaag uccgaaggua accaauccua 60
cacguaccac ugucgguucc ac 82

<210> SEQ ID NO 14
<211> LENGTH: 47
<212> TYPE: RNA
<213> ORGANISM: Artificial Sequence
<220> FEATURE:
<223> OTHER INFORMATION: Ghrelin-binding nucleic acid

<400> SEQUENCE: 14
cgugugaggc aauaaaacau aaguccgaag guaaccaauc cuacacg                47

<210> SEQ ID NO 15
<211> LENGTH: 82
<212> TYPE: RNA
<213> ORGANISM: Artificial Sequence
<220> FEATURE:
<223> OTHER INFORMATION: Ghrelin-binding nucleic acid

<400> SEQUENCE: 15
ggagcucaga cuucacucgu gugaggcaau aaaacguaag uccgaaggua accaauccua    60
cacguaccac ugucgguucc ac                                            82

<210> SEQ ID NO 16
<211> LENGTH: 47
<212> TYPE: RNA
<213> ORGANISM: Artificial Sequence
<220> FEATURE:
<223> OTHER INFORMATION: Ghrelin-binding nucleic acid

<400> SEQUENCE: 16
cgugugaggc aauaaaacgu aaguccgaag guaaccaauc cuacacg                47

<210> SEQ ID NO 17
<211> LENGTH: 84
<212> TYPE: RNA
<213> ORGANISM: Artificial Sequence
<220> FEATURE:
<223> OTHER INFORMATION: Ghrelin-binding nucleic acid

<400> SEQUENCE: 17
ggagcucaga cuucacucgu gugaggcaau aaaacuugua aguccgaagg uaaccaaucc    60
uacacguacc acugucgguu ccac                                          84

<210> SEQ ID NO 18
<211> LENGTH: 49
<212> TYPE: RNA
<213> ORGANISM: Artificial Sequence
<220> FEATURE:
<223> OTHER INFORMATION: Ghrelin-binding nucleic acid

<400> SEQUENCE: 18
cgugugaggc aauaaaacuu guaaguccga agguaaccaa uccuacacg              49

<210> SEQ ID NO 19
<211> LENGTH: 83
<212> TYPE: RNA
<213> ORGANISM: Artificial Sequence
<220> FEATURE:
<223> OTHER INFORMATION: Ghrelin-binding nucleic acid

<400> SEQUENCE: 19
ggagcucaga cuucacucgu gugaggcaau aaaaacuuaa guccgaaggu aaccaauccu    60
acacguacca cugucgguuc cac                                           83

<210> SEQ ID NO 20
<211> LENGTH: 48
<212> TYPE: RNA
<213> ORGANISM: Artificial Sequence
<220> FEATURE:
<223> OTHER INFORMATION: Ghrelin-binding nucleic acid

<400> SEQUENCE: 20
cgugugaggc aauaaaaacu uaaguccgaa gguaaccaau ccuacacg        48

<210> SEQ ID NO 21
<211> LENGTH: 85
<212> TYPE: RNA
<213> ORGANISM: Artificial Sequence
<220> FEATURE:
<223> OTHER INFORMATION: Ghrelin-binding nucleic acid

<400> SEQUENCE: 21
ggagcucaga cuucacucgu gcggugaggc aaaaacguaa gaccgaaggu aaccauuccu    60
acccacguac cacgucggu uccac                                           85

<210> SEQ ID NO 22
<211> LENGTH: 50
<212> TYPE: RNA
<213> ORGANISM: Artificial Sequence
<220> FEATURE:
<223> OTHER INFORMATION: Ghrelin-binding nucleic acid

<400> SEQUENCE: 22
cgugcgguga ggcaaaaacg uaagaccgaa gguaaccauu ccuacccacg        50

<210> SEQ ID NO 23
<211> LENGTH: 85
<212> TYPE: RNA
<213> ORGANISM: Artificial Sequence
<220> FEATURE:
<223> OTHER INFORMATION: Ghrelin-binding nucleic acid

<400> SEQUENCE: 23
ggagcucaga cuucacucgu gugaggu agu aaaaaaacgu aaauccgaag guaaccauc    60 cuacacguac cacgucggu uccac                                           85

<210> SEQ ID NO 24
<211> LENGTH: 50
<212> TYPE: RNA
<213> ORGANISM: Artificial Sequence
<220> FEATURE:
<223> OTHER INFORMATION: Ghrelin-binding nucleic acid

<400> SEQUENCE: 24
cgugugaggu aguaaaaaaa cguaaauccg aagguaacca auccuacacg        50

<210> SEQ ID NO 25
<211> LENGTH: 88
<212> TYPE: RNA
<213> ORGANISM: Artificial Sequence
<220> FEATURE:
<223> OTHER INFORMATION: Ghrelin-binding nucleic acid

<400> SEQUENCE: 25
ggagcucaga cuucacucgu gugagguagu aaaaaaaaaa cguaaauccg aagguaacca    60
auccuacacg uaccacuguc gguuccac                                        88

<210> SEQ ID NO 26
<211> LENGTH: 53
<212> TYPE: RNA
<213> ORGANISM: Artificial Sequence
<220> FEATURE:
<223> OTHER INFORMATION: Ghrelin-binding nucleic acid

<400> SEQUENCE: 26
cgugugaggu aguaaaaaaa aaacguaaau ccgaaggUAA ccaauccuac acg    53

<210> SEQ ID NO 27
<211> LENGTH: 89
<212> TYPE: RNA
<213> ORGANISM: Artificial Sequence
<220> FEATURE:
<223> OTHER INFORMATION: Ghrelin-binding nucleic acid

<400> SEQUENCE: 27
ggagcucaga cuucacucgu gugagguagu aaaaaaaaaa acguaaaucc gaagguaacc    60
aguccuacac guaccacugu cgguuccac    89

<210> SEQ ID NO 28
<211> LENGTH: 54
<212> TYPE: RNA
<213> ORGANISM: Artificial Sequence
<220> FEATURE:
<223> OTHER INFORMATION: Ghrelin-binding nucleic acid

<400> SEQUENCE: 28
cgugugaggu aguaaaaaaa aaaacguaaa uccgaaggua accaguccua cacg    54

<210> SEQ ID NO 29
<211> LENGTH: 90
<212> TYPE: RNA
<213> ORGANISM: Artificial Sequence
<220> FEATURE:
<223> OTHER INFORMATION: Ghrelin-binding nucleic acid

<400> SEQUENCE: 29
ggagcucaga cuucacucgu gugagguagu aaaaaaaaaa aacguaaauc cgaagguaac    60
caauccuaca cguaccacug ucgguuccac    90

<210> SEQ ID NO 30
<211> LENGTH: 55
<212> TYPE: RNA
<213> ORGANISM: Artificial Sequence
<220> FEATURE:
<223> OTHER INFORMATION: Ghrelin-binding nucleic acid

<400> SEQUENCE: 30
cgugugaggu aguaaaaaaa aaaaacguaa auccgaaggu aaccaauccu acacg    55

<210> SEQ ID NO 31
<211> LENGTH: 91
<212> TYPE: RNA
<213> ORGANISM: Artificial Sequence
<220> FEATURE:
<223> OTHER INFORMATION: Ghrelin-binding nucleic acid

<400> SEQUENCE: 31
ggagcucaga cuucacucgu gugagguagu aaaaaaaaaa aaacguaaau ccgaagguaa    60
ccaauccuac acguaccacu gucgguucca c    91

<210> SEQ ID NO 32

-continued

```
<211> LENGTH: 56
<212> TYPE: RNA
<213> ORGANISM: Artificial Sequence
<220> FEATURE:
<223> OTHER INFORMATION: Ghrelin-binding nucleic acid

<400> SEQUENCE: 32
cgugugaggu aguaaaaaaa aaaaaacgua aauccgaagg uaaccaaucc uacacg          56

<210> SEQ ID NO 33
<211> LENGTH: 94
<212> TYPE: RNA
<213> ORGANISM: Artificial Sequence
<220> FEATURE:
<223> OTHER INFORMATION: Ghrelin-binding nucleic acid

<400> SEQUENCE: 33
ggagcucaga cuucacucgu gugagguagu aaaaaaaaa aaaaaacaua aauccgaagg        60
uaaccaaucc uacacguacc acugucgguu ccac                                  94

<210> SEQ ID NO 34
<211> LENGTH: 59
<212> TYPE: RNA
<213> ORGANISM: Artificial Sequence
<220> FEATURE:
<223> OTHER INFORMATION: Ghrelin-binding nucleic acid

<400> SEQUENCE: 34
cgugugaggu aguaaaaaaa aaaaaaaac auaaauccga agguaaccaa uccuacacg         59

<210> SEQ ID NO 35
<211> LENGTH: 19
<212> TYPE: RNA
<213> ORGANISM: Artificial Sequence
<220> FEATURE:
<223> OTHER INFORMATION: primer binding sequence

<400> SEQUENCE: 35
ggagcucaga cuucacucg                                                   19

<210> SEQ ID NO 36
<211> LENGTH: 20
<212> TYPE: RNA
<213> ORGANISM: Artificial Sequence
<220> FEATURE:
<223> OTHER INFORMATION: primer binding sequence

<400> SEQUENCE: 36
cguaccacug ucgguuccac                                                  20

<210> SEQ ID NO 37
<211> LENGTH: 47
<212> TYPE: RNA
<213> ORGANISM: Artificial Sequence
<220> FEATURE:
<223> OTHER INFORMATION: truncated B11

<400> SEQUENCE: 37
cgugugaggc aauaaaacuu aaguccgaag guaaccaauc cuacacg                    47

<210> SEQ ID NO 38
<211> LENGTH: 83
<212> TYPE: RNA
<213> ORGANISM: Artificial Sequence
<220> FEATURE:
<223> OTHER INFORMATION: Ghrelin-binding nucleic acid
```

```
<400> SEQUENCE: 38
ggagcucaga cuucacucgu gcggugaggc agacguaaga ccgaagguaa ccauuccuac    60
ccacguacca cgucgguuc cac                                            83

<210> SEQ ID NO 39
<211> LENGTH: 83
<212> TYPE: RNA
<213> ORGANISM: Artificial Sequence
<220> FEATURE:
<223> OTHER INFORMATION: Ghrelin-binding nucleic acid

<400> SEQUENCE: 39
ggagcucaga cuucacucgu gcggugaggc uaacguaaga ccgaagguaa ccauuccuac    60
ccacguacca cgucgguuc cac                                            83

<210> SEQ ID NO 40
<211> LENGTH: 83
<212> TYPE: RNA
<213> ORGANISM: Artificial Sequence
<220> FEATURE:
<223> OTHER INFORMATION: Ghrelin-binding nucleic acid

<400> SEQUENCE: 40
ggagcucaga cuucacucgu guggugaggc uaacguaaga ccgaagguaa ccauuccuac    60
ccacguacca cgucgguuc cac                                            83

<210> SEQ ID NO 41
<211> LENGTH: 81
<212> TYPE: RNA
<213> ORGANISM: Artificial Sequence
<220> FEATURE:
<223> OTHER INFORMATION: Ghrelin-binding nucleic acid

<400> SEQUENCE: 41
ggagcucaga cuucacucgu gugagguaau aaaacuaaau ccgaagguaa ccaauccuac    60
acguaccacu gucgguucca c                                             81

<210> SEQ ID NO 42
<211> LENGTH: 83
<212> TYPE: RNA
<213> ORGANISM: Artificial Sequence
<220> FEATURE:
<223> OTHER INFORMATION: Ghrelin-binding nucleic acid

<400> SEQUENCE: 42
ggagcucaga cuucacucgu gcguaccguu auaaagggag uccugcagac ugaugccagg    60
ccacguacca cugucgguuc cac                                           83

<210> SEQ ID NO 43
<211> LENGTH: 82
<212> TYPE: RNA
<213> ORGANISM: Artificial Sequence
<220> FEATURE:
<223> OTHER INFORMATION: Ghrelin-binding nucleic acid

<400> SEQUENCE: 43
ggagcucaga cuucacucgu gcggugaggc agacguaaga ccgaagguaa ccauuccuac    60
cacguaccac gucgguucc ac                                             82

<210> SEQ ID NO 44
```

```
<211> LENGTH: 82
<212> TYPE: RNA
<213> ORGANISM: Artificial Sequence
<220> FEATURE:
<223> OTHER INFORMATION: Ghrelin-binding nucleic acid

<400> SEQUENCE: 44
ggagcucaga cuucacucgu gcggugaggc aaacguaaga ccgaagguaa ccauuccuac    60
cacguaccac ugucgguucc ac                                            82

<210> SEQ ID NO 45
<211> LENGTH: 82
<212> TYPE: RNA
<213> ORGANISM: Artificial Sequence
<220> FEATURE:
<223> OTHER INFORMATION: Ghrelin-binding nucleic acid

<400> SEQUENCE: 45
ggagcucaga cuucacucgu gcggugaggc uaacguaaga ccgaagguaa ccauuccuac    60
cacguaccac ugucgguucc ac                                            82

<210> SEQ ID NO 46
<211> LENGTH: 84
<212> TYPE: RNA
<213> ORGANISM: Artificial Sequence
<220> FEATURE:
<223> OTHER INFORMATION: Ghrelin-binding nucleic acid

<400> SEQUENCE: 46
ggagcucaga cuucacucgu gcggugaggc aaaaacguaa gaccgaaggu aaccauuccu    60
accacguacc acugucgguu ccac                                          84

<210> SEQ ID NO 47
<211> LENGTH: 80
<212> TYPE: RNA
<213> ORGANISM: Artificial Sequence
<220> FEATURE:
<223> OTHER INFORMATION: Ghrelin-binding nucleic acid

<400> SEQUENCE: 47
ggagcucaga cuucacucgu gugagguaau aaaacuaaau ccgaagguaa ccaauccuaa    60
cguaccacug ucgguuccac                                               80

<210> SEQ ID NO 48
<211> LENGTH: 81
<212> TYPE: RNA
<213> ORGANISM: Artificial Sequence
<220> FEATURE:
<223> OTHER INFORMATION: Ghrelin-binding nucleic acid

<400> SEQUENCE: 48
ggagcucaga cuucacucgu gugaggcagu aaaacuuaag uccgaaggua accaauccua    60
acguaccacu gucgguucca c                                             81

<210> SEQ ID NO 49
<211> LENGTH: 82
<212> TYPE: RNA
<213> ORGANISM: Artificial Sequence
<220> FEATURE:
<223> OTHER INFORMATION: Ghrelin-binding nucleic acid

<400> SEQUENCE: 49
ggagcucaga cuucacucgu gugaggcaau uaaacuugaa guccgaaggu aaccaauccu    60
```

```
aacguaccac ugucgguucc ac                                             82

<210> SEQ ID NO 50
<211> LENGTH: 83
<212> TYPE: RNA
<213> ORGANISM: Artificial Sequence
<220> FEATURE:
<223> OTHER INFORMATION: Ghrelin-binding nucleic acid

<400> SEQUENCE: 50
ggagcucaga cuucacucgu gugaggcgau aaaacuugua aguccgaagg uaaccaaucc     60
uaacguacca cugucgguuc cac                                            83

<210> SEQ ID NO 51
<211> LENGTH: 81
<212> TYPE: RNA
<213> ORGANISM: Artificial Sequence
<220> FEATURE:
<223> OTHER INFORMATION: Ghrelin-binding nucleic acid

<400> SEQUENCE: 51
ggagcucaga cuucacucgu ggaauaggaa ugacucagac guuucucaua cgucgccgca     60
acguaccacu gucgguucca c                                              81

<210> SEQ ID NO 52
<211> LENGTH: 83
<212> TYPE: RNA
<213> ORGANISM: Artificial Sequence
<220> FEATURE:
<223> OTHER INFORMATION: Ghrelin-binding nucleic acid
<220> FEATURE:
<221> NAME/KEY: misc_feature
<223> OTHER INFORMATION: 2'-Flouro-modified pyrimidines

<400> SEQUENCE: 52
ggagcucaga cuucacucgu ggaauaggaa ugacucagac cuuucucaua ggucgccgca     60
ccacguacca cugucgguuc cac                                            83

<210> SEQ ID NO 53
<211> LENGTH: 82
<212> TYPE: RNA
<213> ORGANISM: Artificial Sequence
<220> FEATURE:
<223> OTHER INFORMATION: Ghrelin-binding nucleic acid
<220> FEATURE:
<221> NAME/KEY: misc_feature
<223> OTHER INFORMATION: 2'-Flouro-modified pyrimidines

<400> SEQUENCE: 53
ggagcucaga cuucacucgu ggaauaggaa ugacucagac cuuucuauag gucgccgcac     60
cacguaccac ugucgguucc ac                                             82

<210> SEQ ID NO 54
<211> LENGTH: 84
<212> TYPE: RNA
<213> ORGANISM: Artificial Sequence
<220> FEATURE:
<223> OTHER INFORMATION: Ghrelin-binding nucleic acid
<220> FEATURE:
<221> NAME/KEY: misc_feature
<223> OTHER INFORMATION: 2'-Flouro-modified pyrimidines

<400> SEQUENCE: 54
ggagcucaga cuucacucgu ggaauaggaa ugacucagac guuucuccau acgucgccgc     60
```

```
accacguacc acugucgguu ccac                                                    84

<210> SEQ ID NO 55
<211> LENGTH: 84
<212> TYPE: RNA
<213> ORGANISM: Artificial Sequence
<220> FEATURE:
<223> OTHER INFORMATION: Ghrelin-binding nucleic acid
<220> FEATURE:
<221> NAME/KEY: misc_feature
<223> OTHER INFORMATION: 2'-Flouro-modified pyrimidines

<400> SEQUENCE: 55
ggagcucaga cuucacucgu ggaauaggaa ugacucagac guuucuccaa acgucgccgc              60
accacguacc acugucgguu ccac                                                    84

<210> SEQ ID NO 56
<211> LENGTH: 83
<212> TYPE: RNA
<213> ORGANISM: Artificial Sequence
<220> FEATURE:
<223> OTHER INFORMATION: Ghrelin-binding nucleic acid
<220> FEATURE:
<221> NAME/KEY: misc_feature
<223> OTHER INFORMATION: 2'-Flouro-modified pyrimidines

<400> SEQUENCE: 56
ggagcucaga cuucacucgu ggaauaggaa ugacucagac guuucuccaua cgucgccgca             60 ccacguacca cugucgguuc cac                                                     83

<210> SEQ ID NO 57
<211> LENGTH: 82
<212> TYPE: RNA
<213> ORGANISM: Artificial Sequence
<220> FEATURE:
<223> OTHER INFORMATION: Ghrelin-binding nucleic acid
<220> FEATURE:
<221> NAME/KEY: misc_feature
<223> OTHER INFORMATION: 2'-Flouro-modified pyrimidines

<400> SEQUENCE: 57
ggagcucaga cuucacucgu ggaauaggaa ugacucagac cuuucuccau aggucgccac              60
cacguaccac ugucgguucc ac                                                      82

<210> SEQ ID NO 58
<211> LENGTH: 84
<212> TYPE: RNA
<213> ORGANISM: Artificial Sequence
<220> FEATURE:
<223> OTHER INFORMATION: Ghrelin-binding nucleic acid
<220> FEATURE:
<221> NAME/KEY: misc_feature
<223> OTHER INFORMATION: 2'-Flouro-modified pyrimidines

<400> SEQUENCE: 58
ggagcucaga cuucacucgu ggaauaggaa ugacucagac guuucuucau acgucgccgc              60
accacguacc acugucgguu ccac                                                    84

<210> SEQ ID NO 59
<211> LENGTH: 82
<212> TYPE: RNA
<213> ORGANISM: Artificial Sequence
<220> FEATURE:
<223> OTHER INFORMATION: Ghrelin-binding nucleic acid
<220> FEATURE:
```

```
<221> NAME/KEY: misc_feature
<223> OTHER INFORMATION: 2'-Flouro-modified pyrimidines

<400> SEQUENCE: 59
ggagcucaga cuucacucgu ggaauaggaa ugauucagac guuuccauac gucgccgcac    60
cacguaccac ugucgguucc ac                                            82

<210> SEQ ID NO 60
<211> LENGTH: 81
<212> TYPE: RNA
<213> ORGANISM: Artificial Sequence
<220> FEATURE:
<223> OTHER INFORMATION: Ghrelin-binding nucleic acid
<220> FEATURE:
<221> NAME/KEY: misc_feature
<223> OTHER INFORMATION: 2'-Flouro-modified pyrimidines

<400> SEQUENCE: 60
ggagcucaga cuucacucgu ggaauaggaa ugacucagac cuuucauagg ucgccgcacc    60
acguaccacu gucgguucca c                                             81

<210> SEQ ID NO 61
<211> LENGTH: 81
<212> TYPE: RNA
<213> ORGANISM: Artificial Sequence
<220> FEATURE:
<223> OTHER INFORMATION: Ghrelin-binding nucleic acid
<220> FEATURE:
<221> NAME/KEY: misc_feature
<223> OTHER INFORMATION: 2'-Flouro-modified pyrimidines

<400> SEQUENCE: 61
ggagcucaga cuucacucgu ggaauaggaa ugacucagac guuucauacg ucgccgcacc    60
acguaccacu gucgguucca c                                             81

<210> SEQ ID NO 62
<211> LENGTH: 80
<212> TYPE: RNA
<213> ORGANISM: Artificial Sequence
<220> FEATURE:
<223> OTHER INFORMATION: Ghrelin-binding nucleic acid
<220> FEATURE:
<221> NAME/KEY: misc_feature
<223> OTHER INFORMATION: 2'-Flouro-modified pyrimidines

<400> SEQUENCE: 62
ggagcucaga cuucacucgu ggaauaggaa ugacucagac guccauacgu cgccgcacca    60
cguaccacug ucgguuccac                                               80

<210> SEQ ID NO 63
<211> LENGTH: 85
<212> TYPE: RNA
<213> ORGANISM: Artificial Sequence
<220> FEATURE:
<223> OTHER INFORMATION: Ghrelin-binding nucleic acid
<220> FEATURE:
<221> NAME/KEY: misc_feature
<223> OTHER INFORMATION: 2'-Flouro-modified pyrimidines

<400> SEQUENCE: 63
ggagcucaga cuucacucgu ggaauaggaa ugacucagac guuucucca uacgucgccg    60 caccacguac cacugucggu uccac                                         85

<210> SEQ ID NO 64
```

<211> LENGTH: 84
<212> TYPE: RNA
<213> ORGANISM: Artificial Sequence
<220> FEATURE:
<223> OTHER INFORMATION: Ghrelin-binding nucleic acid
<220> FEATURE:
<221> NAME/KEY: misc_feature
<223> OTHER INFORMATION: 2'-Flouro-modified pyrimidines

<400> SEQUENCE: 64
ggagcucaga cuucacucgu ggaauaggaa ugacucagac guuuuuccau acgucgccgc    60
accacguacc acugucgguu ccac                                          84

<210> SEQ ID NO 65
<211> LENGTH: 82
<212> TYPE: RNA
<213> ORGANISM: Artificial Sequence
<220> FEATURE:
<223> OTHER INFORMATION: Ghrelin-binding nucleic acid
<220> FEATURE:
<221> NAME/KEY: misc_feature
<223> OTHER INFORMATION: 2'-Flouro-modified pyrimidines

<400> SEQUENCE: 65
ggagcucaga cuucacucgu gcgcuuucug uuagcugccg accgucagug cggcacgaga    60
uacguaccac ugucgguucc ac                                            82

<210> SEQ ID NO 66
<211> LENGTH: 82
<212> TYPE: RNA
<213> ORGANISM: Artificial Sequence
<220> FEATURE:
<223> OTHER INFORMATION: Ghrelin-binding nucleic acid
<220> FEATURE:
<221> NAME/KEY: misc_feature
<223> OTHER INFORMATION: 2'-Flouro-modified pyrimidines

<400> SEQUENCE: 66
ggagcucaga cuucacucgu gcgcuuucug uuagcugcug accgucagug cggcacgaga    60
uacguaccac ugucgguucc ac                                            82

<210> SEQ ID NO 67
<211> LENGTH: 81
<212> TYPE: RNA
<213> ORGANISM: Artificial Sequence
<220> FEATURE:
<223> OTHER INFORMATION: Ghrelin-binding nucleic acid
<220> FEATURE:
<221> NAME/KEY: misc_feature
<223> OTHER INFORMATION: 2'-Flouro-modified pyrimidines

<400> SEQUENCE: 67
ggagcucaga cuucacucgu gcgcuuucug uuagcuccga ccgucagugc ggcacgagau    60
acguaccacu gucgguucca c                                             81

<210> SEQ ID NO 68
<211> LENGTH: 81
<212> TYPE: RNA
<213> ORGANISM: Artificial Sequence
<220> FEATURE:
<223> OTHER INFORMATION: Ghrelin-binding nucleic acid
<220> FEATURE:
<221> NAME/KEY: misc_feature
<223> OTHER INFORMATION: 2'-Flouro-modified pyrimidines

<400> SEQUENCE: 68

-continued ggagcucaga cuucacucgu gcgcuuucug uuagcucaga ccgucagugc ggcacgagau    60
acguaccacu gucgguucca c    81

<210> SEQ ID NO 69
<211> LENGTH: 80
<212> TYPE: RNA
<213> ORGANISM: Artificial Sequence
<220> FEATURE:
<223> OTHER INFORMATION: Ghrelin-binding nucleic acid
<220> FEATURE:
<221> NAME/KEY: misc_feature
<223> OTHER INFORMATION: 2'-Flouro-modified pyrimidines

<400> SEQUENCE: 69
ggagcucaga cuucacucgu gcgcuuuugu uagcucagac cgucagugcg gcacgagaua    60
cguaccacug ucgguccac    80

<210> SEQ ID NO 70
<211> LENGTH: 77
<212> TYPE: RNA
<213> ORGANISM: Artificial Sequence
<220> FEATURE:
<223> OTHER INFORMATION: Ghrelin-binding nucleic acid
<220> FEATURE:
<221> NAME/KEY: misc_feature
<223> OTHER INFORMATION: 2'-Flouro-modified pyrimidines

<400> SEQUENCE: 70
ggagcucaga cuucacucgu gcgcuuucua gcucuuaacc gaccgugcgg cacgagacgu    60
accacugucg guccac    77

<210> SEQ ID NO 71
<211> LENGTH: 82
<212> TYPE: RNA
<213> ORGANISM: Artificial Sequence
<220> FEATURE:
<223> OTHER INFORMATION: Ghrelin-binding nucleic acid
<220> FEATURE:
<221> NAME/KEY: misc_feature
<223> OTHER INFORMATION: 2'-Flouro-modified pyrimidines

<400> SEQUENCE: 71
ggagcucaga cuucacucgu gugccgcccu uauugucagg gagcuugagc cgacacugcg    60
gacguaccac ugucgguucc ac    82

<210> SEQ ID NO 72
<211> LENGTH: 83
<212> TYPE: RNA
<213> ORGANISM: Artificial Sequence
<220> FEATURE:
<223> OTHER INFORMATION: Ghrelin-binding nucleic acid
<220> FEATURE:
<221> NAME/KEY: misc_feature
<223> OTHER INFORMATION: 2'-Flouro-modified pyrimidines

<400> SEQUENCE: 72
ggagcucaga cuucacucgu ggaauaggaa ugacucagac guuucucaua cgucgccgca    60
ccacguacca cugucgguuc cac    83

<210> SEQ ID NO 73
<211> LENGTH: 83
<212> TYPE: RNA
<213> ORGANISM: Artificial Sequence
<220> FEATURE:
<223> OTHER INFORMATION: Ghrelin-binding nucleic acid

```
<220> FEATURE:
<221> NAME/KEY: misc_feature
<223> OTHER INFORMATION: 2'-Flouro-modified pyrimidines

<400> SEQUENCE: 73
ggagcucaga cuucacucgu ggaauaggaa ugacucagac guuucucaaa cgucgccgca      60
ccacguacca cgucgguuc cac                                              83

<210> SEQ ID NO 74
<211> LENGTH: 82
<212> TYPE: RNA
<213> ORGANISM: Artificial Sequence
<220> FEATURE:
<223> OTHER INFORMATION: Ghrelin-binding nucleic acid
<220> FEATURE:
<221> NAME/KEY: misc_feature
<223> OTHER INFORMATION: 2'-Flouro-modified pyrimidines

<400> SEQUENCE: 74
ggagcucaga cuucacucgu ggaauaggaa ugacucagac guuccauac gucgccgcac       60 cacguaccac gucgguucc ac                                               82

<210> SEQ ID NO 75
<211> LENGTH: 79
<212> TYPE: RNA
<213> ORGANISM: Artificial Sequence
<220> FEATURE:
<223> OTHER INFORMATION: Ghrelin-binding nucleic acid
<220> FEATURE:
<221> NAME/KEY: misc_feature
<223> OTHER INFORMATION: 2'-Flouro-modified pyrimidines

<400> SEQUENCE: 75
ggagcucaga cuucacucgu ggaauaggaa ugacucagac guuucauguc gccgcaccac      60
guaccacugu cgguuccac                                                  79

<210> SEQ ID NO 76
<211> LENGTH: 81
<212> TYPE: RNA
<213> ORGANISM: Artificial Sequence
<220> FEATURE:
<223> OTHER INFORMATION: Ghrelin-binding nucleic acid
<220> FEATURE:
<221> NAME/KEY: misc_feature
<223> OTHER INFORMATION: 2'-Flouro-modified pyrimidines

<400> SEQUENCE: 76
ggagcucaga cuucacucgu ggaauaggaa ugacucagac guuucauacg ucgccgcacc      60
acguaccacu gucgguucca c                                               81

<210> SEQ ID NO 77
<211> LENGTH: 81
<212> TYPE: RNA
<213> ORGANISM: Artificial Sequence
<220> FEATURE:
<223> OTHER INFORMATION: Ghrelin-binding nucleic acid
<220> FEATURE:
<221> NAME/KEY: misc_feature
<223> OTHER INFORMATION: 2'-Flouro-modified pyrimidines

<400> SEQUENCE: 77
ggagcucaga cuucacucgu ggaauaggaa ugacucagac guuucauacg ucgccgcacc      60
acguaccacu gucgguucca c                                               81
```

```
<210> SEQ ID NO 78
<211> LENGTH: 80
<212> TYPE: RNA
<213> ORGANISM: Artificial Sequence
<220> FEATURE:
<223> OTHER INFORMATION: Ghrelin-binding nucleic acid
<220> FEATURE:
<221> NAME/KEY: misc_feature
<223> OTHER INFORMATION: 2'-Flouro-modified pyrimidines

<400> SEQUENCE: 78
ggagcucaga cuucacucgu ggaauaggaa ugacucagac guccauacgu cgccgcacca    60
cguaccacug ucgguuccac                                                80

<210> SEQ ID NO 79
<211> LENGTH: 82
<212> TYPE: RNA
<213> ORGANISM: Artificial Sequence
<220> FEATURE:
<223> OTHER INFORMATION: Ghrelin-binding nucleic acid
<220> FEATURE:
<221> NAME/KEY: misc_feature
<223> OTHER INFORMATION: 2'-Flouro-modified pyrimidines

<400> SEQUENCE: 79
ggagcucaga cuucacucgu ggaauaggaa ugacucagac cuuccauag gucgccgcac    60 cacguaccac ugucgguucc ac                                             82

<210> SEQ ID NO 80
<211> LENGTH: 83
<212> TYPE: RNA
<213> ORGANISM: Artificial Sequence
<220> FEATURE:
<223> OTHER INFORMATION: Ghrelin-binding nucleic acid
<220> FEATURE:
<221> NAME/KEY: misc_feature
<223> OTHER INFORMATION: 2'-Flouro-modified pyrimidines

<400> SEQUENCE: 80
ggagcucaga cuucacucgu ggaauaggaa ugacucagac cuuucucaua ggucgccgca    60
ccacguacca cugucgguuc cac                                            83

<210> SEQ ID NO 81
<211> LENGTH: 84
<212> TYPE: RNA
<213> ORGANISM: Artificial Sequence
<220> FEATURE:
<223> OTHER INFORMATION: Ghrelin-binding nucleic acid
<220> FEATURE:
<221> NAME/KEY: misc_feature
<223> OTHER INFORMATION: 2'-Flouro-modified pyrimidines

<400> SEQUENCE: 81
ggagcucaga cuucacucgu ggaauaggaa ugacucagac guuucuccau acgucgccgc    60
accacguacc acugucgguu ccac                                           84

<210> SEQ ID NO 82
<211> LENGTH: 84
<212> TYPE: RNA
<213> ORGANISM: Artificial Sequence
<220> FEATURE:
<223> OTHER INFORMATION: Ghrelin-binding nucleic acid
<220> FEATURE:
<221> NAME/KEY: misc_feature
<223> OTHER INFORMATION: 2'-Flouro-modified pyrimidines

<400> SEQUENCE: 82
```
ggagcucaga cuucacucgu ggaauaggaa ugacucaggc cuucuucau aggucgccgc    60 accacguacc acugucgguu ccac    84

<210> SEQ ID NO 83
<211> LENGTH: 82
<212> TYPE: RNA
<213> ORGANISM: Artificial Sequence
<220> FEATURE:
<223> OTHER INFORMATION: Ghrelin-binding nucleic acid
<220> FEATURE:
<221> NAME/KEY: misc_feature
<223> OTHER INFORMATION: 2'-Flouro-modified pyrimidines

<400> SEQUENCE: 83
ggagcucaga cuucacucgu ggaauaggaa ugacccagac guuucauac gucgccgcac    60 cacguaccac ugucgguucc ac    82

<210> SEQ ID NO 84
<211> LENGTH: 83
<212> TYPE: RNA
<213> ORGANISM: Artificial Sequence
<220> FEATURE:
<223> OTHER INFORMATION: Ghrelin-binding nucleic acid
<220> FEATURE:
<221> NAME/KEY: misc_feature
<223> OTHER INFORMATION: 2'-Flouro-modified pyrimidines

<400> SEQUENCE: 84
ggagcucaga cuucacucgu ggaauaggaa ugacucagac cuuuucaua ggucgccgca    60 ccacguacca cugucgguuc cac    83

<210> SEQ ID NO 85
<211> LENGTH: 83
<212> TYPE: RNA
<213> ORGANISM: Artificial Sequence
<220> FEATURE:
<223> OTHER INFORMATION: Ghrelin-binding nucleic acid
<220> FEATURE:
<221> NAME/KEY: misc_feature
<223> OTHER INFORMATION: 2'-Flouro-modified pyrimidines

<400> SEQUENCE: 85
ggagcucaga cuucacucgu ggaauaggaa ugacucagac cuuuucaua ggucgccgca    60 ccacguacca cugucgguuc cac    83

<210> SEQ ID NO 86
<211> LENGTH: 82
<212> TYPE: RNA
<213> ORGANISM: Artificial Sequence
<220> FEATURE:
<223> OTHER INFORMATION: Ghrelin-binding nucleic acid
<220> FEATURE:
<221> NAME/KEY: misc_feature
<223> OTHER INFORMATION: 2'-Flouro-modified pyrimidines

<400> SEQUENCE: 86
ggagcucaga cuucacucgu gcgcuuucug uuagcugccg accgucagug cggcacgaga    60
uacguaccac ugucgguucc ac    82

<210> SEQ ID NO 87
<211> LENGTH: 49
<212> TYPE: RNA
<213> ORGANISM: Artificial Sequence
<220> FEATURE:

-continued

<223> OTHER INFORMATION: Ghrelin-binding nucleic acid

<400> SEQUENCE: 87
ggugggugag gcaguaaugu aaguccgaag guaaccaauc cuacccacc          49

<210> SEQ ID NO 88
<211> LENGTH: 43
<212> TYPE: RNA
<213> ORGANISM: Artificial Sequence
<220> FEATURE:
<223> OTHER INFORMATION: Ghrelin-binding nucleic acid

<400> SEQUENCE: 88
gggugaggca guaauguaag uccgaaggua accaauccua ccc                43

<210> SEQ ID NO 89
<211> LENGTH: 43
<212> TYPE: RNA
<213> ORGANISM: Artificial Sequence
<220> FEATURE:
<223> OTHER INFORMATION: Ghrelin-binding nucleic acid

<400> SEQUENCE: 89
gggugaggca gacacguaag accgaaggua accaauccua ccc                43

<210> SEQ ID NO 90
<211> LENGTH: 49
<212> TYPE: RNA
<213> ORGANISM: Artificial Sequence
<220> FEATURE:
<223> OTHER INFORMATION: Ghrelin-binding nucleic acid

<400> SEQUENCE: 90
ggugggugag gcagcuaugu aaguccgaag guaaccaauc cuacccacc          49

<210> SEQ ID NO 91
<211> LENGTH: 43
<212> TYPE: RNA
<213> ORGANISM: Artificial Sequence
<220> FEATURE:
<223> OTHER INFORMATION: Ghrelin-binding nucleic acid

<400> SEQUENCE: 91
gggugaggca gcuauguaag uccgaaggua accaauccua ccc                43

<210> SEQ ID NO 92
<211> LENGTH: 43
<212> TYPE: RNA
<213> ORGANISM: Artificial Sequence
<220> FEATURE:
<223> OTHER INFORMATION: Ghrelin-binding nucleic acid

<400> SEQUENCE: 92
gggugaggca ugcaaguaag uccgaaggua cccaauccua ccc                43

<210> SEQ ID NO 93
<211> LENGTH: 43
<212> TYPE: RNA
<213> ORGANISM: Artificial Sequence
<220> FEATURE:
<223> OTHER INFORMATION: Ghrelin-binding nucleic acid

<400> SEQUENCE: 93
gggugaggca guuauguaag accgaaggua cccaauccua ccc                43

```
<210> SEQ ID NO 94
<211> LENGTH: 49
<212> TYPE: RNA
<213> ORGANISM: Artificial Sequence
<220> FEATURE:
<223> OTHER INFORMATION: Ghrelin-binding nucleic acid

<400> SEQUENCE: 94
ggugggugag gcacacccau aaguccgaag guaaccaauc cuacccacc          49

<210> SEQ ID NO 95
<211> LENGTH: 43
<212> TYPE: RNA
<213> ORGANISM: Artificial Sequence
<220> FEATURE:
<223> OTHER INFORMATION: Ghrelin-binding nucleic acid

<400> SEQUENCE: 95
gggugaggca cacccauaag uccgaaggua accaauccua ccc                43

<210> SEQ ID NO 96
<211> LENGTH: 43
<212> TYPE: RNA
<213> ORGANISM: Artificial Sequence
<220> FEATURE:
<223> OTHER INFORMATION: Ghrelin-binding nucleic acid

<400> SEQUENCE: 96
gggugaggca auccgauaag uccgaaggua accaauccua ccc                43

<210> SEQ ID NO 97
<211> LENGTH: 43
<212> TYPE: RNA
<213> ORGANISM: Artificial Sequence
<220> FEATURE:
<223> OTHER INFORMATION: Ghrelin-binding nucleic acid

<400> SEQUENCE: 97
gggugaggca guaaaguaag accgaaggua accaauccua ccc                43

<210> SEQ ID NO 98
<211> LENGTH: 43
<212> TYPE: RNA
<213> ORGANISM: Artificial Sequence
<220> FEATURE:
<223> OTHER INFORMATION: Ghrelin-binding nucleic acid

<400> SEQUENCE: 98
gggugaggca guucaguaag uccgaaggua accaauccua ccc                43

<210> SEQ ID NO 99
<211> LENGTH: 43
<212> TYPE: RNA
<213> ORGANISM: Artificial Sequence
<220> FEATURE:
<223> OTHER INFORMATION: Ghrelin-binding nucleic acid

<400> SEQUENCE: 99
gggugaggcg uacaaauaag uccgaaggua accaguccua ccc                43

<210> SEQ ID NO 100
<211> LENGTH: 43
<212> TYPE: RNA
<213> ORGANISM: Artificial Sequence
<220> FEATURE:
<223> OTHER INFORMATION: Ghrelin-binding nucleic acid
```

<400> SEQUENCE: 100
gggugaggca cacaaauaag uccgaaggua uccaguccua ccc 43

<210> SEQ ID NO 101
<211> LENGTH: 49
<212> TYPE: RNA
<213> ORGANISM: Artificial Sequence
<220> FEATURE:
<223> OTHER INFORMATION: Ghrelin-binding nucleic acid
<220> FEATURE:
<221> NAME/KEY: misc_feature
<222> LOCATION: (1)..(1)
<223> OTHER INFORMATION: Primer

<400> SEQUENCE: 101
ggugggugag gcacacccgu aaguccgaag guaaccaauc cuacccacc 49

<210> SEQ ID NO 102
<211> LENGTH: 49
<212> TYPE: RNA
<213> ORGANISM: Artificial Sequence
<220> FEATURE:
<223> OTHER INFORMATION: Ghrelin-binding nucleic acid

<400> SEQUENCE: 102
ggugggugag gcauuaacgu aagaccgaag guaaccaauc cuacccacc 49

<210> SEQ ID NO 103
<211> LENGTH: 49
<212> TYPE: RNA
<213> ORGANISM: Artificial Sequence
<220> FEATURE:
<223> OTHER INFORMATION: Ghrelin-binding nucleic acid

<400> SEQUENCE: 103
ggugggugag gcaguuaugu aagaccgaag guacccaauc cuacccacc 49

<210> SEQ ID NO 104
<211> LENGTH: 49
<212> TYPE: RNA
<213> ORGANISM: Artificial Sequence
<220> FEATURE:
<223> OTHER INFORMATION: Ghrelin-binding nucleic acid

<400> SEQUENCE: 104
ggugggugag gcagucuugu aaguccgaag guaaccaauc cuacccacc 49

<210> SEQ ID NO 105
<211> LENGTH: 49
<212> TYPE: RNA
<213> ORGANISM: Artificial Sequence
<220> FEATURE:
<223> OTHER INFORMATION: Ghrelin-binding nucleic acid

<400> SEQUENCE: 105
ggugggugag gcauaaacgu aagaccgaag guaaccaauc cuacccgcc 49

<210> SEQ ID NO 106
<211> LENGTH: 49
<212> TYPE: RNA
<213> ORGANISM: Artificial Sequence
<220> FEATURE:
<223> OTHER INFORMATION: Ghrelin-binding nucleic acid

<400> SEQUENCE: 106
ggugggugag gcaaugucgu aaguccgaag guaaccaauc cuacccacc 49

<210> SEQ ID NO 107
<211> LENGTH: 49
<212> TYPE: RNA
<213> ORGANISM: Artificial Sequence
<220> FEATURE:
<223> OTHER INFORMATION: Ghrelin-binding nucleic acid

<400> SEQUENCE: 107
ggugggugag gcacuaaaau aagaccgaag guaaccaauc cuacccacc        49

<210> SEQ ID NO 108
<211> LENGTH: 49
<212> TYPE: RNA
<213> ORGANISM: Artificial Sequence
<220> FEATURE:
<223> OTHER INFORMATION: Ghrelin-binding nucleic acid

<400> SEQUENCE: 108
ggugggugag gcacgcaaau aagaccgaag guaaccaauc cuacccacc        49

<210> SEQ ID NO 109
<211> LENGTH: 49
<212> TYPE: RNA
<213> ORGANISM: Artificial Sequence
<220> FEATURE:
<223> OTHER INFORMATION: Ghrelin-binding nucleic acid

<400> SEQUENCE: 109
ggugggugag gcguucacau aaguccgaag guaaccaauc cuacccacc        49

<210> SEQ ID NO 110
<211> LENGTH: 49
<212> TYPE: RNA
<213> ORGANISM: Artificial Sequence
<220> FEATURE:
<223> OTHER INFORMATION: Ghrelin-binding nucleic acid

<400> SEQUENCE: 110
ggugggugag gcaguaaugu aaguccgaag guaaccaauc cuacccacc        49

<210> SEQ ID NO 111
<211> LENGTH: 49
<212> TYPE: RNA
<213> ORGANISM: Artificial Sequence
<220> FEATURE:
<223> OTHER INFORMATION: Ghrelin-binding nucleic acid

<400> SEQUENCE: 111
ggugggugag gcaauuaagu aaguccgaag guaaccaguc cuacccacc        49

<210> SEQ ID NO 112
<211> LENGTH: 49
<212> TYPE: RNA
<213> ORGANISM: Artificial Sequence
<220> FEATURE:
<223> OTHER INFORMATION: Ghrelin-binding nucleic acid

<400> SEQUENCE: 112
ggugggugag gcaugcaagu aaguccgaag guacccaauc cuacccacc        49

<210> SEQ ID NO 113
<211> LENGTH: 49
<212> TYPE: RNA
<213> ORGANISM: Artificial Sequence
<220> FEATURE:

-continued

<223> OTHER INFORMATION: Ghrelin-binding nucleic acid

<400> SEQUENCE: 113
ggugggugag gcauuaacgu aaguccgaag guaaccaauc cuaccuacc            49

<210> SEQ ID NO 114
<211> LENGTH: 49
<212> TYPE: RNA
<213> ORGANISM: Artificial Sequence
<220> FEATURE:
<223> OTHER INFORMATION: Ghrelin-binding nucleic acid

<400> SEQUENCE: 114
ggugggugag gcacacaaau aaguccgaag guauccaguc cuacccacc            49

<210> SEQ ID NO 115
<211> LENGTH: 49
<212> TYPE: RNA
<213> ORGANISM: Artificial Sequence
<220> FEATURE:
<223> OTHER INFORMATION: Ghrelin-binding nucleic acid

<400> SEQUENCE: 115
ggugggugag gcagacacgu aagaccgaag guaaccaauc cuacccacc            49

<210> SEQ ID NO 116
<211> LENGTH: 49
<212> TYPE: RNA
<213> ORGANISM: Artificial Sequence
<220> FEATURE:
<223> OTHER INFORMATION: Ghrelin-binding nucleic acid

<400> SEQUENCE: 116
ggugggugag gcacacccau aaguccgaag guaaccaauc cuacccacc            49

<210> SEQ ID NO 117
<211> LENGTH: 49
<212> TYPE: RNA
<213> ORGANISM: Artificial Sequence
<220> FEATURE:
<223> OTHER INFORMATION: Ghrelin-binding nucleic acid

<400> SEQUENCE: 117
ggugggugag gcguacaaau aaguccgaag guaaccaguc cuaccuacc            49

<210> SEQ ID NO 118
<211> LENGTH: 49
<212> TYPE: RNA
<213> ORGANISM: Artificial Sequence
<220> FEATURE:
<223> OTHER INFORMATION: Ghrelin-binding nucleic acid

<400> SEQUENCE: 118
ggugggugag gcaauaaagu aagaccgaag guaaccaauc cuacccacc            49

<210> SEQ ID NO 119
<211> LENGTH: 49
<212> TYPE: RNA
<213> ORGANISM: Artificial Sequence
<220> FEATURE:
<223> OTHER INFORMATION: Ghrelin-binding nucleic acid

<400> SEQUENCE: 119
ggugggugag gcagcuaugu aaguccgaag guaaccaauc cuacccacc            49

```
<210> SEQ ID NO 120
<211> LENGTH: 49
<212> TYPE: RNA
<213> ORGANISM: Artificial Sequence
<220> FEATURE:
<223> OTHER INFORMATION: Ghrelin-binding nucleic acid

<400> SEQUENCE: 120
ggugggugag gcaauccgau aaguccgaag guaaccaauc cuacccacc          49

<210> SEQ ID NO 121
<211> LENGTH: 49
<212> TYPE: RNA
<213> ORGANISM: Artificial Sequence
<220> FEATURE:
<223> OTHER INFORMATION: Ghrelin-binding nucleic acid

<400> SEQUENCE: 121
ggugggugag gcaguaaagu aagaccgaag guaaccaauc cuacccacc          49

<210> SEQ ID NO 122
<211> LENGTH: 49
<212> TYPE: RNA
<213> ORGANISM: Artificial Sequence
<220> FEATURE:
<223> OTHER INFORMATION: Ghrelin-binding nucleic acid

<400> SEQUENCE: 122
ggugggugag gcauacaagu aaguccgaag guaaccaauc cuacccacc          49

<210> SEQ ID NO 123
<211> LENGTH: 49
<212> TYPE: RNA
<213> ORGANISM: Artificial Sequence
<220> FEATURE:
<223> OTHER INFORMATION: Ghrelin-binding nucleic acid

<400> SEQUENCE: 123
ggugggugag gcaguucagu aaguccgaag guaaccaauc cuacccacc          49

<210> SEQ ID NO 124
<211> LENGTH: 49
<212> TYPE: RNA
<213> ORGANISM: Artificial Sequence
<220> FEATURE:
<223> OTHER INFORMATION: Ghrelin-binding nucleic acid

<400> SEQUENCE: 124
ggugggugag gcaguaaaau aaguccgaag guauccaauc cuacccacc          49

<210> SEQ ID NO 125
<211> LENGTH: 60
<212> TYPE: RNA
<213> ORGANISM: Artificial Sequence
<220> FEATURE:
<223> OTHER INFORMATION: Ghrelin-binding nucleic acid

<400> SEQUENCE: 125
ggugggugag gcaaucuggu gaggcagaug uaagaccgaa gguaaccaau ccuacccacc     60

<210> SEQ ID NO 126
<211> LENGTH: 17
<212> TYPE: RNA
<213> ORGANISM: Artificial Sequence
<220> FEATURE:
<223> OTHER INFORMATION: Ghrelin-binding nucleic acid
```

```
<400> SEQUENCE: 126
ggagcucaga cuuagca                                                    17

<210> SEQ ID NO 127
<211> LENGTH: 18
<212> TYPE: RNA
<213> ORGANISM: Artificial Sequence
<220> FEATURE:
<223> OTHER INFORMATION: Ghrelin-binding nucleic acid

<400> SEQUENCE: 127
aucgaguguc gguuccac                                                   18

<210> SEQ ID NO 128
<211> LENGTH: 103
<212> TYPE: DNA
<213> ORGANISM: Artificial Sequence
<220> FEATURE:
<223> OTHER INFORMATION: Ghrelin-binding nucleic acid

<400> SEQUENCE: 128
tctaatacga ctcactatag gagctcagac ttagcaggtg ggtgaggcaa aaacgtaaga     60
ccgaaggtaa ccattcctac ccaccatcga gtgtcggttc cac                      103

<210> SEQ ID NO 129
<211> LENGTH: 38
<212> TYPE: DNA
<213> ORGANISM: Artificial Sequence
<220> FEATURE:
<223> OTHER INFORMATION: Ghrelin-binding nucleic acid

<400> SEQUENCE: 129
tctaatacga ctcactatag gagctcagac ttagcagg                             38

<210> SEQ ID NO 130
<211> LENGTH: 20
<212> TYPE: DNA
<213> ORGANISM: Artificial Sequence
<220> FEATURE:
<223> OTHER INFORMATION: Ghrelin-binding nucleic acid

<400> SEQUENCE: 130
gtggaaccga cactcgatgg                                                 20
```

GHRELIN BINDING NUCLEIC ACIDS

The present invention is generally related to an antagonist to ghrelin, nucleic acids binding to ghrelin, use of such nucleic acids, composition and complex comprising such nucleic acids, a method for the generation and/or identification of a nucleic acid binding to a target molecule, a method for the generation of an L-nucleic acid binding to a target molecule and a method for the screening of a ghrelin antagonist.

Ghrelin was identified as the natural ligand of the growth hormone secretagogue receptor 1a (GHSR1a). The receptor is most abundant in the pituitary gland and in hypothalamic parts of the brain, but can also be detected in other tissues at low concentrations. Since the late 70ies synthetic peptides and other compounds, named secretagogues had been shown to stimulate the release of growth hormone. However, the natural ligand responsible for the release of growth hormone remained unknown until the discovery of ghrelin in 1999. Ghrelin is a highly basic 28 amino acid peptide hormone with an octanoyl acid side chain at the third amino acid of its N-terminus (serine 3). This unusual modification is required for the interaction at the GHS-receptor and its activity. The amino-acid sequence of the purified rat ghrelin was determined by a protein sequencer to be GSSFLSPE-HQKAQQRKESKKPPAKLQPR (SEQ ID NO:1).

Ghrelin has been shown to mediate physiological functions pertinent to an anabolic state. While it directly stimulates the release of growth hormone (GH) from the pituitary gland, experiments in rodents also showed ghrelin to induce feeding in a GH-independent fashion by acting upon hypothalamic neurons. Interestingly, the primary site of ghrelin production is in oxyntic glands in the stomach, suggesting that it serves as a hormonal link between stomach, pituitary gland and hypothalamus. The observation that ghrelin administration in rats resulted in weight gain as a consequence of changes in energy intake and/or fuel utilization is in support of such a role. Moreover, systemic ghrelin administration in humans cause sensations of hunger in the test subjects and induce overeating. Based on these findings ghrelin is thought to have a crucial role in the regulation of appetite and body weight, serving as an acute as well as a chronic signal of an underfed state. Additional support for this hypothesis comes from observations that ghrelin levels as well as appetite are reduced in individuals following gastric bypass, contributing at least in part to the efficiency of the procedure in effecting weight loss. Clinical data from patients with Prader-Willi syndrome also suggest that the hyperphagia and obesity associated with the disease are a consequence of tremendous hyperghrelinemia. Moreover, ghrelin was found to induce hyperglycemia and inhibition of insulin release, indicating an involvement in glucose metabolism. Beside these functions in energy metabolism, ghrelin has also been implicated in a number of other processes. It was found to be expressed in a number of neuroendocrine tumors and to stimulate, besides GH release from the pituitary, the release of ACTH, PRL, and cortisol. Single injections of ghrelin into healthy individuals were found to increase cardiac output and decrease blood pressure. Thus, ghrelin action appears to be involved in a variety of different tasks. For background information may be taken from M. Kojima, H. Hosoda, Y. Date, M. Nakazato, H. Matsu, K. Kangawa, "Ghrelin is a growth-hormone-releasing acylated peptide from stomach", Nature 402:656-60, 1999; M. Tschöp, D. L. Smiley, M. L. Heiman, "Ghrelin induces adiposity in rodents", Nature 407:908-13, 2000; A. M. Wren et al., "Ghrelin enhances appetite and increases food intake in humans", Journal of Clinical Endocrinology Metabolism 86:5992-6, 2001; M. Nakazato et al., "A role for ghrelin in the central regulation of feeding", Nature 409: 194-8, 2001; N. Nagaya, et al., Am J Physiol Regul Integr Comp Physiol. 2001 May; 280(5):R1483-7; Hemodynamic and hormonal effects of human ghrelin in healthy volunteers; Volante M, et al., J Clin Endocrinol Metab. 2002 March; 87(3):1300-8. Expression of ghrelin and of the GH secretagogue receptor by pancreatic islet cells and related endocrine tumors; Jeffery P L, et al., J Endocrinol. 2002 March; 172(3):R7-11 Expression and action of the growth hormone releasing peptide ghrelin and its receptor in prostate cancer cell lines; Egido E M, et al., Eur J Endocrinol. 2002 February; 146(2):241-4 Inhibitory effect of ghrelin on insulin and pancreatic somatostatin secretion; Broglio F, et al., J Clin Endocrinol Metab. 2001 October; 86(10):5083-6, Ghrelin, a natural GH secretagogue produced by the stomach, induces hyperglycemia and reduces insulin secretion in humans.

The problem underlying the present invention is to provide a specific antagonist to ghrelin. A further aspect of the problem underlying the present invention is to provide a specific antagonist to the growth hormone secretagogue receptor 1 a (GHSR 1a). Another aspect of the problem underlying the present invention is to provide a compound for the treatment of diseases and disorders involving ghrelin and the GHSR 1a receptor, respectively.

The problem underlying the present invention is solved in a first aspect by an antagonist of ghrelin, wherein the antagonist is a nucleic acid. In a preferred embodiment the nucleic acid is binding to ghrelin.

The problem underlying the present invention is solved in a first aspect by an antagonist of the GHSR 1a receptor system, wherein the antagonist is a nucleic acid. In a preferred embodiment the nucleic acid is binding to the ligand of the receptor and whereby the ligand is preferably ghrelin.

In an embodiment of the first and the second aspect of the present invention the nucleic acid comprises at least one L-nucleotide.

In a preferred embodiment of the first and the second aspect of the present invention the antagonist is an L-nucleic acid.

In a more preferred embodiment of the first and the second aspect of the present invention the nucleic acid is a nucleic acid as disclosed herein. Preferably the nucleic acid is a nucleic acid according to the third and fourth aspect of the present invention.

The problem underlying the present invention is solved in a third aspect by a nucleic acid binding to ghrelin. Preferably the nucleic acid is a L-nucleic acid binding to L-ghrelin.

In a preferred embodiment the L-nucleic acid is a nucleic acid as disclosed herein. Preferably, the nucleic acid is a nucleic acid according to the fourth aspect of the present invention.

The problem underlying the present invention is solved in a fourth aspect by a nucleic acid having a sequence which is selected from the group comprising the sequences according to SEQ. ID. No. 7 to SEQ. ID. No. 125.

In an embodiment the nucleic acid comprises at least one L-nucleotide.

In a preferred embodiment the nucleic acid is an L-nucleic acid.

In a further embodiment the nucleic acid is selected from the group comprising DNA, RNA and combinations thereof.

In a preferred embodiment the Kd of the nucleic acid is less than 1 µM, preferably less than 0.25 µM, more preferably less than 0.1 µM and most preferably less than 0.01 µM.

In a more preferred embodiment the Kd of the nucleic acid is more than 100 nM, preferably more than 10 nM, more preferably more than 1 nM and most preferably more than 0.05 nM.

In a further preferred embodiment the nucleic acid is of a length selected from the group comprising 15 to 150 nucleotides, 20 to 100 nucleotides, 20 to 80 nucleotides, 20 to 60 nucleotides, 20 to 50 nucleotides and 30 to 50 nucleotides.

In a still further embodiment the nucleic acid comprises a minimal binding motif.

In another preferred embodiment of the third to sixth aspect of the present invention the nucleic acid has at least a bipartite structure.

The problem underlying the present invention is solved in a fifth aspect by the use of a nucleic acid according to the present invention, preferably a nucleic acid according to the third and/or fourth aspect of the present invention, as an antagonist of ghrelin and/or the GHSR 1a receptor system.

The problem underlying the present invention is solved in a sixth aspect by a method for the generation and/or identification of a nucleic acid binding to a target molecule, preferably of a nucleic acid which specifically binds L-ghrelin, comprising the following steps:
 a) generating a heterogeneous population of nucleic acids;
 b) contacting the population of step a) with the target molecule;
 c) separating the nucleic acid(s) not interacting with the target molecule;
 d) optionally separating the nucleic acid(s) interacting with the target molecule; and
 e) optionally sequencing the nucleic acid(s) interacting with the target molecule,
 characterized in that the target molecule is ghrelin.

In an embodiment of the method subsequent to step c) a step ca) is carried out, whereby step ca) consists of amplification of the nucleic acid(s) interacting with the target molecule.

In a preferred embodiment steps b) to d) are repeated.

In a more preferred embodiment the heterogeneous population of nucleic acids comprises at least one nucleic acid according to the present invention. Preferably, the nucleic acid according to the present invention is a nucleic acid according to the third and/or fourth aspect of the present invention.

The problem underlying the present invention is solved according to a seventh aspect by a method for the generation of an L-nucleic acid binding to a target molecule in the natural configuration comprising the following steps:
 a) generating a heterogeneous population of D-nucleic acids;
 b) contacting the population of step a) with an optical antipode of the target molecule;
 c) separating the D-nucleic acid not interacting with the optical antipode of the target molecule;
 d) sequencing the D-nucleic acid interacting with the optical antipode of the target molecule; and
 e) synthesising the L-nucleic acid sequence(s) which is/are identical to the sequence of the D-nucleic acid(s) obtained in step d);
 characterised in that the target molecule is L-ghrelin and the optical antipode of the target molecule is the D-ghrelin.

In an embodiment of the method subsequent to step c) the following step is introduced:
 ca) amplifying the D-nucleic acid interacting with the optical antipode of the target molecule.

In a preferred embodiment steps b) to e) are repeated.

In a more preferred embodiment the heterogeneous population of nucleic acids comprises a nucleic acid according to the present invention. Preferably, the nucleic acid is a nucleic acid according to the third and/or fourth aspect of the present invention.

The problem underlying the present invention is solved in an eighth aspect by the use of a nucleic acid according to the present invention and/or of an antagonist according to the present invention 5 for the manufacture of a medicament. Alternatively, the aforementioned use is for the manufacture of a cosmetic product. In a preferred embodiment the nucleic acid according to the present invention is a nucleic acid according to the third and/or fourth aspect of the present invention. In a further preferred embodiment the antagonist according to the present invention is an antagonist according to the first and/or second aspect of the present invention.

In a further embodiment the medicament is for the treatment of a disease or disorder selected from the group comprising obesity, the regulation of energy balance, appetite and body weight, eating disorders, diabetes, glucose metabolism, tumour, blood pressure and/or cardiovascular diseases. In a further embodiment the cosmetic product is for appetite and body weight control, and/or for obesity.

In a ninth aspect the problem underlying the present invention is solved by a composition, preferably a pharmaceutical composition, comprising a nucleic acid according to the present invention and/or an antagonist according to the present invention, and a pharmaceutical acceptable carrier. In a preferred embodiment the nucleic acid according to the present invention is a nucleic acid according to the third and/or fourth aspect of the present invention. In a further preferred embodiment the antagonist according to the present invention is the antagonist according to the first and second aspect of the present invention.

In a tenth aspect the problem underlying the present invention is solved by a complex comprising ghrelin and any of the nucleic acids according to the present invention. In a preferred embodiment the complex is a crystalline complex. In a still further embodiment the nucleic acid according to the present invention is a nucleic acid according to the third and/or fourth aspect of the present invention.

In an eleventh aspect the problem underlying the present invention is solved by the use of any of the nucleic acids according to the present invention and/or of an antagonist according to the present invention for the detection of ghrelin. In a preferred embodiment the nucleic acid according to the present invention is a nucleic acid according to the third and/or fourth aspect of the present invention. In a further preferred embodiment the antagonist according to the present invention is the antagonist according to the first and second aspect of the present invention.

In a twelfth aspect the problem underlying the present invention is solved by a method for the screening of a ghrelin antagonist comprising the following steps:
 providing a candidate ghrelin antagonist,
 providing a nucleic acid according to the present invention and/or an antagonist according to the present invention,
 providing a test system providing a signal in the presence of a ghrelin antagonist, and
 determining whether the candidate ghrelin antagonist is a ghrelin antagonist.

In a preferred embodiment the nucleic acid according to the present invention is a nucleic acid according to the third and/or fourth aspect of the present invention. In a further preferred embodiment the antagonist according to the present invention is the antagonist according to the first and second aspect of the present invention.

In a thirteenth aspect the problem underlying the present invention is solved by a kit for the detection of ghrelin, comprising a nucleic acid according to the present invention and/or an antagonist according to the present invention. Preferably, the nucleic acid according to the present invention is a nucleic acid according to the third and/or fourth aspect of the present invention. In a further preferred embodiment the antagonist according to the present invention is the antagonist according to the first and second aspect of the present invention.

Ghrelin is a basic peptide having the amino acid sequence according to SEQ. ID. No. 1, and is modified with a fatty acid side chain. The calculated pI of ghrelin is 11.09. As used herein the term ghrelin refers to any ghrelin including, but not limited to, mammalian ghrelin. Preferably, the mammalian ghrelin is selected from the group comprising mice, rat, rabbit, hamster and human ghrelin. Most preferably the ghrelin is human ghrelin.

The present invention is based on the surprising finding that it is possible to generate nucleic acids binding specifically and with a high affinity to ghrelin. This finding is insofar surprising as Eaton et al. (Eaton, B. E.; Gold, L.; Hicke, B. J.; Janjic, N.; Jucker, F. M.; Sebesta, D. P.; Tarasow, T. M.; Willis, M. C.; Zichi, D. A.; Bioorganic & Medicinal Chemistry, Vol 5, No. 6; pp 1087-1096, 1997) observed that the generation of aptamers, i.e. nucleic acids binding to a target molecule, directed to a basic protein is in general very difficult because this kind of target produces a high but non-specific signal-to-noise ratio. This high signal-to-noise ratio results from the high non-specific affinity shown by nucleic acids for basic targets.

The features of the nucleic acid according to the present invention as described herein can be realised in any aspect of the present invention where the nucleic acid is used, either alone or in any combination.

The nucleic acids according to the present invention shall also comprise nucleic acids which are essentially homologous to the particular sequences disclosed herein. The term substantially homologous shall be understood such as the homology is at least 75%, preferably 85%, more preferably 90% and most preferably more that 95%, 96%, 97%, 98% or 99%.

The term inventive nucleic acid or nucleic acid according to the present invention shall also comprise those nucleic acids comprising part of the nucleic acids sequences disclosed herein, preferably to the extent that said parts are involved in the binding to ghrelin. Such a nucleic acid may be derived from the ones disclosed herein, e.g., by truncation. Truncation may be related to either or both of the ends of the nucleic acids as disclosed herein. Also, truncation may be related to the inner sequence of nucleotides, i.e. it may be related to the nucleotide(s) between the 5' and the 3' terminal nucleotide, respectively. Moreover, truncation shall comprise the deletion of as little as a single nucleotide from the sequence of the nucleic acids disclosed herein. Truncation may also be related to more than one stretch of the inventive nucleic acid(s), whereby the stretch can be as little as one nucleotide long. Examples for the truncation of the inventive nucleic acids are described in the example part of this description.

The nucleic acids according to the present invention may be either D-nucleic acids or L-nucleic acids. Preferably, the inventive nucleic acids are L-nucleic acids. In addition it is possible that one or several parts of the nucleic acid are present as D-nucleic acids or at least one or several parts of the nucleic acids are L-nucleic acids. The term "part" of the nucleic acids shall mean as little as one nucleotide. Such nucleic acids are generally referred to herein as D- and L-nucleic acids, respectively.

It is also within the present invention that the nucleic acids according to the present invention are part of a longer nucleic acid whereby this longer nucleic acid comprises several parts whereby at least one part is a nucleic acid, or a part thereof, according to the present invention. The other part of these longer nucleic acids can be either a D-nucleic acid or L-nucleic acid. Any combination may be used in connection with the present invention. These other part(s) of the longer nucleic acid can exhibit a function which is different from binding. One possible function is to allow interaction with other molecules such as, e.g., for immobilization, cross-linking, detection or amplification.

L-nucleic acids as used herein are nucleic acids consisting of L-nucleotides, preferably consisting completely of L-nucleotides.

D-nucleic acids as used herein are nucleic acids consisting of D-nucleotides, preferably consisting completely of D-nucleotides.

Irrespective of whether the inventive nucleic acid consists of D-nucleotides, L-nucleotides or a combination of both with the combination being e.g. a random combination or a defined sequence of stretches consisting of at least one L-nucleotide and at least one D-nucleic acid, the nucleic acid may consist of desoxyribonucleotide(s), ribonucleotide(s) or combinations thereof.

Designing the inventive nucleic acids as L-nucleic acid is advantageous for several reasons. L-nucleic acids are enantiomers of naturally occurring nucleic acids. D-nucleic acids, however, are not very stable in aqueous solutions and particularly in biological systems or biological samples due to the widespread presence of nucleases. Naturally occurring nucleases, particularly nucleases from animal cells are not capable of degrading L-nucleic acids. Because of this the biological half-life of the L-nucleic acid is significantly increased in such a system, including the animal and human body. Due to the lacking degradability of L-nucleic acid no nuclease degradation products are generated and thus no side effects arising therefrom observed. This aspect delimits the L-nucleic acid of factually all other compound which are used in the therapy of diseases and/or disorders involving the presence of ghrelin.

It is also within the present invention that the inventive nucleic acids, regardless whether they are present as D-nucleic acids, L-nucleic acids or D,L-nucleic acids or whether they are DNA or RNA, may be present single stranded or double stranded nucleic acids. Typically, the inventive nucleic acids are single stranded nucleic acids which exhibit defined secondary structures due to the primary sequence and may thus also form tertiary structures. The inventive nucleic acids, however, may also be double stranded in the meaning that two strands which are complementary to each other are hybridised to each other. This confers stability to the nucleic acid which will be advantageous if the nucleic acid is present in the naturally occurring D-form rather than the L-form.

The inventive nucleic acids may be modified. Such modifications may be related to the single nucleotide of the nucleic acid and are well known in the art. Examples for such modification are described in, among others, Kusser, W.(2000) J Biotechnol, 74: 27-38; Aurup, H. et al. (1994) *Nucleic Acids Res*, 22, 20-4; Cummins, L. L. et al, (1995) *Nucleic Acids Res*, 23, 2019-24; Eaton, B. E. et al. (1995) *Chem Biol*, 2, 633-8; Green, L. S. et al., (1995) *Chem Biol*, 2, 683-95; Kawasaki, A.

M. et al., (1993) *J Med Chem,* 36, 831-41; Lesnik, E. A. et al., (1993) *Biochemistry,* 32, 7832-8; Miller, L. E. et al., (1993) *J Physiol,* 469, 213-43.

The nucleic acids according to the present invention may be a multipartite nucleic acid. A multipartite nucleic acid as used herein, is a nucleic acid which consists of at least two nucleic acid strands. These at least two nucleic acid strands form a functional unit whereby the functional unit is a ligand to a target molecule. The at least two nucleic acid strands may be derived from any of the inventive nucleic acids by either cleaving the nucleic acid to generate two strands or by synthesising one nucleic acid corresponding to a first part of the inventive, i.e. overall nucleic acid and another nucleic acid corresponding to the second part of the overall nucleic acid. It is to be acknowledged that both the cleavage and the synthesis may be applied to generate a multipartite nucleic acid where there are more than two strands as exemplified above. In other words, the at least two nucleic acid strands are typically different from two strands being complementary and hybridising to each other although a certain extent of complementarity between the various nucleic acid parts may exist.

A possibility to determine the binding constant is the use of the so called biacore device, which is also known to the one skilled in the art. Affinity as used herein was also measured by the use of "bead assays" as described in the examples. An appropriate measure in order to express the intensity of the binding between the nucleic acid according to the target which is in the present case ghrelin, is the so-called Kd value which as such as well the method for its determination are known to the one skilled in the art.

The nucleic acids according to the present invention are characterized by a certain Kd value. Preferably, the Kd value shown by the nucleic acids according to the present invention is below 1 µM. A Kd value of about 1 µM is said to be characteristic for a non-specific binding of a nucleic acid to a target. As will be acknowledged by the ones in the art, the Kd value of a group of compounds such as the nucleic acids according to the present invention are within a certain range. The above-mentioned Kd of about 1 µM is a preferred upper limit for the Kd value. The preferred lower limit for the Kd of target binding nucleic acids can be about 10 picomolar or higher. It is within the present invention that the Kd values of individual nucleic acids binding to ghrelin is preferably within this range. Preferred ranges can be defined by choosing any first number within this range and any second number within this range. Preferred upper values are 0.25 µM, 0.1 µM and 0.01 µM, preferred lower values are 100 nM, 10 nM, 1 nm and 0.05 nM.

The nucleic acid molecules according to the present invention may have any length provided that they are still able to bind to the target molecule. It will be acknowledged in the art that there are preferred lengths of the nucleic acids according to the present inventions. Typically, the length is between 15 and 120 nucleotides. It will be acknowledged by the ones skilled in the art that any integer between 15 and 120 is a possible length for the nucleic acids according to the present invention. More preferred ranges for the length of the nucleic acids according to the present invention are lengths of about 20 to 100 nucleotides, about 20 to 80 nucleotides, about 20 to 60 nucleotides, about 20 to 50 nucleotides and about 30 to 50 nucleotides.

The inventive method disclosed herein for the generation and/or identification of nucleic acids binding to ghrelin and in particular having the further features and characteristics as closed herein, are based on the so called SELEX process which is subject to U.S. Pat. No. 5,475,096. Basically, the SELEX process comprises the following steps:

a) generating a heterogeneous population of nucleic acids;
b) contacting the population of step a) with the target molecule;
c) separating the nucleic acid(s) not interacting with the target molecule;
d) optionally separating the nucleic acid(s) interacting with the target molecule; and
e) optionally sequencing the nucleic acid(s) interacting with the target molecule.

The exact operation of the SELEX process is known to the one skilled in the art.

Preferably, the SELEX process comprises an amplification of the individual nucleic acid binding to the target molecule using a polymerase chain reaction. By realizing this amplification a higher rate of unspecific nucleotide incorporation can be realized which results in a change of the primary sequence of the binding nucleic acid. Because of these changes new sequences may be generated which show a binding characteristic different from the one of the starting sequences such as, among others, increased affinity of specificity.

It is within the present invention that the inventive sequences originate either completely or partially from the randomised part of the members of a nucleic acid library serving as starting material for the selection process. However, it is also within the present invention that the inventive sequences either completely or partially originate from the non-randomised part of the members of the nucleic acid library serving as starting material for the selection process. Such non-randomised part is, for example, that part which is used as binding site for the amplification primer.

The inventive method for the generation of L-nucleic acids binding to ghrelin is based on the method of Fürste et al. which is subject to international patent application WO 98/08856. Basically, this method comprises the following steps:

a) generating a heterogeneous population of D-nucleic acids;
b) contacting the population of step a) with an optical antipode of the target molecule;
c) separating the D-nucleic acid not interacting with the optical antipode of the target molecule;
d) sequencing the D-nucleic acid interacting with the optical antipode of the target molecule; and
e) synthesising the L-nucleic acid sequence(s) which is/are identical to the sequence of the D-nucleic acid(s) obtained in step d);

According to the present invention the optical antipode is ghrelin. The optical antipode is present as D-pepide which means that all of the amino acids forming the peptide are D-amino acids. The target molecule, i.e. ghrelin is present as the L-enantiomer. The L-enantiomer consists of L-amino acids and is the naturally occurring form.

The protocol on how to realize the process is known to the one skilled in the art.

It is also within the present invention that any of the nucleic acids according to the present invention may be used in the method for the generation and/or identification of nucleic acids binding to ghrelin and/or the method for the generation of L-nucleic acids binding to ghrelin, respectively, according to the present invention.

The inventive nucleic acids, which are also referred to herein as the nucleic acids according to the present invention, and/or the antagonists according to the present invention may be used for the generation or manufacture of a medicament. Such medicament contains at least one of the inventive nucleic acids, optionally together with further pharmaceutically active compounds, whereby the inventive nucleic acid preferably acts as pharmaceutically active compound itself. Such medicaments comprise in preferred embodiments at least a pharmaceutically acceptable carrier. Such carrier may be, e.g., water, buffer, starch, sugar, gelatine or any other acceptable carrier substance. Such carriers are generally known to one skilled in the art. Disease and/or disorders and/or diseased conditions for the treatment and/or prevention of which such medicament may be used include, but are not limited to obesity, the regulation of energy balance, appetite and body weight, eating disorders, diabetes, glucose metabolism, tumour, blood pressure and cardiovascular diseases. As will be acknowledged by the ones of the art the inventive nucleic acids may factually be used in any disease where an antagonist to ghrelin can be administered to a patient in need of such antagonist and such antagonist is suitable to eliminate the cause of the disease or the disorder or at least to reduce the effects from the disease or the disorder. Such effect includes, but is not limited to obesity, the regulation of energy balance, appetite and body weight, eating disorders, diabetes, glucose metabolism, tumour treatment, blood pressure and cardiovascular diseases. For the purpose of the present invention regulation of energy balance is regarded as a disease. More particularly, the use is for the treatment of any disease where the regulation of the energy balance is influenced by ghrelin, either directly or indirectly, and whereby reduction of the bioavailability of ghrelin is desired. The same applies to sugar metabolism, blood pressure and appetite and body weight. Further disease which may be treated using the nucleic acids according to the present invention, possibly upon systemic or local application are those which can be selected from the group comprising pituitary tumors, acromegaly, central Cushing's syndrome, adrenal Cushing's syndrome, paraneoplastic Cushing's syndrome, ectopic Cushing's syndrome, adrenal tumor, stress, hypercortisolism, cardiac insufficiency, cardiay infarction, stroke, adrenocortical insufficiency, hypotonia, aortic stenosis, pulmonal hypertonia, constrictive pericarditis, infectious diseases, infectious toxic hypotonia, hypovolemia, and hypronatriemia.

It is to be understood that the nucleic acid as well as the antagonists according to the present invention can be used not only as a medicament or for the manufacture of a medicament, but also for cosmetic purposes, particularly with regard to the involvement of ghrelin in obesity. For the same purpose the nucleic acid as well as the antagonists according to the present invention can be used as a food additive, a means for weight control and/or a means for appetite control. A composition comprising the nucleic acid as well as the antagonists according to the present invention can be used for any of the aforementioned purposes.

The inventive nucleic acid may further be used as starting material for drug design. Basically there are two possible approaches. One approach is the screening of compound libraries whereas such compound libraries are preferably low molecular weight compound libraries. Such libraries are known to the one skilled in the art. Alternatively, the nucleic acid according to the present invention may be used for rational design of drugs.

The rational design of drugs may start from any of the nucleic acid according to the present invention and involves a structure, preferably a three dimensional structure, which is similar to the structure of the inventive nucleic acids or identical to the binding mediating parts of the structure of the inventive nucleic acids. In any case such structure still shows the same or a similar binding characteristic as the inventive nucleic acids. In either a further step or as an alternative step in the rational design of drugs the preferably three dimensional structure of those parts of the nucleic acids binding to the neurotransmitter are mimicked by chemical groups which are different from nucleotides and nucleic acids. By this mimicry a compound different from the nucleic acids can be designed. Such compound is preferably a small molecule or a peptide.

In case of screening of compound libraries, such as by using a competitive assay which are known to the one skilled in the arts, appropriate ghrelin analogues, ghrelin agonists or ghrelin antagonists may be found. Such competitive assays may be set up as follows. The inventive nucleic acid, preferably a spiegelmer which is a target binding L-nucleic acid, is coupled to a solid phase. In order to identify ghrelin analogues labeled ghrelin may be added to the assay. A potential analogue would compete with the ghrelin molecules binding to the spiegelmer which would go along with a decrease in the signal obtained by the respective label. Screening for agonists or antagonists may involve the use of a cell culture assay as known to the ones skilled in the art.

The kit according to the present invention may comprise at least one or several of the inventive nucleic acids. Additionally, the kit may comprise at least one or several positive or negative controls. A positive control may, for example, be ghrelin, particularly the one against which the inventive nucleic acid is selected or to which it binds, preferably, in liquid form. A negative control may, e.g., be a peptide which is defined in terms of biophysical properties similar to ghrelin, but which is not recognized by the inventive nucleic acids. Furthermore, said kit may comprise one or several buffers. The various ingredients may be contained in the kit in dried or lyophilised form or solved in a liquid. The kit may comprise one or several containers which in turn may contain one or several ingredients of the kit.

The present invention is further illustrated by the figures, examples and the sequence listing from which further features, embodiments and advantages may be taken, wherein FIG. 1 shows table 1A indicating the signal to noise ratio of the RNA selection for D-ghrelin binding aptamers;

FIG. 2 shows table 1B indincating the signal to noise ratio of the 2'F-RNA selection for D-ghrelin binding aptamers;

FIG. 3 shows table 2 indicating the amount of RNA/2F-RNA used in the selection process;

FIG. 4A shows the course of the ghrelin peptide concentration used in the RNA selection;

FIG. 4B shows the course of the ghrelin peptide concentration used in the 2'F-RNA selection;

FIG. 5 shows the course of eluted RNA in percent of total used RNA over the course of peptide concentration;

FIG. 6 shows the course of eluted RNA in percent of total used 2'F-RNA over the course of peptide concentration;

FIG. 7A shows table 3 indicating double rounds and binding assays performed from round 12 to 14 for the RNA selection; data in percent binding to ghrelin, * marks sequences;

FIG. 7B shows an improvement if the 2'F-RNA pool binding to D-ghrelin monitored over double rounds;

Figure 10:
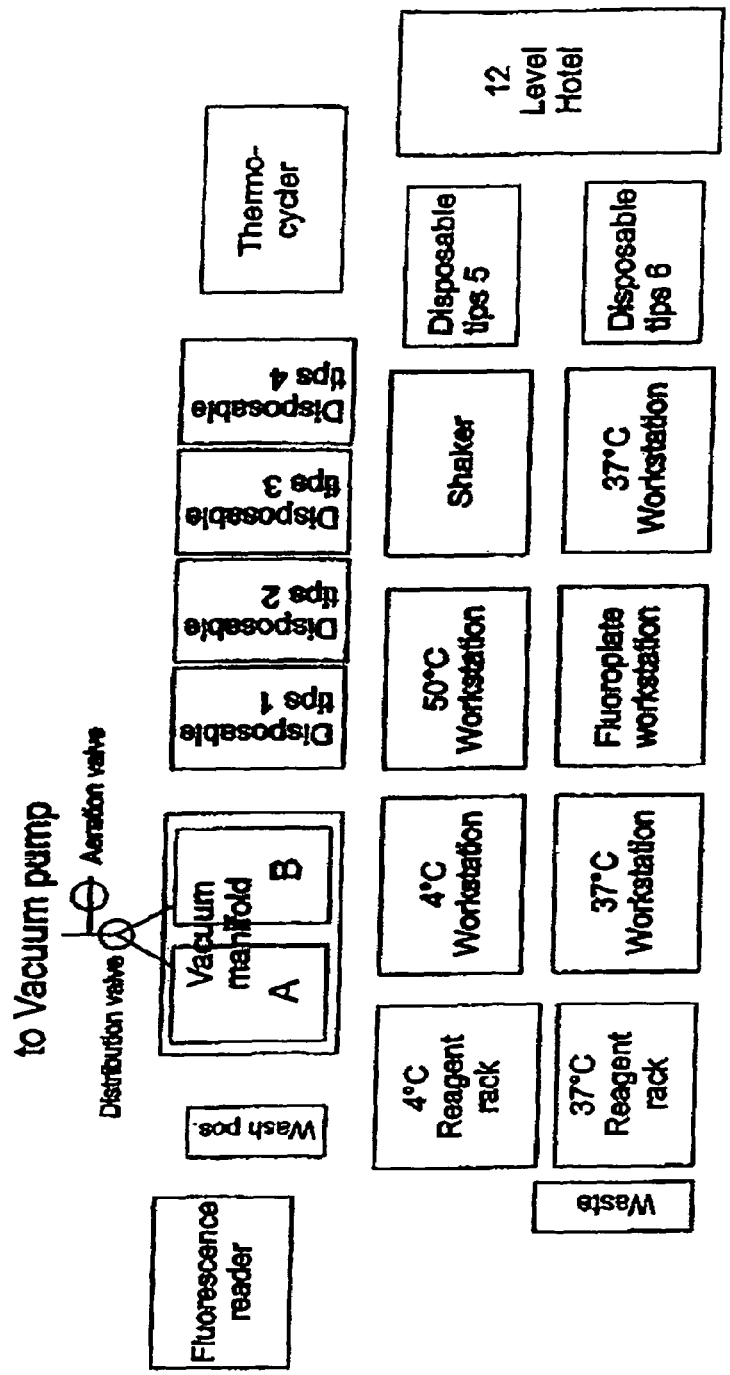
Figure 11:
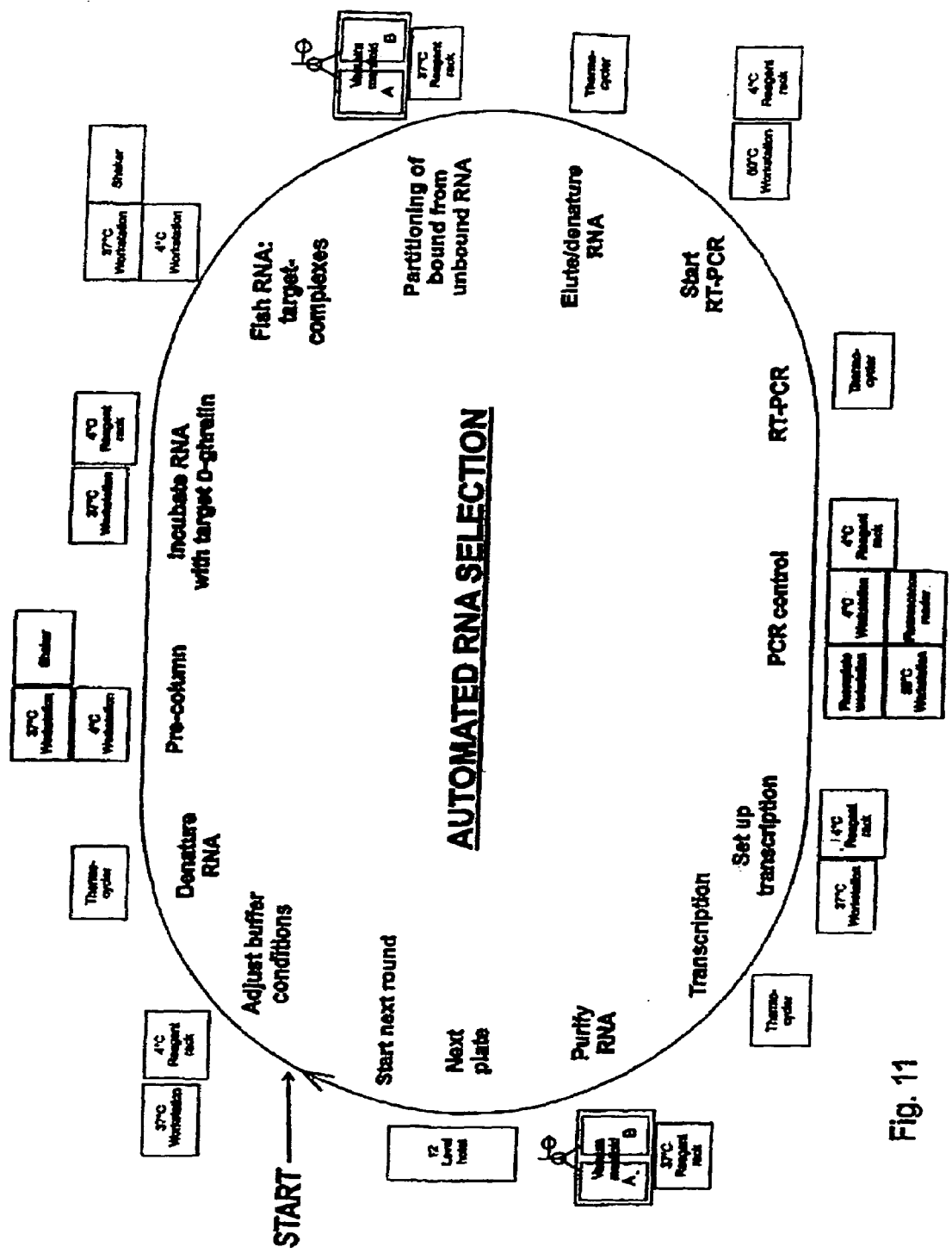
Figure 14:
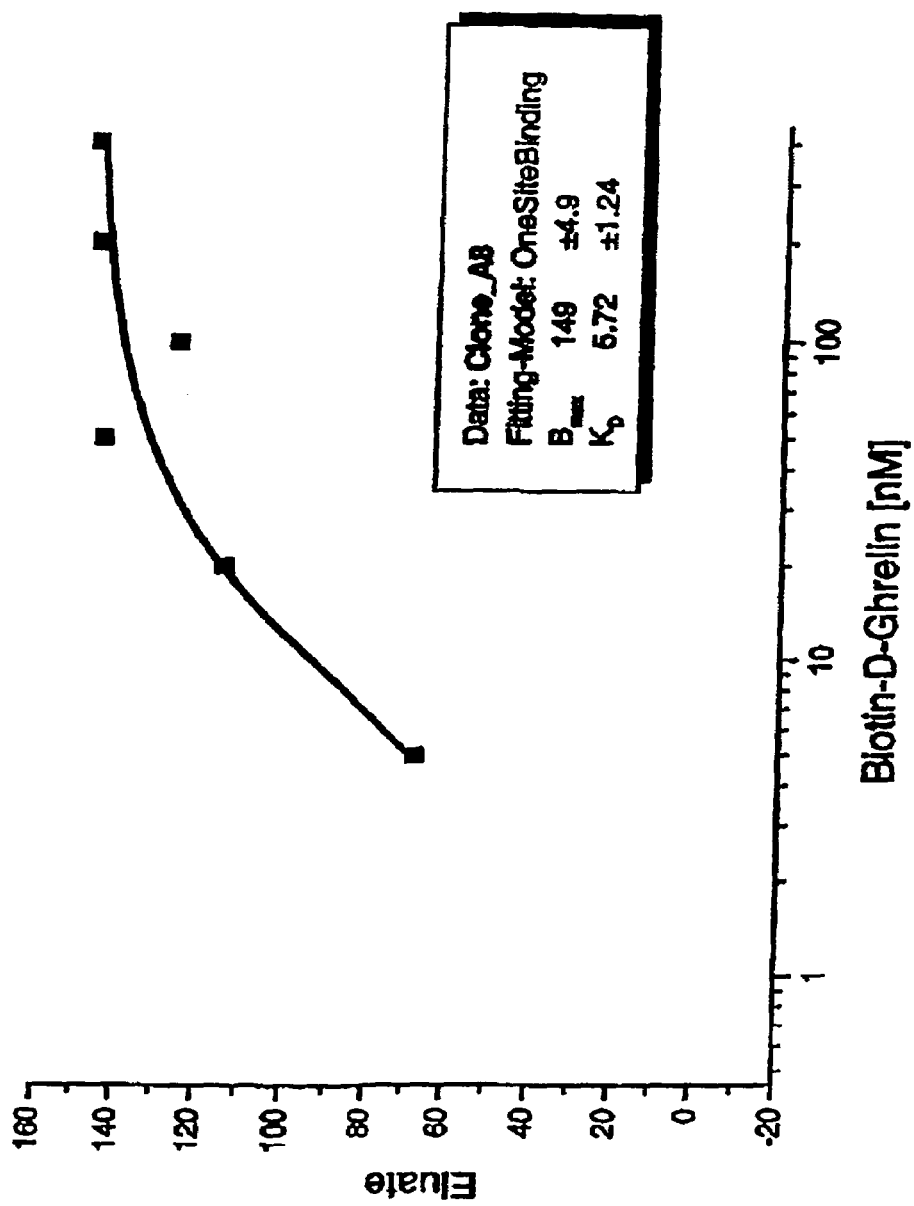
Figure 14:
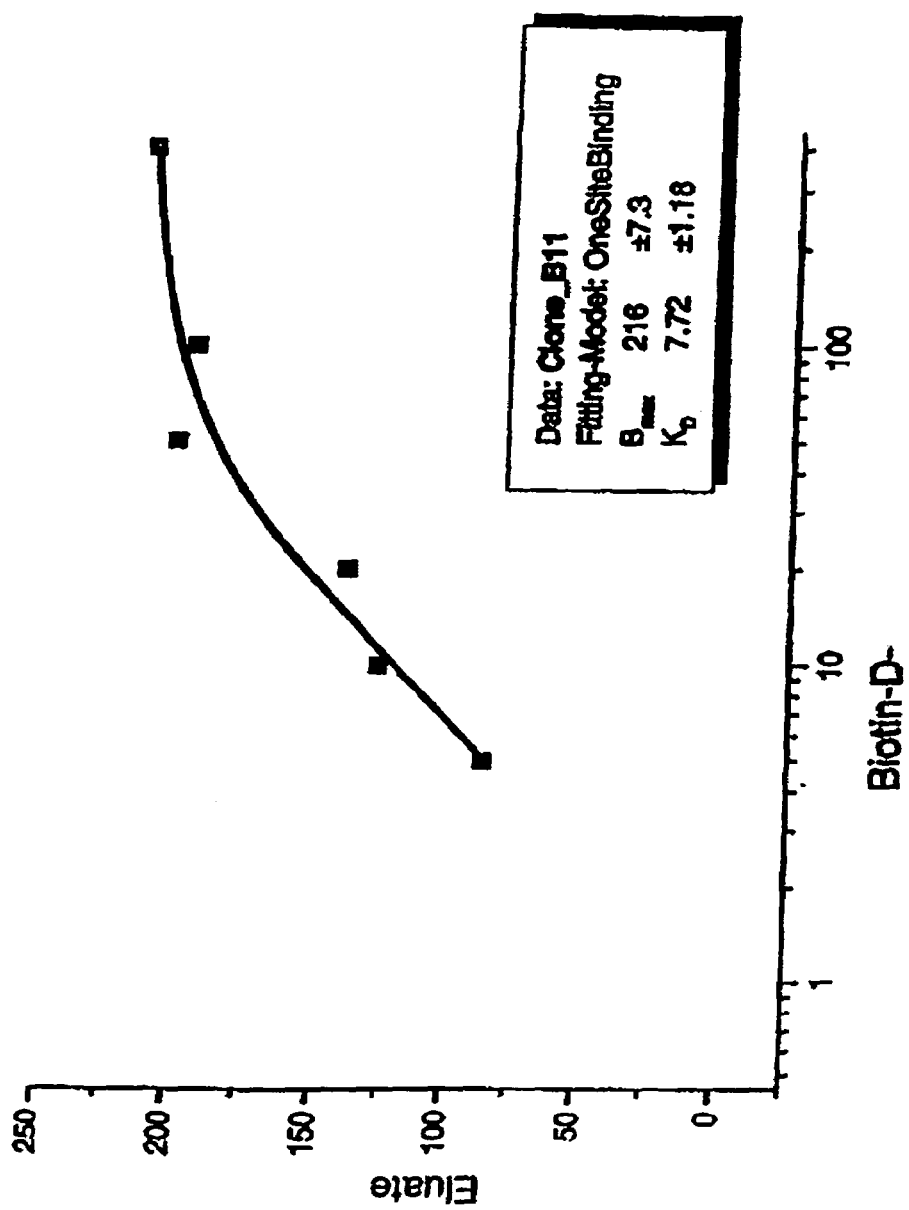
Figure 14:
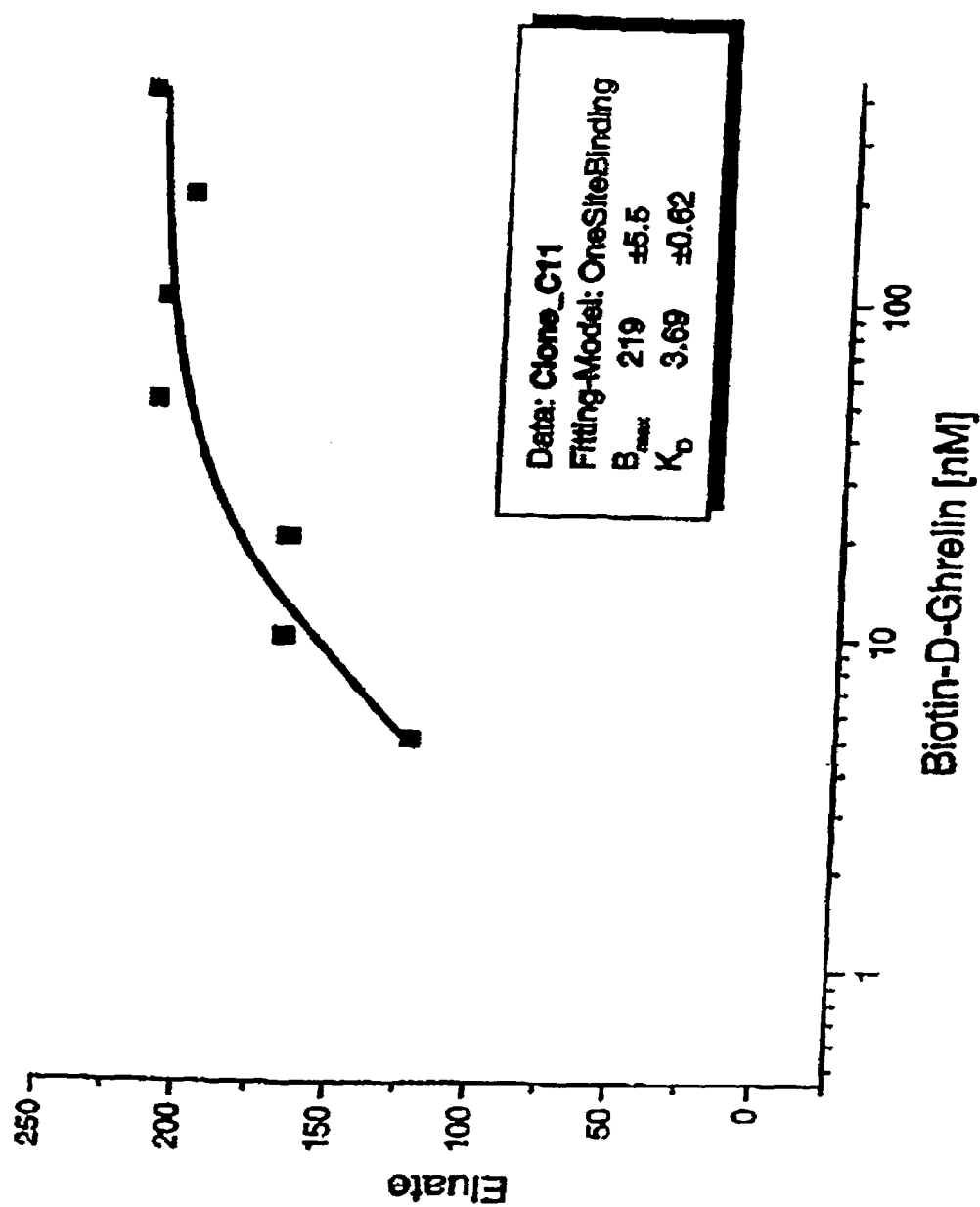
Figure 14:
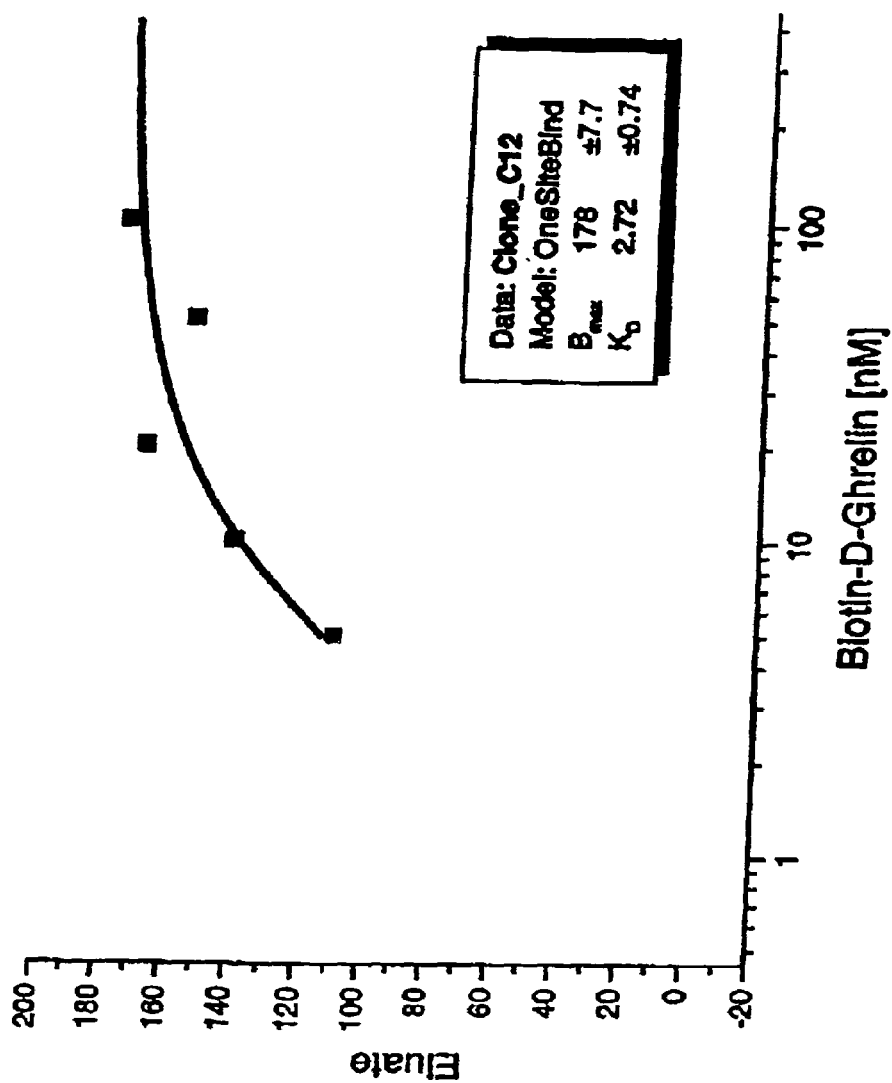
Figure 14:
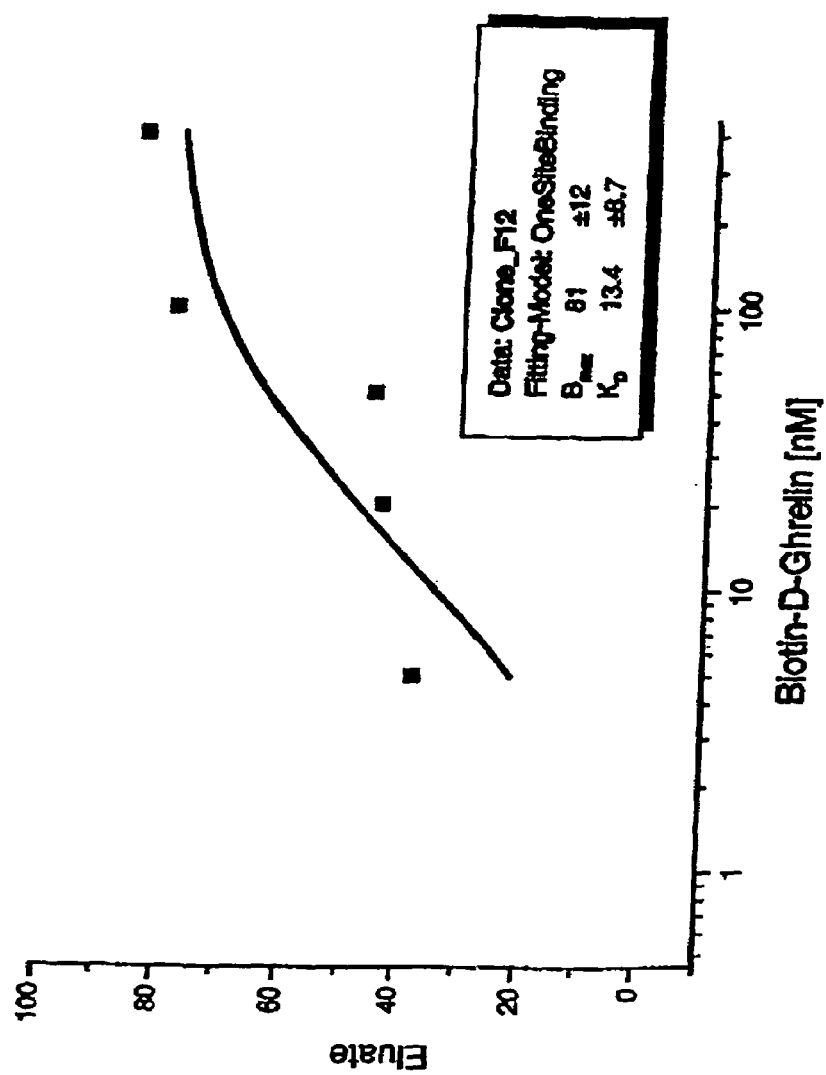
Figure 16:
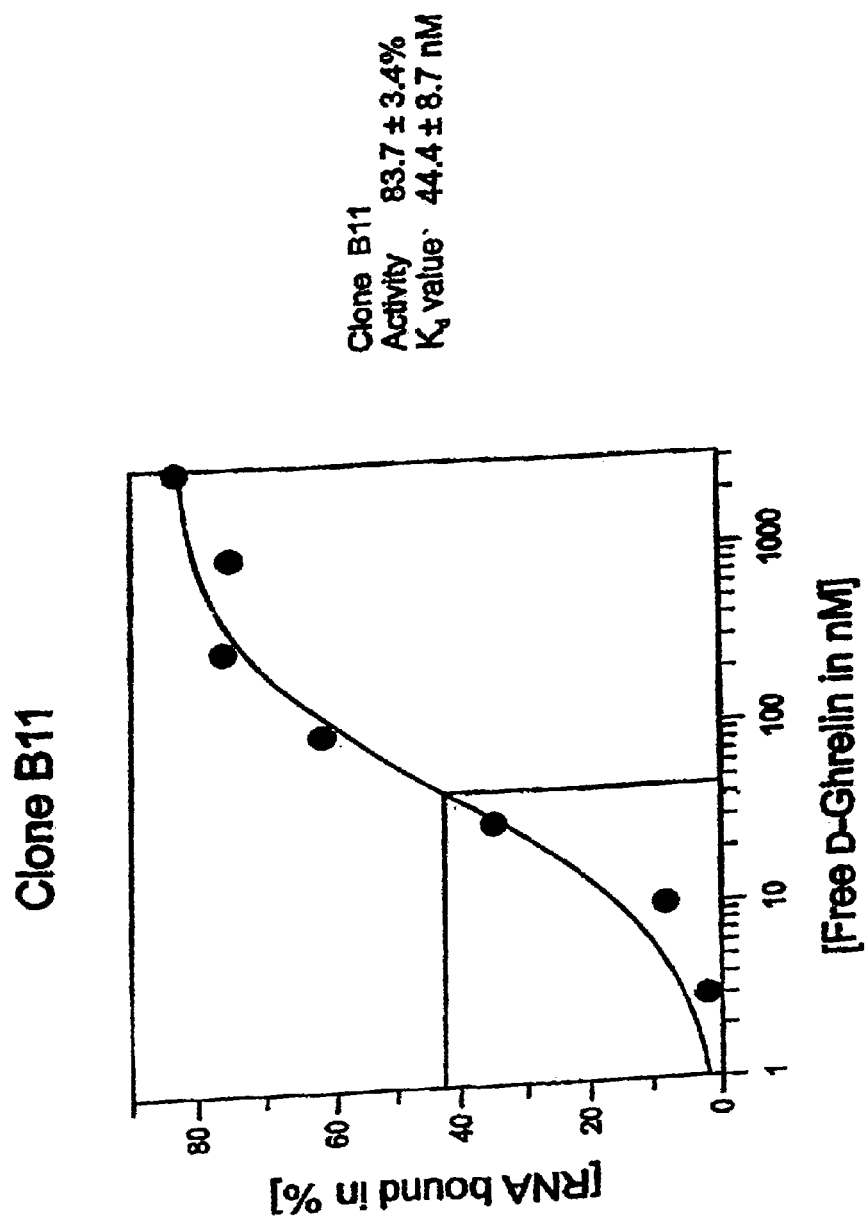
Figure 16:
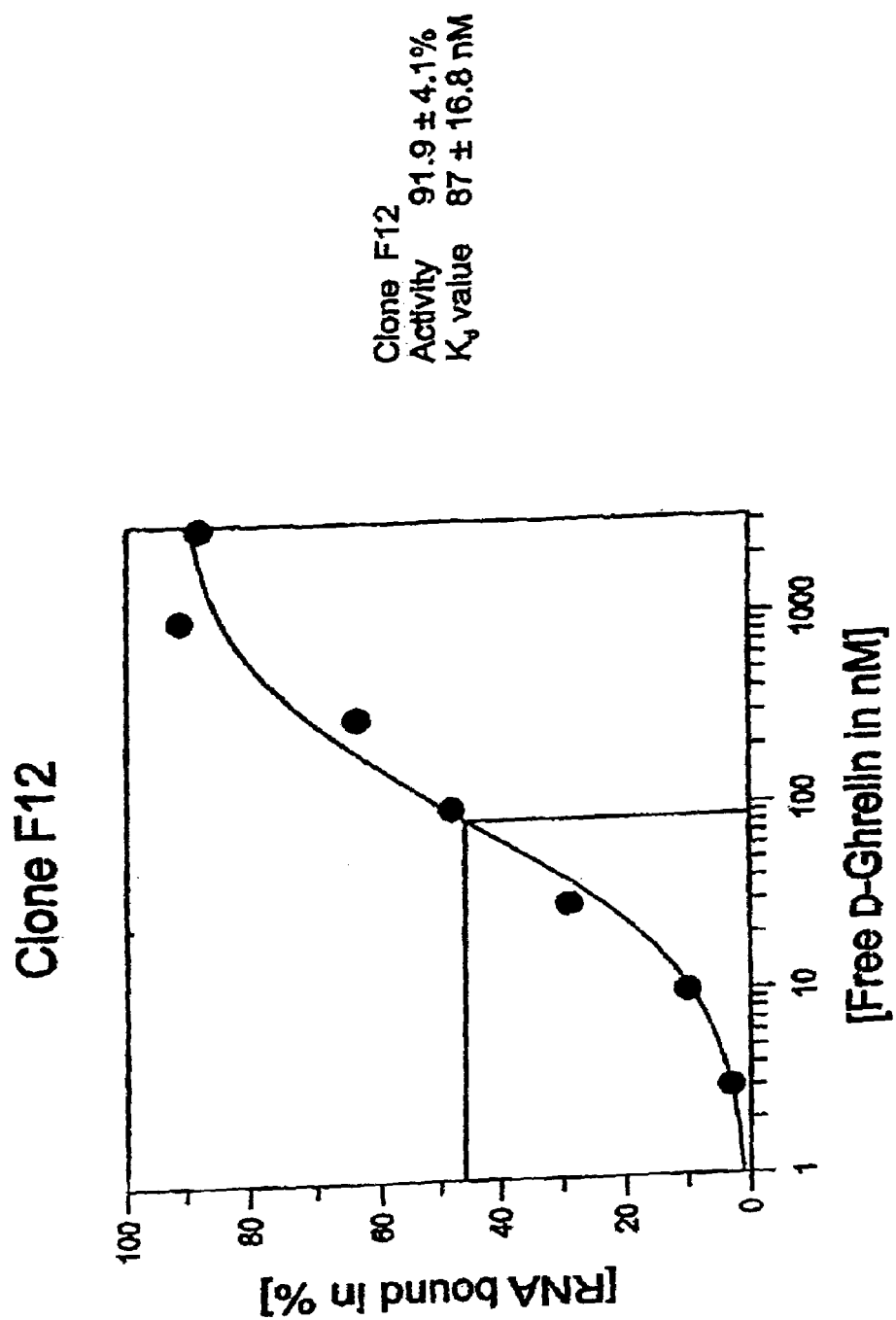
Figure 16:
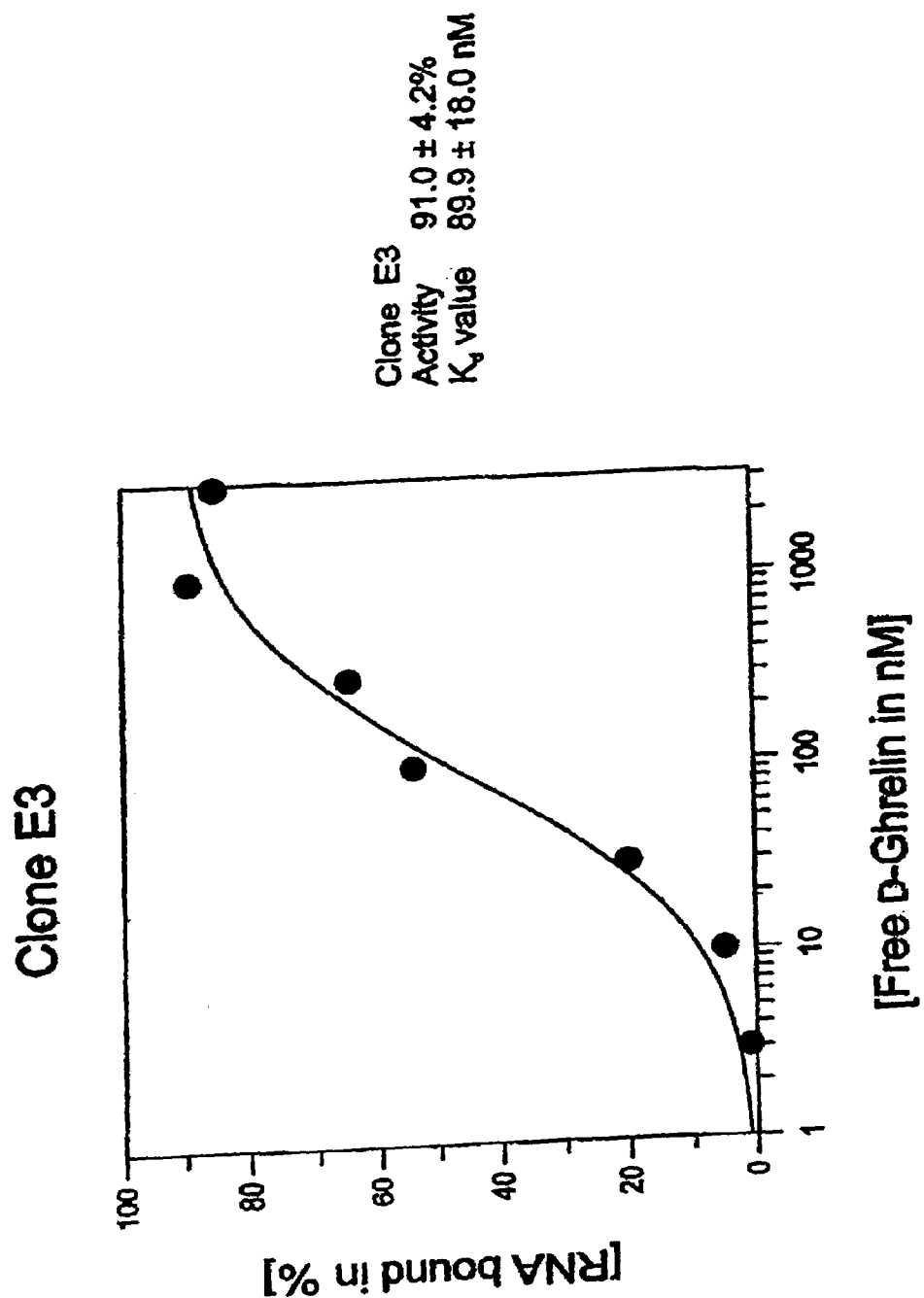
Figure 18:
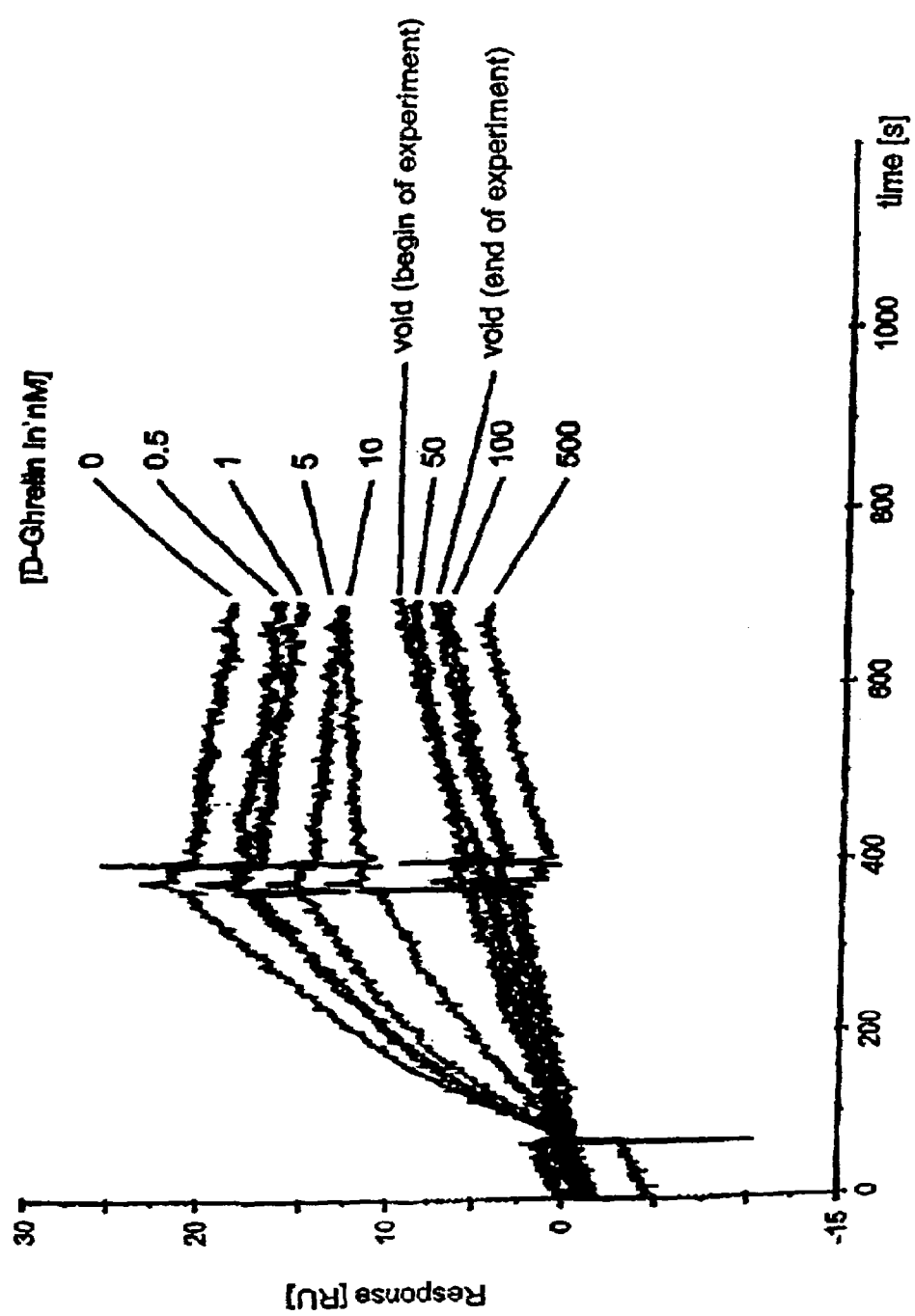
Figure 19:
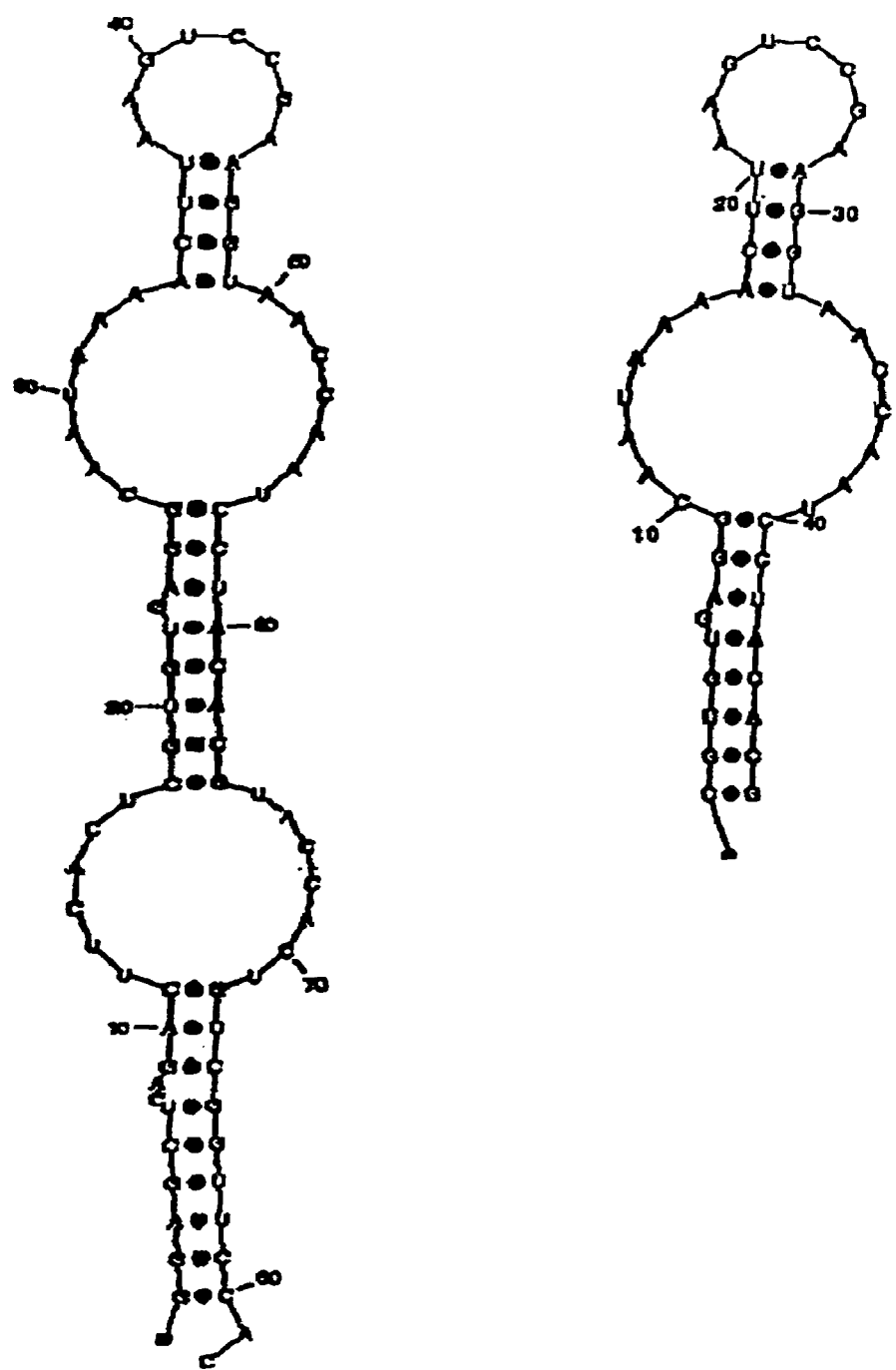
Figure 21:
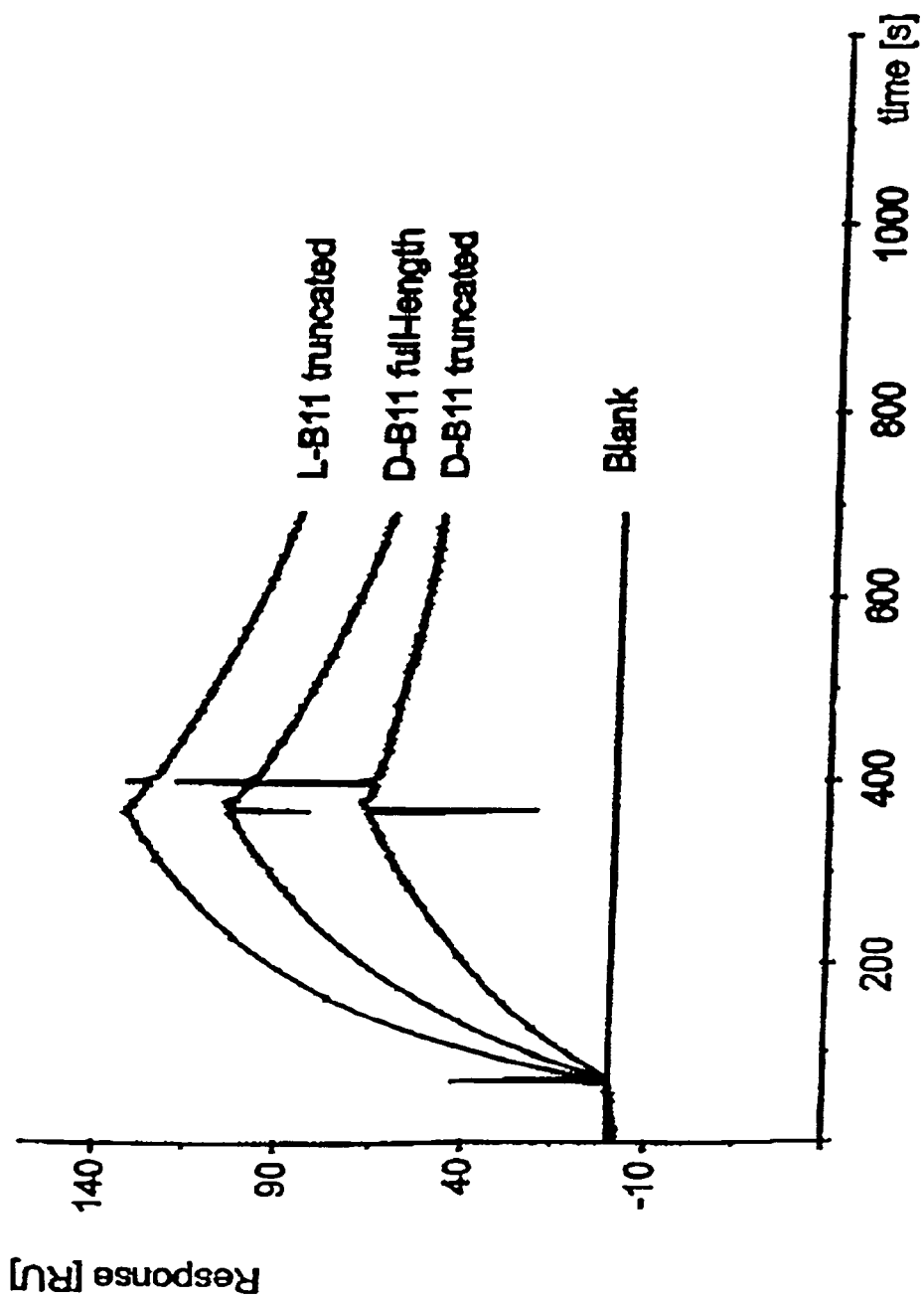
Figure 26:
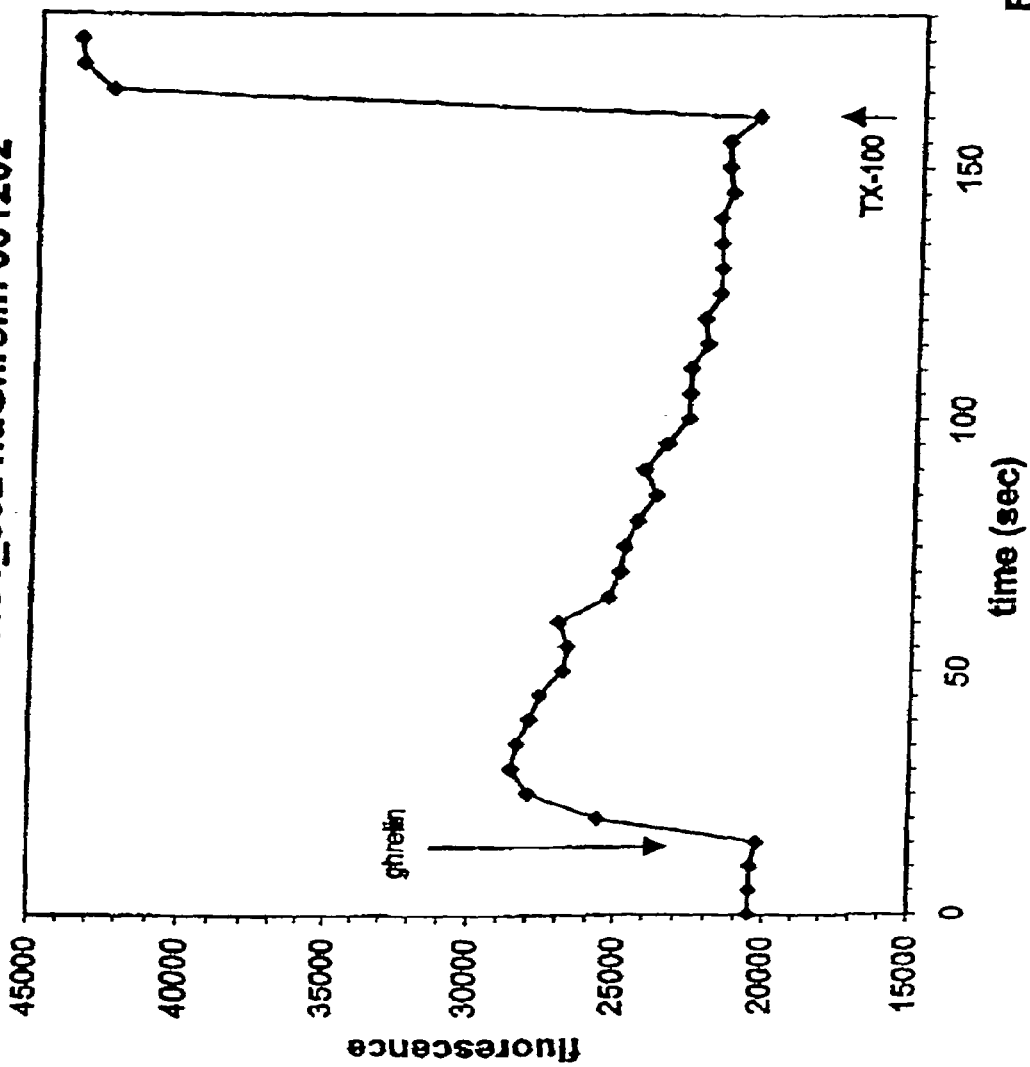
Figure 27:
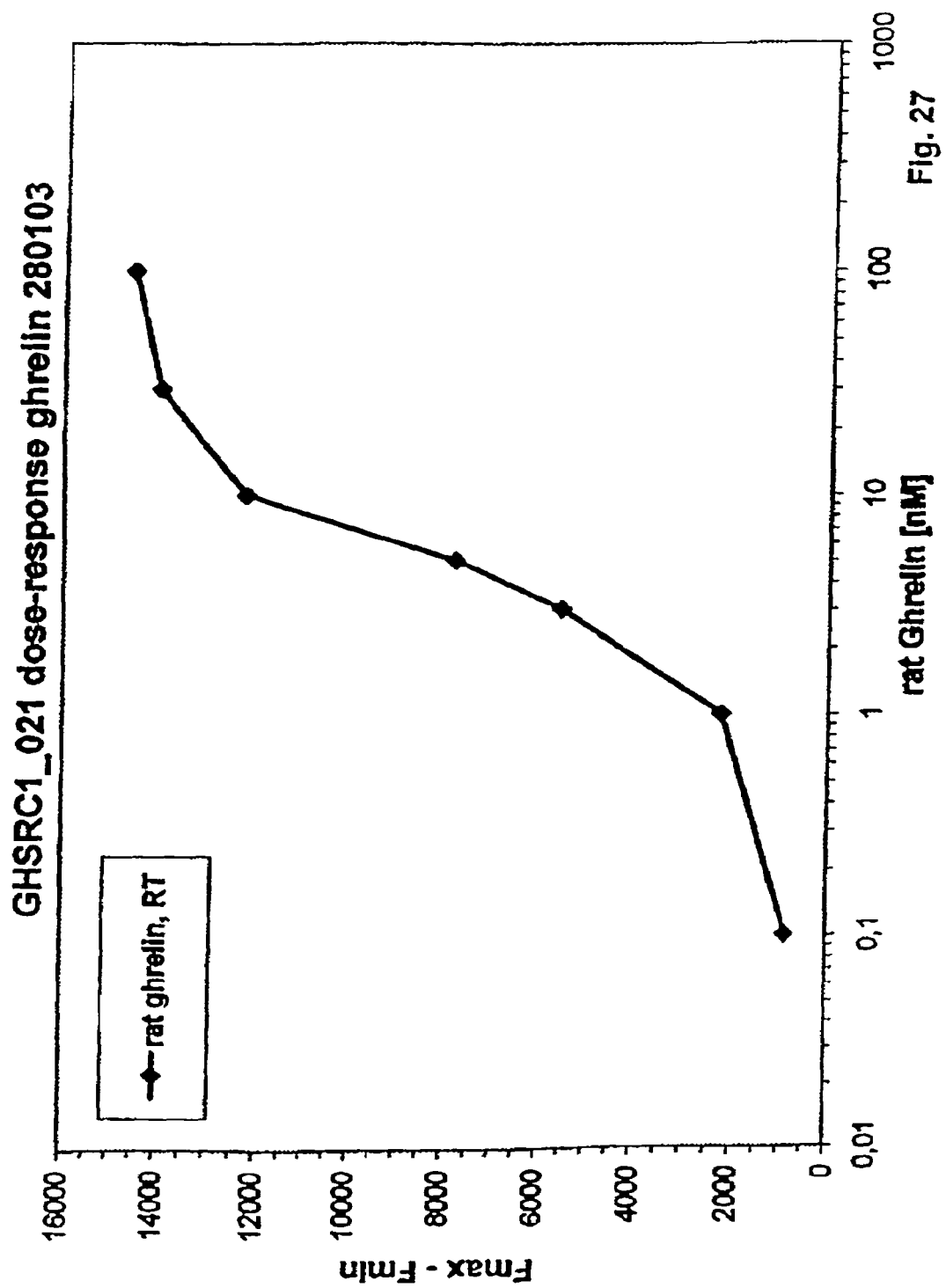
Figure 28:
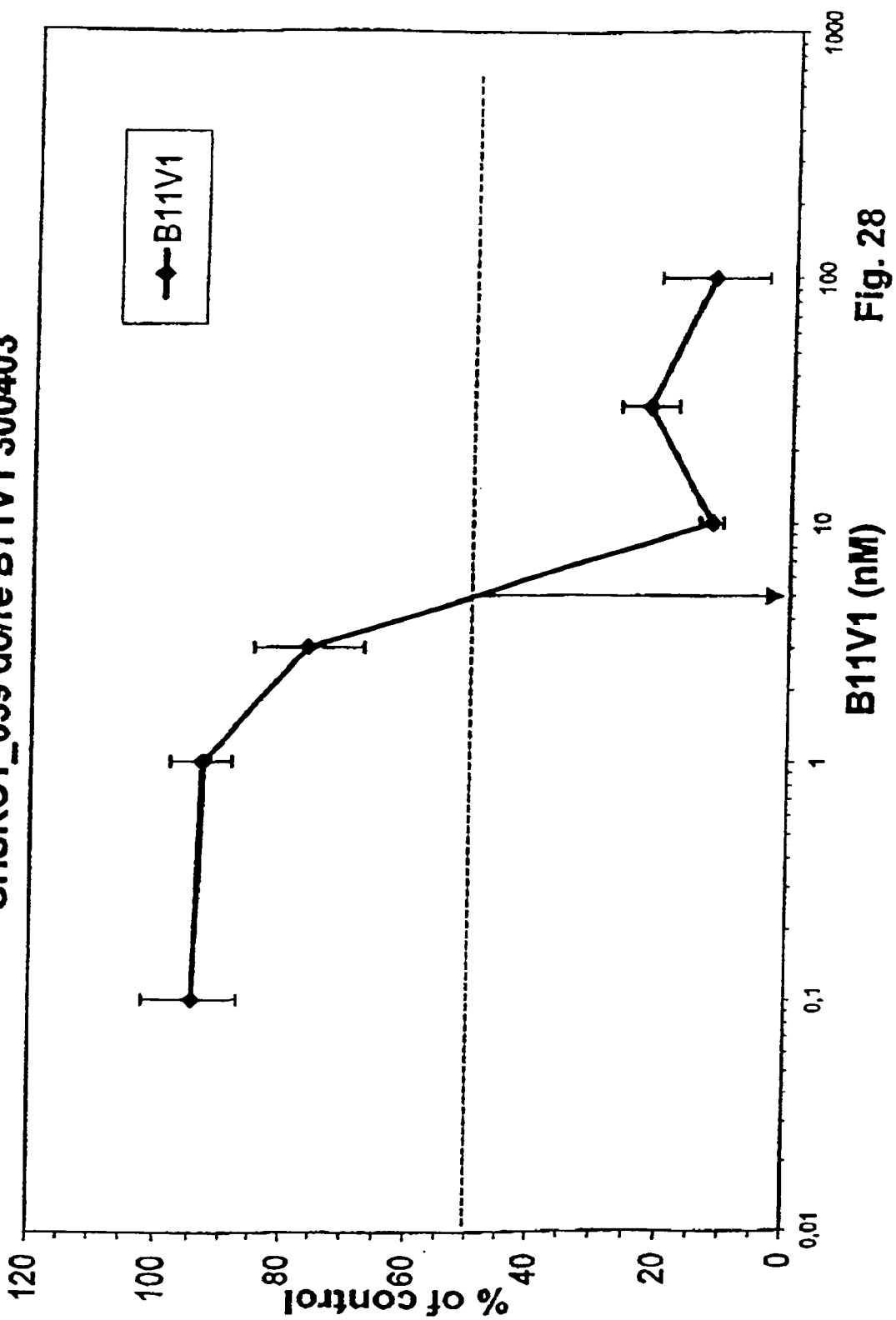
Figure 29:
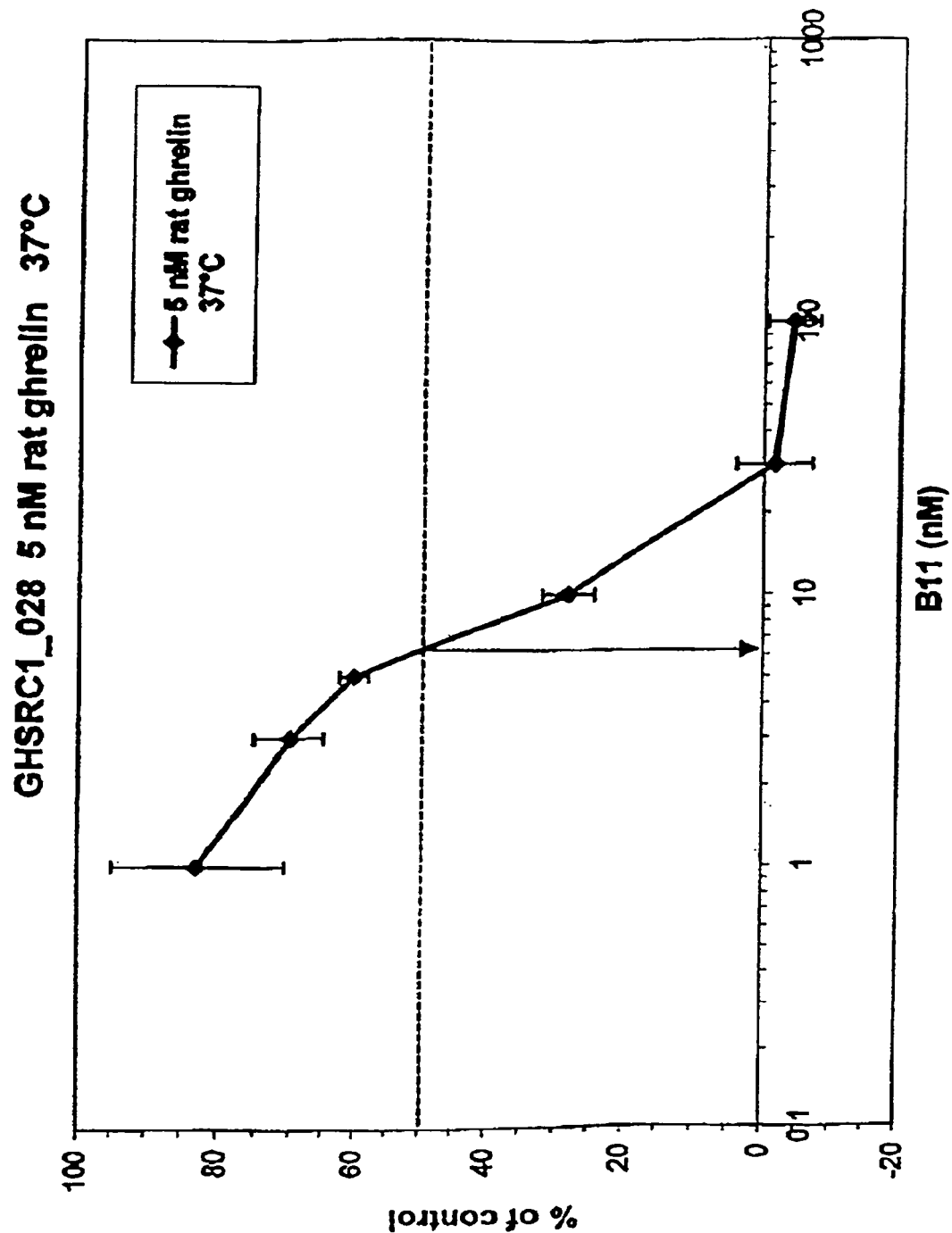
Figure 30:
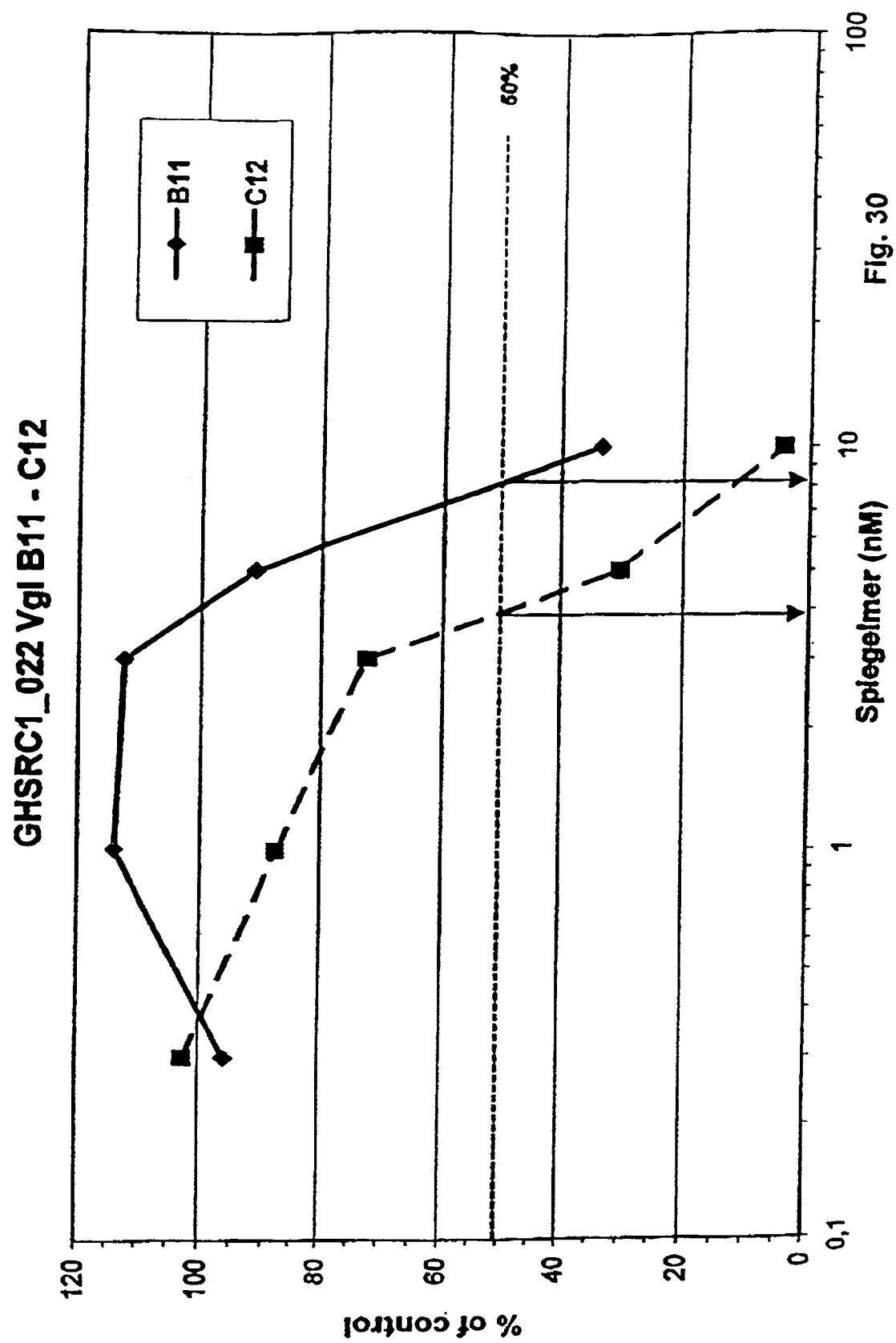
Figure 32A:
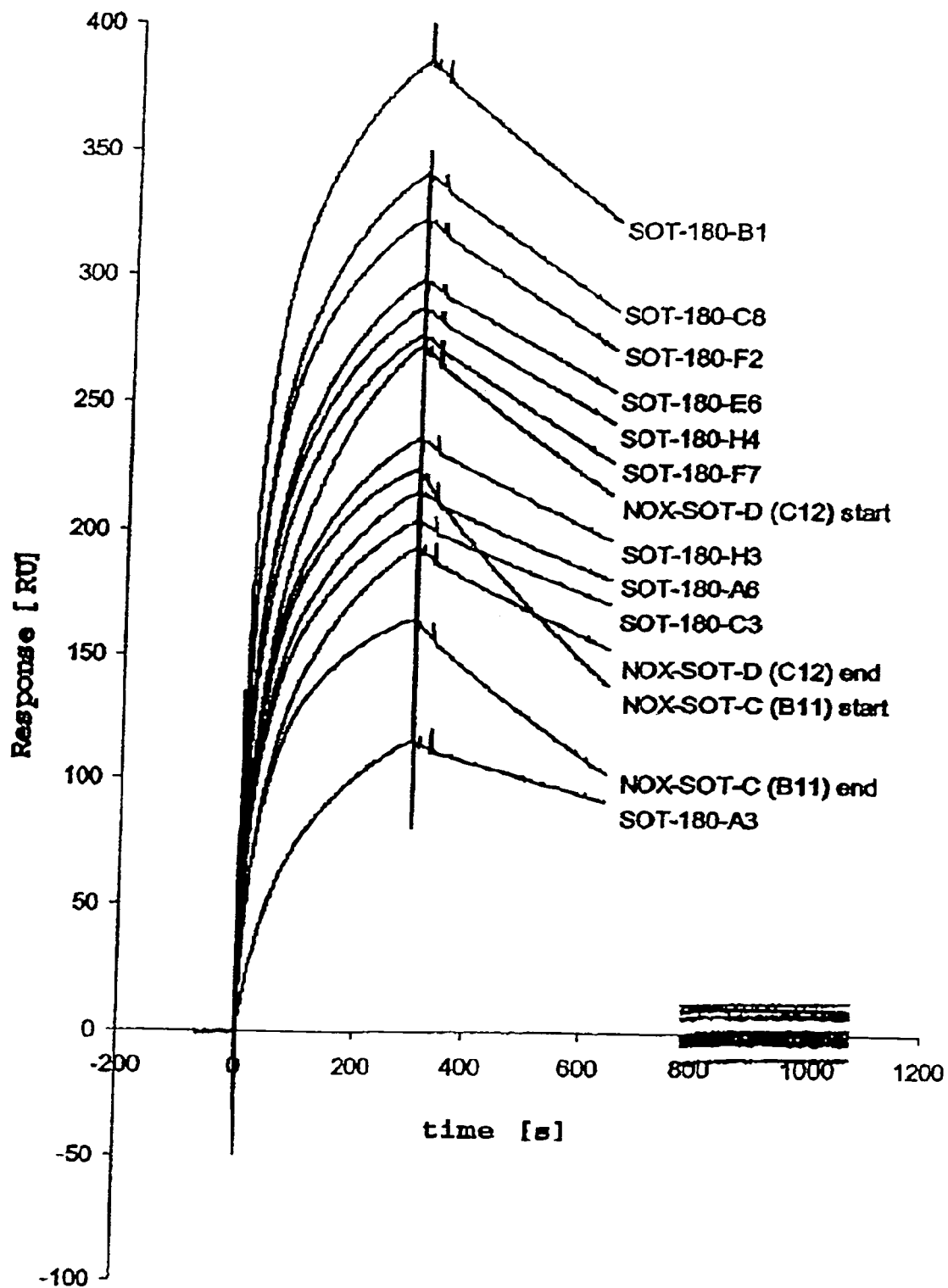
Figure 32B:
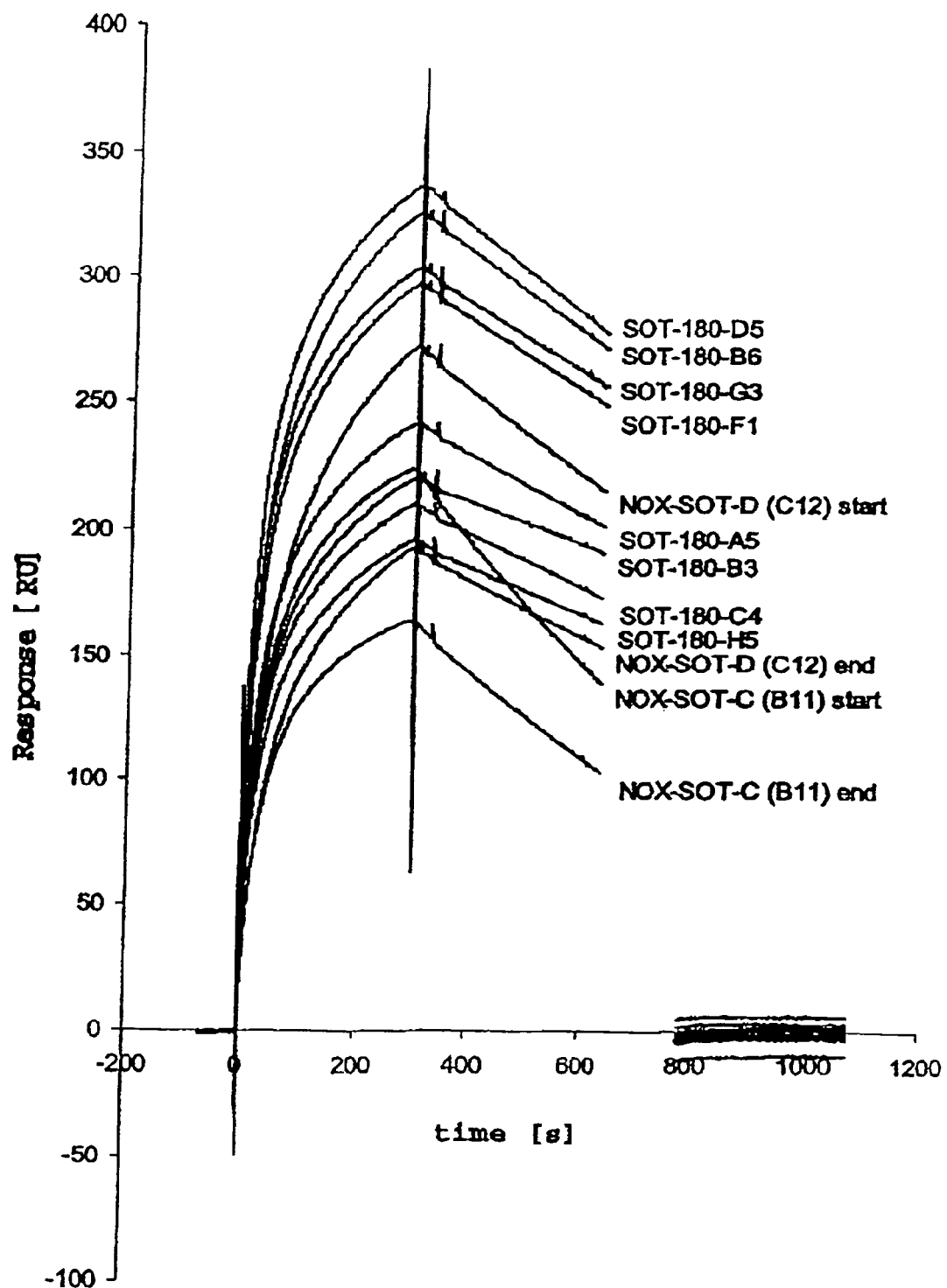
Figure 32C:
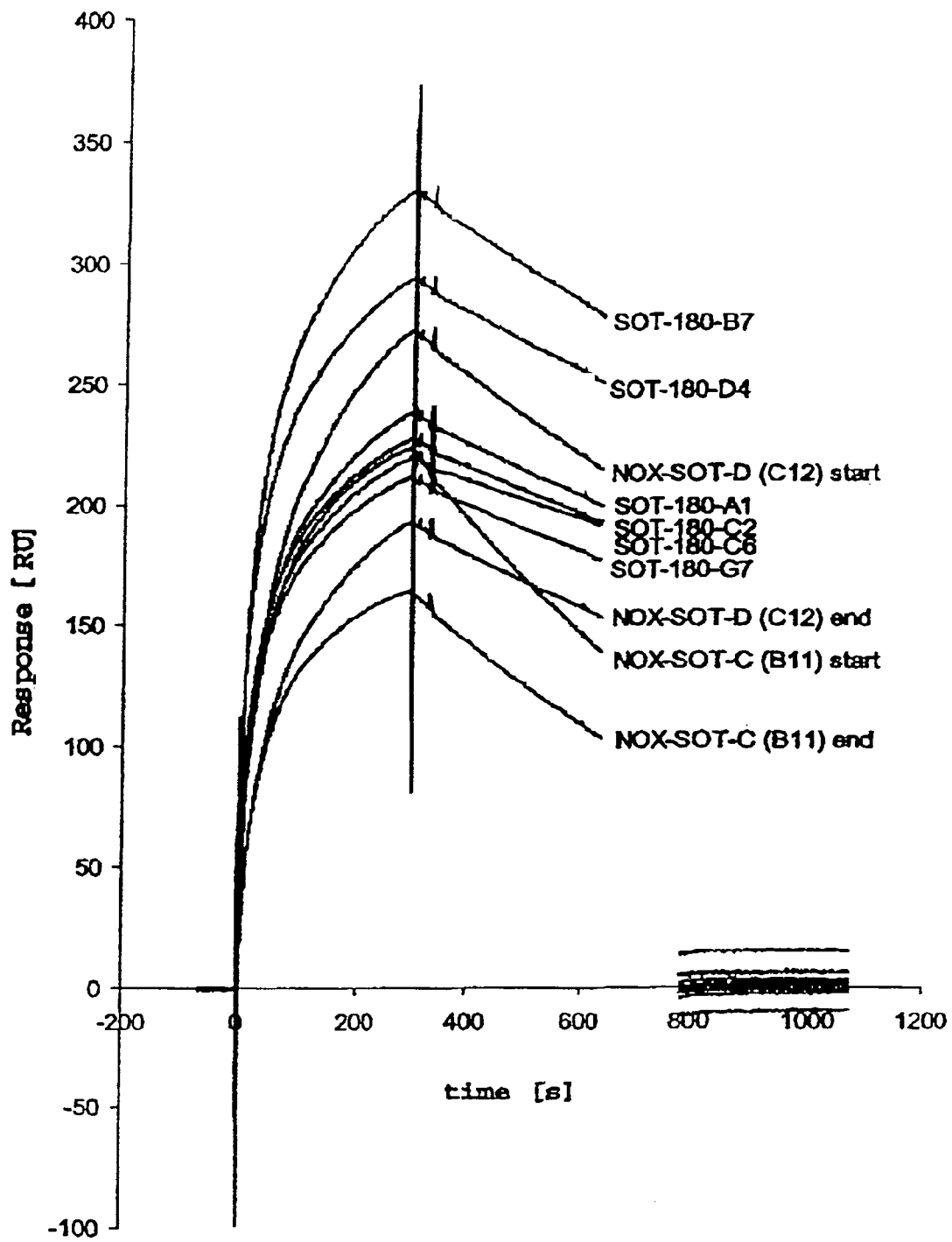
Figure 34:
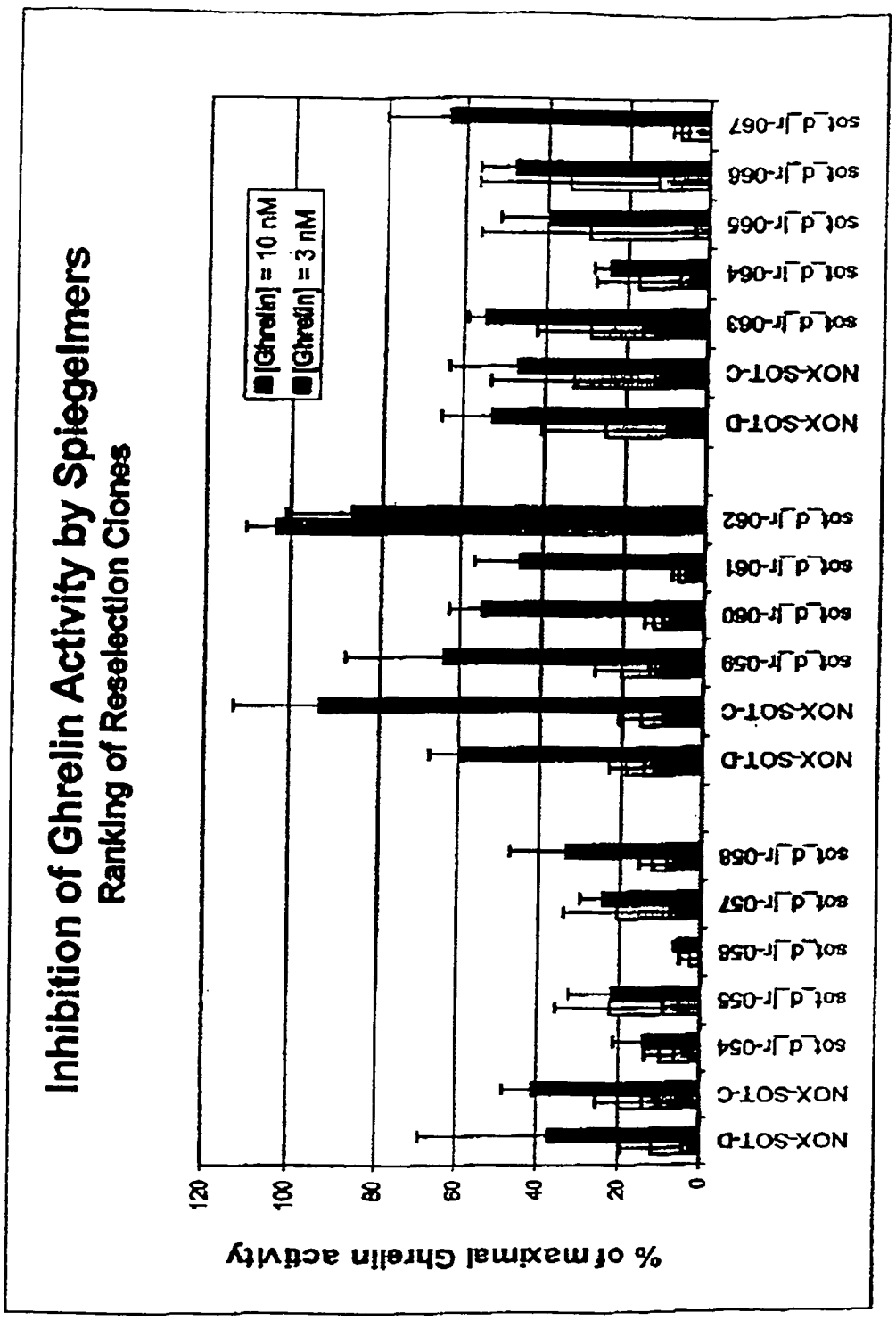
Figure 35:
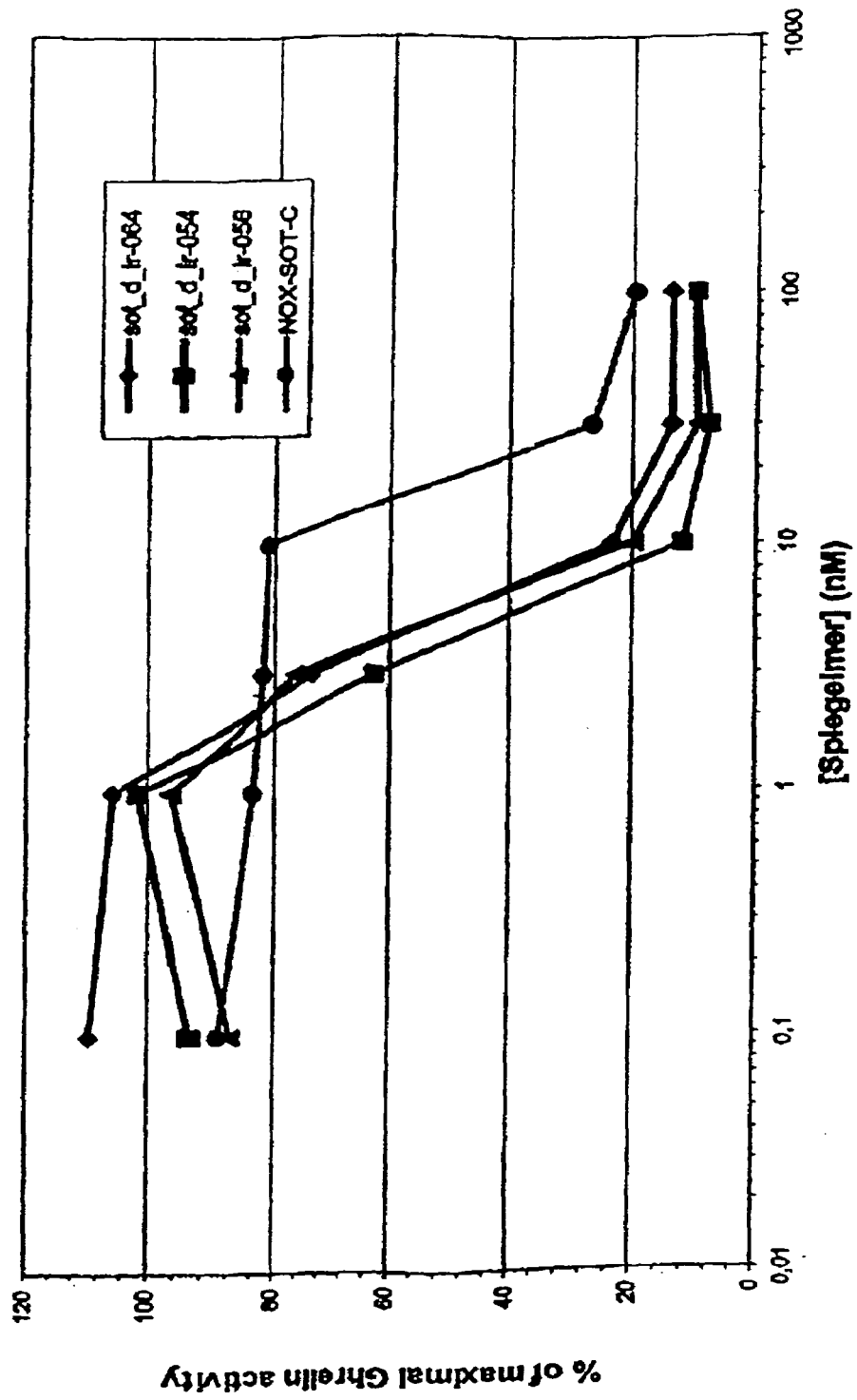
Figure 36:
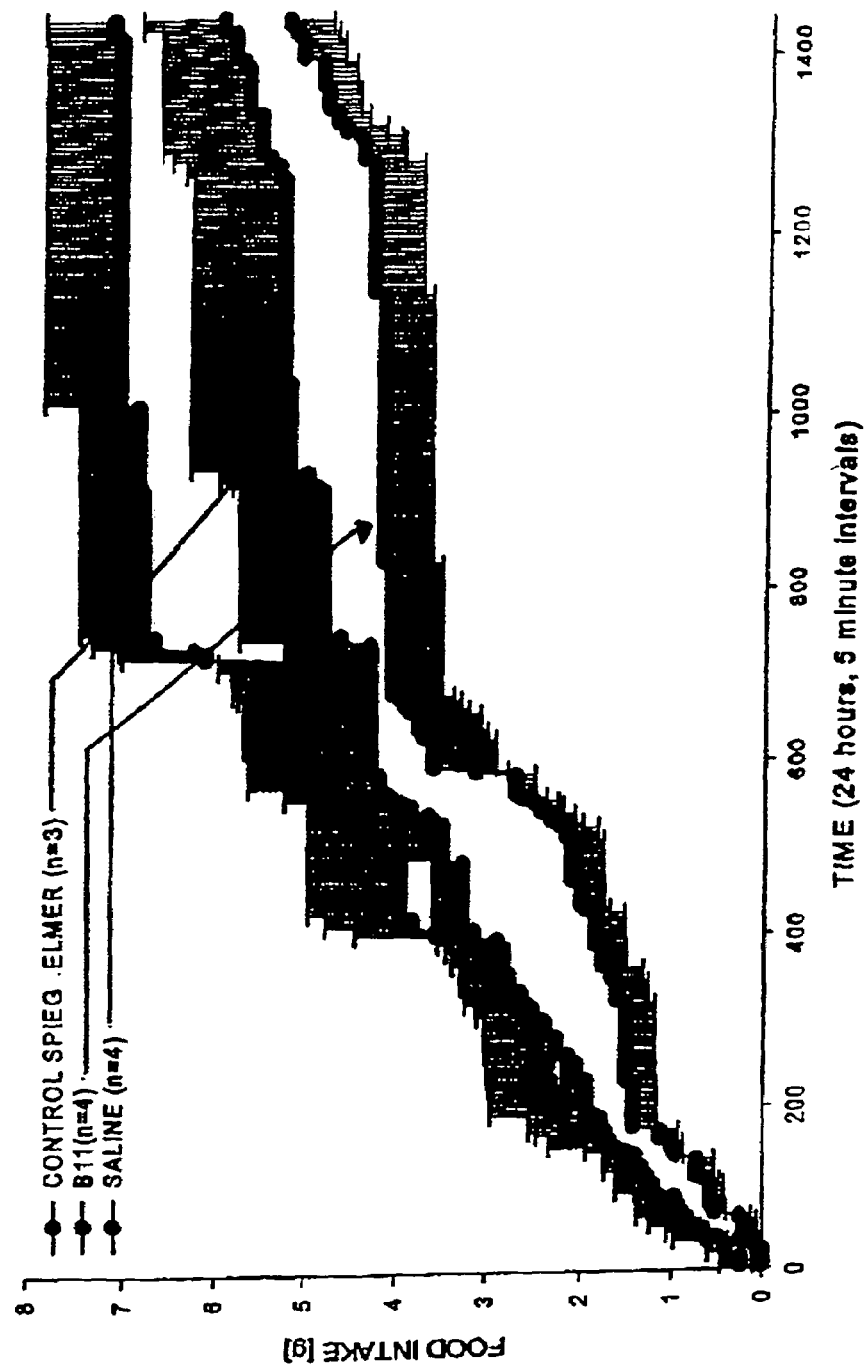
Figure 36:
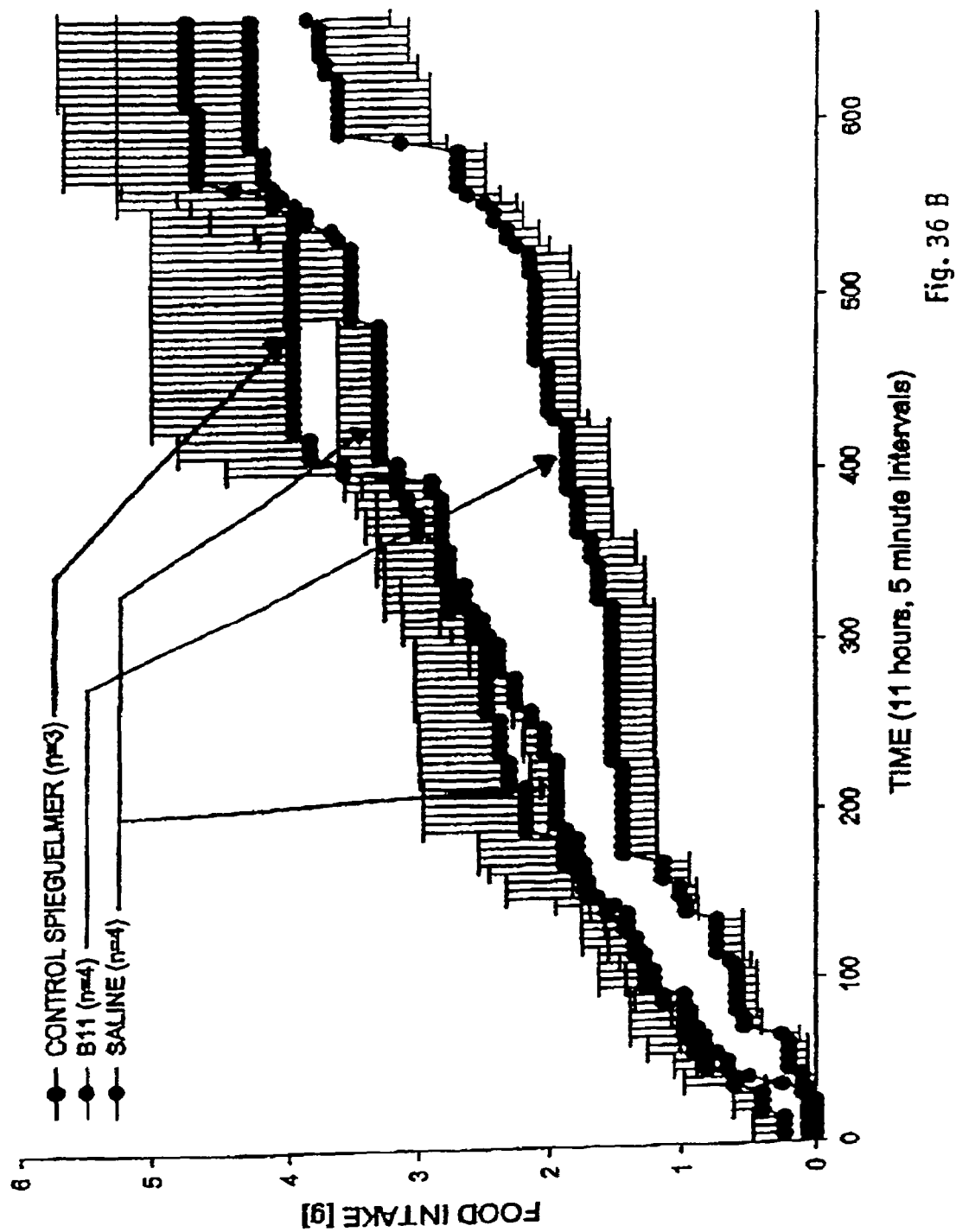
Figure 42:
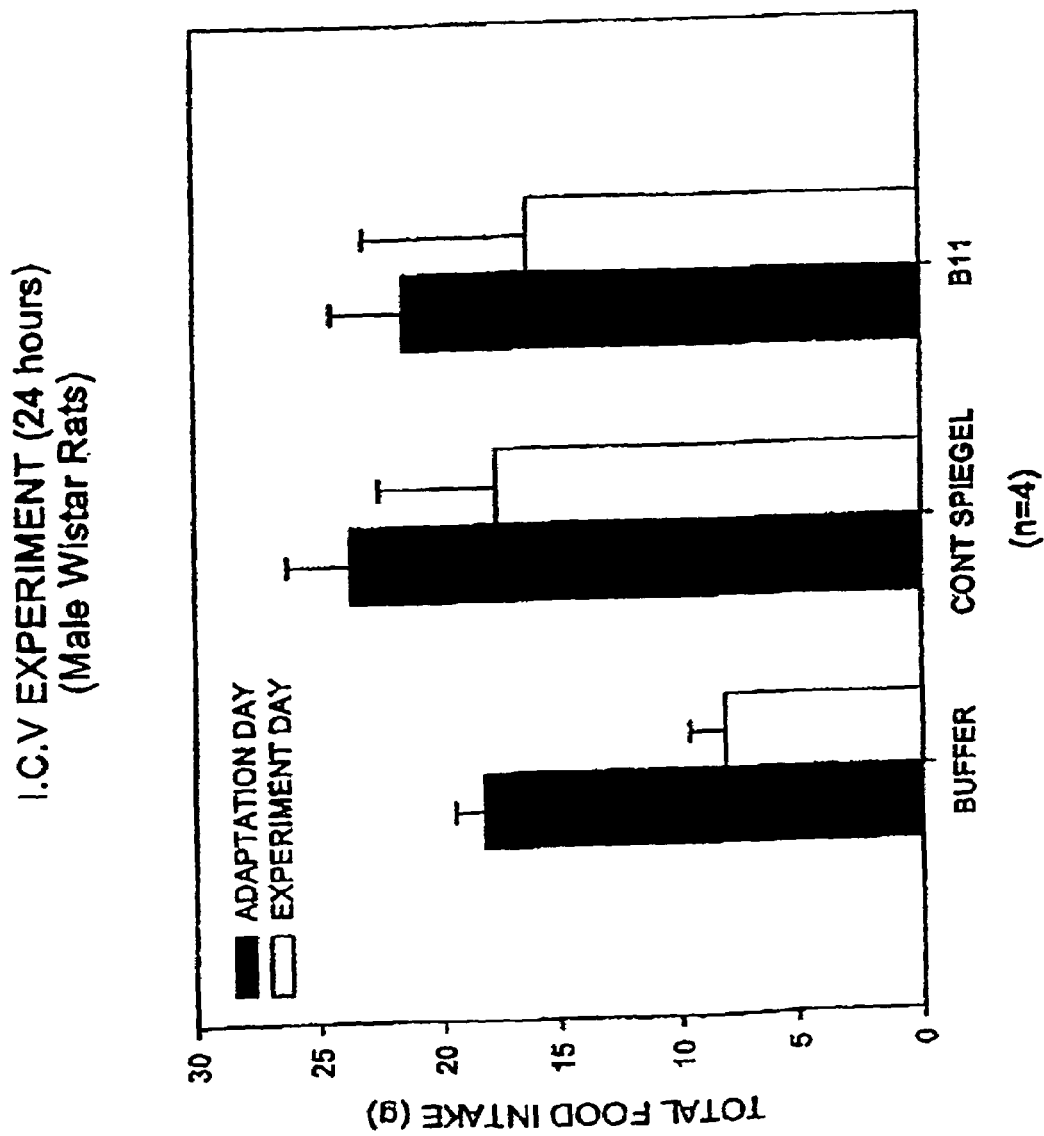
Figure 43:
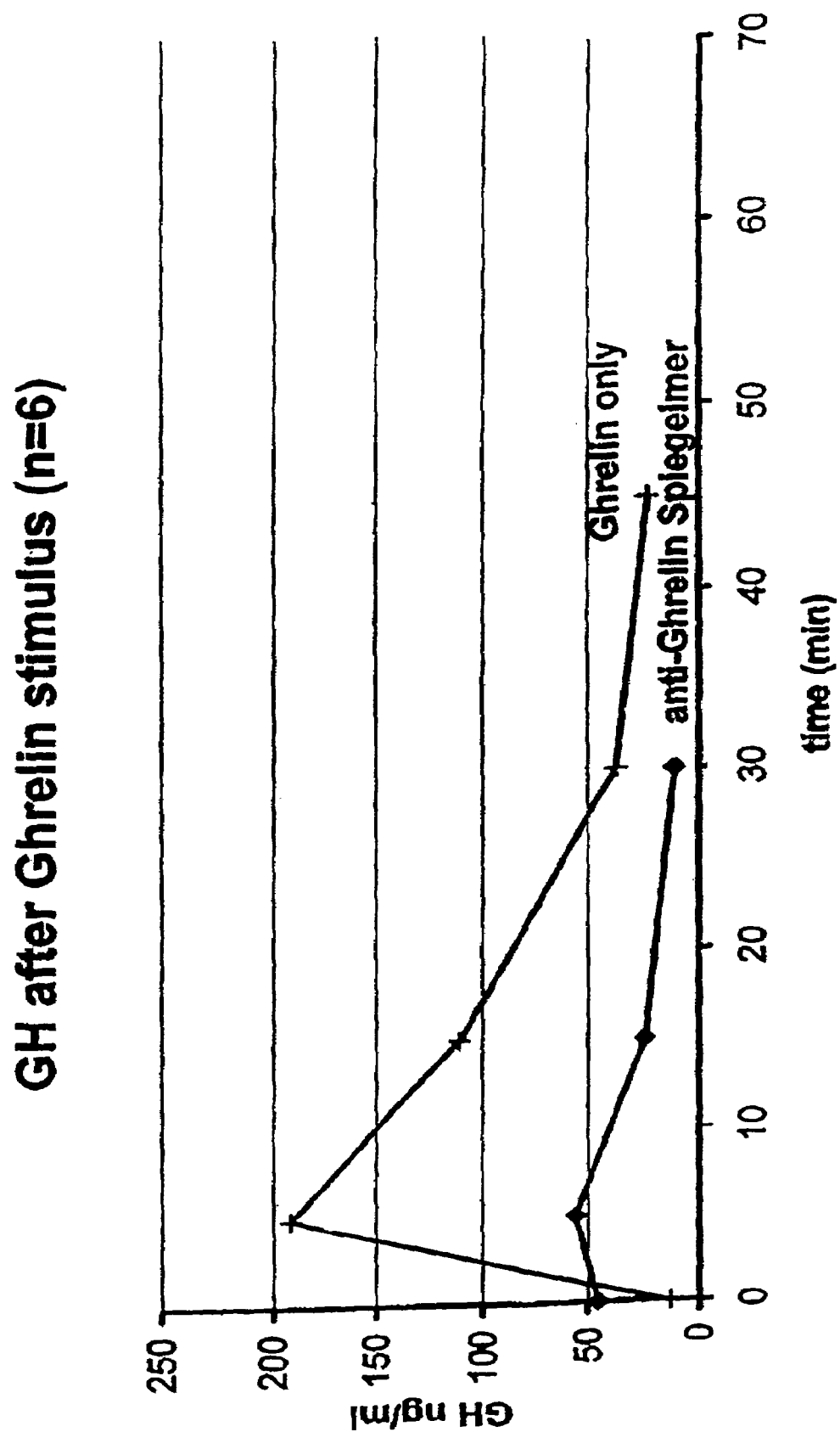
Figure 44:
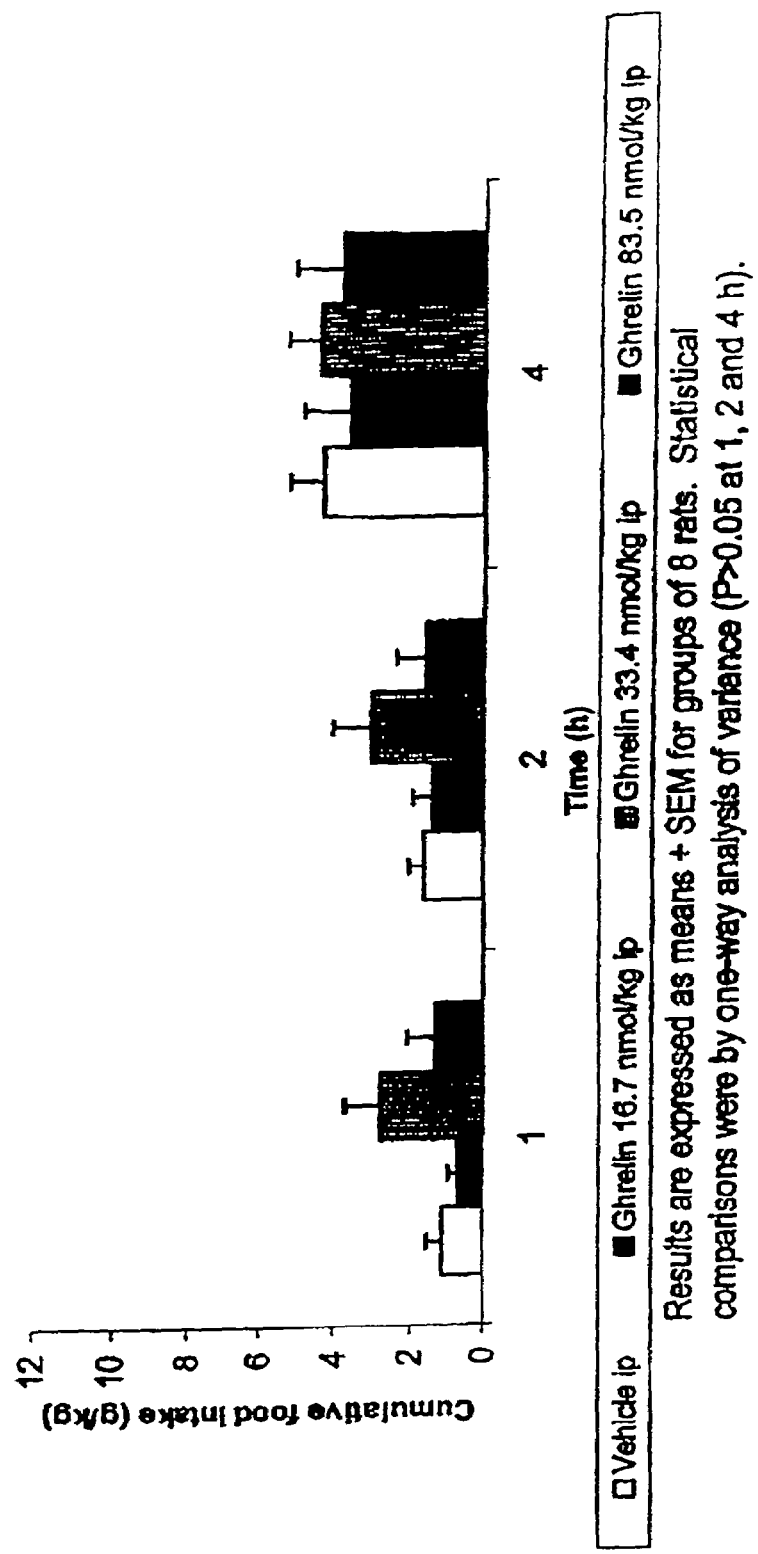

FIG. 8A shows table 4 indicating double rounds and binding assays performed from round 12 to 14 for the 2'F-RNA selection, data in percent binding to ghrelin, * marks sequences;

FIG. 8B shows an improvement of the 2'F-RNA pool binding to D-ghrelin monitored over the double rounds;

FIG. 9 shows the course of an automated in vitro selection against rat D-ghrelin;

FIG. 10 shows a worksurface of the robot for the automated in vitro selection of RNA;

FIG. 11 shows a scheme demonstrating the working procedure executed by the robot during the automated RNA selection;

FIG. 12 shows table 5 indicating the occurrence of identical sequences during the selection process; internal reference and SEQ.ID.No. are given;

FIG. 13 shows an alignment of sequences of RNA ligands, which were isolated by automated in vitro selection against ghrelin as described in example 2, whereby lines indicate missing nucleotides;

FIG. 14 A shows a binding curve of D-ghrelin binding RNA clone A8, which was isolated by automated in vitro selection, binding behaviour was analysed using bead assays;

FIG. 14 B shows a binding curve of D-ghrelin binding RNA clone B 11, which was isolated by automated in vitro selection, binding behaviour was analysed using bead assays;

FIG. 14 C shows a binding curve of D-ghrelin binding RNA clone C11, which was isolated by automated in vitro selection, binding behaviour was analysed using bead assays;

FIG. 14 D shows a binding curve of D-ghrelin binding RNA clone C12, which was isolated by automated in vitro selection, binding behaviour was analysed using bead assays;

FIG. 14 E shows a binding curve of D-ghrelin binding RNA clone F12, which was isolated by automated in vitro selection, binding behaviour was analysed using bead assays;

FIG. 15 shows table 6 indicating the binding behaviour of clones B 11, F 12 and E3 to D-ghrelin, which were isolated by automated in vitro selection;

FIG. 16 A shows a binding curve, activity and Kd of D-ghrelin binding RNA clone B 11, which was isolated by automated in vitro selection, corresponding data are shown in FIG. 8;

FIG. 16 B shows a binding curve, activity and Kd of D-ghrelin binding RNA clone F12, which was isolated by automated in vitro selection, corresponding data are shown in FIG. 8;

FIG. 16 C shows a binding curve, activity and Kd of D-ghrelin binding RNA clone E3, which was isolated by automated in vitro selection, corresponding data are shown in FIG. 8;

FIG. 17 shows table 7 indicating the Kd values of D-ghrelin binding RNA clones A3, A8, A12, B7, B11, B12, C11, C12, E3, E12, F5, F12, G2 and G5 as determined using the Biacore 2000 instrument;

FIG. 18 shows a competition experiment with clone B11, which was performed using the Biacore 2000 instrument;

FIG. 19 shows calculated secondary structures of D-ghrelin binding RNA spiegelmers clone B11 (SEQ ID NO:7) and of the truncated clone B11 trc (SEQ ID NO:37), the secondary structure was calculated with the program "rnafold" (Hofacker et al, 1994, Monatsh. Chem 125:167-188);

FIG. 20 shows table 8 indicating the Kd of RNA clones B 11 in the L-form and the truncated clone B 11 in D- and L-form, Kd was measured with Biacore 2000 instrument;

FIG. 21 shows Biacore 2000 assisted binding assays of RNA clones B 11 in the D-form and the truncated clone B11 in D- and L-form;

FIG. 22 shows an alignment of sequences of RNA ligands, which were isolated by manual in vitro selection against ghrelin as described in example 1 (round 13), whereby lines indicate missing nucleotides and the primer parts of the sequences are printed in bold and whereby the Ts are to be understood as Us;

FIG. 23 shows an alignment of sequences of RNA ligands, which were isolated by manual in vitro selection against ghrelin as described in example 1 (round 14), whereby lines indicate missing nucleotides and the primer parts of the sequences are printed in bold and whereby the Ts are to be understood as Us;

FIG. 24 shows an alignment of sequences of 2'-F-RNA ligands, which were isolated by manual in vitro selection against ghrelin as described in example 1 (round 14), whereby lines indicate missing nucleotides and the primer parts of the sequences are printed in bold and whereby the Ts are to be understood as Us;

FIG. 25 shows an alignment of sequences of 2'-F-RNA ligands, which were isolated by manual in vitro selection against ghrelin as described in example 1 (round 15), whereby lines indicate missing nucleotides and the primer parts of the sequences are printed in bold and whereby the Ts are to be understood as Us;

FIG. 26 shows the time course of fluorescence signals obtained after stimulation of CHO cells stably expressing the human ghrelin receptor (GHSR1) with 33 nM ghrelin; cells were loaded with the $Ca^{++}$-indicator dye Fluo4 and fluorescence signals were recorded with a fluorescence plate reader; at the end of the recording, Triton-X100 was added to check proper dye-loading of the cells;

FIG. 27 shows a dose-response curve for ghrelin-induced $Ca^{++}$-release in CHO cells stably expressing the human ghrelin receptor; plotting the difference between the maximal and the baseline signals against the ghrelin concentrations used for stimulation, a dose-response curve for ghrelin was obtained, indicating a half effective concentration ($EC_{50}$) of about 5 nM—this concentration was used for the further experiments on inhibition of $Ca^{++}$-release by Spiegelmers;

FIG. 28 shows a dose-response curve for the inhibition of ghrelin-induced $Ca^{++}$-release by Spiegelmer B 11 at room temperature; cells were stimulated with 5 nM ghrelin or ghrelin preincubated at room temperature with various amounts of Spiegelmer B11; the results show the percentage of fluorescence signal normalized to the signal obtained with no Spiegelmer; Spiegelmer B11 was found to inhibit ghrelin-induced $Ca^{++}$-release with an $IC_{50}$ of about 5 nM;

FIG. 29 shows a dose-response curve for the inhibition of ghrelin-induced $Ca^{++}$-release by Spiegelmer B 11 at room temperature; cells were stimulated with 5 nM ghrelin or ghrelin preincubated at 37° C. with various amounts of Spiegelmer B 11; the results show the percentage of fluorescence signal normalized to the signal obtained with no Spiegelmer; Spiegelmer B11 was found to inhibit ghrelin-induced $Ca^{++}$-release at 37° C. with an $IC_{50}$ of about 6 nM;

FIG. 30 shows a comparison of the inhibition of ghrelin-induced $Ca^{++}$-release by Spiegelmers B11 and C12; cells were stimulated with 5 nM ghrelin or ghrelin preincubated at room temperature with various amounts of Spiegelmer B11 or Spiegelmer C12; the results show the percentage of fluorescence signal normalized to the signal obtained with no Spiegelmer; in this experiment Spiegelmer B11 was found to inhibit ghrelin-induced $Ca^{++}$-release with an $IC_{50}$ of about 8 nM, whereas for Spiegelmer C12 the $IC_{50}$ was about 4 nM;

FIG. 31 shows the nucleotide sequences of clones resulting from the automated reselection,

```
                                          (SEQ ID NO: 126)
5'-X-, 5' primer sequence GGAGCUCAGACUUAGCA, (SEQ ID NO: 127)
3'-Y-, 3' primer sequence AUCGAGUGUCGGUUCCAC,
``` whereby the Ts are to be understood as Us, sequences that are underlined are thought to form an intramolecular helical structure, the core forms of the clones begin and end with the underlined sequences, clone SOT-108-H3 occurred 5 times, SOT-108-A6, SOT-108-B7, SOT-108-C2, SOT-108-C3 and SOT-108-D4 occurred twice, all other clones were obtained only once;

FIGS. 32 A-C show Biacore 2000 assisted binding assays of aptamers from the reselection pool to bio-D-Ghrelin at 37° C.;

FIG. 33 shows the sequences of reselection-Spiegelmers tested in cell assays; whereby the Ts are to be understood as Us, the sequence, the name, and the size of the Spiegelmers are indicated, as well as the name of the reselection clone it is derived from;

FIG. 34 shows the inhibitory activity of Spiegelmers on Ghrelin-induced calcium release in cell assays; the results are combined from three independent measurements, with the controls NOX-SOT-C (B11) and NOX-SOT-D (C 12) given for each of them (all Spiegelmers were analysed in duplicates at concentrations of 3 nM and 10 nM);

FIG. 35 shows the dose-response curve of the Spiegelmers NOX-SOT-C (B11), sot_d_lr_054, sot_d_lr_056, and sot_d_lr_064; the inhibition of ghrelin-induced calcium release by each Spiegelmer is measured in duplicate;

FIGS. 36 A-38 B show the food intake of mice following the administration of either saline solution, a non-active control Spiegelmer, or the PEGylated B11 Spiegelmer by i.v. injection;

FIGS. 39-40 show the food intake of mice following the administration of either saline solution, a non-active control Spiegelmer, or the PEGylated B 11 Spiegelmer by i.v. injection; mice were trained to have access to food only twice during the dark phase for the period of 1 hour; the experiment with a total of 24 animals was split in two sets of 12 animals, FIG. 39 shows the food intake of 12 animals in the first experiment and FIG. 40 shows the second experiment;

FIG. 41 summarizes the data shown in FIGS. 39-40, the total food intake of all 24 mice is shown;

FIG. 42 shows the 24-hour food intake of rats after icv administration of either saline solution, a non-active control Spiegelmer, or the PEGylated B11 Spiegelmer;

FIG. 43 shows the inhibition of Growth hormone release after exogenous Ghrelin administration by a single i.v. injection of 150 nmol/rat anti-Ghrelin Spiegelmer;

FIG. 44 shows the effects of single i.p. administration of Ghrelin (16,7 nmol/kg, 33,4 nmol/kg, 83,5 nmol/kg, respectively) on food intake in rats; and FIG. 45 shows the effect of different doses of anti-ghrelin spiegelmer on ghrelin-stimulated GH-release in rats; GH-release was induced with a single intravenous dose of 3 nmoles of ghrelin (A), and the ghrelin-induced release of GH was suppressed by prior intravenous administration of 15 nmoles (C) and 30 nmoles (D) of anti-ghrelin spiegelmer, but not with 3 nmoles of anti-ghrelin spiegelmer (B).

The following table links the SEQ ID Nos to the various clones and identifiers, respectively, described herein. It is to be understood that the clones B11 to G5 exist in two different forms. The form referred to herein as 'complete' comprises the randomised stretch of the pool used, or part thereof and the DE.40F primer sequence and the DE.40R primer, whereas the form referred to herein as 'core' is the minimum binding motive which was generated from the respective complete form. If not indicated to the contrary the strands represented are the (+) strands and the nucleic acid used 2'OH RNA.

TABLE

| Clone/Identifier | Seq. ID No |
|---|---|
| Rat ghrelin | 1 |
| RNA-Pool | 2 |
| Rev. Compl. | 3 |
| DE.40T7 | 4 |
| DE.40R | 5 |
| DNA pool | 6 |
| B11 (complete) | 7 |
| B11 (core) | 8 |
| G2 (complete) | 9 |
| G2 (core) | 10 |
| E12 (complete) | 11 |
| E12 (core) | 12 |
| B7 (complete) | 13 |
| B7 (core) | 14 |
| A8 (complete) | 15 |
| A8 (core) | 16 |
| B12 (complete) | 17 |
| B12 (core) | 18 |
| E3 (complete) | 19 |
| E3 (core) | 20 |
| C12 (complete) | 21 |
| C12 (core) | 22 |
| C11 (complete) | 23 |
| C11 (core) | 24 |
| A3 (complete) | 25 |
| A3 (core) | 26 |
| F5 (complete) | 27 |
| F5 (core) | 28 |
| A12 (complete) | 29 |
| A12 (core) | 30 |
| F12 (complete) | 31 |
| F12 (core) | 32 |
| G5 (complete) | 33 |
| G5 (core) | 34 |
| DE.40F-Primer (consensus sequence pf the pool) | 35 |
| DE.40R-Primer (consensus sequence of the pool) | 36 |
| B11trc | 37 |
| RNA round 13 group1 1.1 main clone 'SOT-R04-DR13-E5 | 38 |
| Group2 2.1 main clone 'SOT-R04-DR13-A2 | 39 |
| variations of 2.1 'SOT-R04-DR13-C4 | 40 |
| group3 3.1 main clone 'SOT-R04-DR13-C1 | 41 |
| group4 4.1 main clone 'SOT-R04-DR13-G2 | 42 |
| RNA round 14 group1 1.1 (main clone) 'SOT-R04-DR14-F7 | 43 |
| variations of clone 1.1 1.2 'SOT-R04-DR14-C11 | 44 |
| 1.3 'SOT-R04-DR14-A8 | 45 |
| 1.4 'SOT-R04-DR14-C12 | 46 |
| group3 3.1 (main clone) 'SOT-R04-DR14-C7 | 47 |
| variations of clone 3.1 1.2 'SOT-R04-DR14-E11 | 48 |
| 1.3 'SOT-R04-DR14-H11 | 49 |
| 1.4 'SOT-R04-DR14-E8 | 50 |
| 2'-F-RNA round 14 group1 1.1 (main clone) 'SOT-F03-DR14-G6 | 51 |
| mutations of clone 1.1 1.2 'SOT-F03-DR14-F2 | 52 |
| 1.3 'SOT-F03-DR14-F4. | 53 |
| 1.4 'SOT-F03-DR14-D5 | 54 |
| 1.6 'SOT-F03-DR14-G3 | 55 |
| 1.7 'SOT-F03-DR14-B5 | 56 |
| 1.8 'SOT-F03-DR14-C2 | 57 |
| 1.9 'SOT-F03-DR14-F3 | 58 |
| 1.10 'SOT-F03-DR14-B6 | 59 |
| 1.11 'SOT-F03-DR14-H1 | 60 |
| 1.12 'SOT-F03-DR14-F6 | 61 |
| 1.13 'SOT-F03-DR14-B1 | 62 |
| 1.14 'SOT-F03-DR14-C1 | 63 |
| 1.15 'SOT-F03-DR14-H5 | 64 |
| group2 2.1 (main clone) 'SOT-F03-DR14-G5 | 65 |
| variations of clone 2.1 2.2 'SOT-F03-DR14-D3 | 66 |
| 2.3 'SOT-F03-DR14-H2 | 67 |
| 2.4 'SOT-F03-DR14-D1 | 68 |
| 2.5 'SOT-F03-DR14-A2 | 69 |
| 2.6 'SOT-F03-DR14-G2 | 70 |
| group3 3.1 main clone 'SOT-F03-DR14-H6 | 71 |
| 2'-F-RNA round 15 group1 1.1 (main clone) 'SOT-F03-DR15-G10 | 72 |
| 1.2 'SOT-F03-DR15-G7 | 73 |

TABLE-continued

| Clone/Identifier | Seq. ID No |
|---|---|
| 1.3 'SOT-F03-DR15-F10 | 74 |
| 1.4 'SOT-F03-DR15-D9 | 75 |
| 1.5 'SOT-F03-DR15-F12 | 76 |
| 'SOT-F03-DR15-G12 | 77 |
| 1.6 'SOT-F03-DR15-H7 | 78 |
| 1.7 'SOT-F03-DR15-A11 | 79 |
| 1.8 'SOT-F03-DR15-A8 | 80 |
| 1.9 'SOT-F03-DR15-F8 | 81 |
| 1.10 'SOT-F03-DR15-C9 | 82 |
| 1.11 'SOT-F03-DR15-C12 | 83 |
| 1.12 'SOT-F03-DR15-F7 | 84 |
| 1.13 'SOT-F03-DR15-A12 | 85 |
| 'SOT-F03-DR15-C7 | 86 |

EXAMPLE 1

Manual In Vitro Selection

Target Molecule

Biotinylated rat D-ghrelin (amino acid sequence, H-Gly-Ser-Ser(octanoyl)-Phe-Leu-Ser-Pro-Glu-His-Gln-Lys-Ala-Gln-Gln-Arg-Lys-Glu-Ser-Lys-Lys-Pro-Pro-Ala-Lys-Leu-Gln-Pro-Arg-OH) (SEQ ID NO: 1) was custom synthesized by Bachem (Basel, Switzerland). The peptide that was used during the selection contains a biotin moiety at the C terminus to enable partitioning from unbound nucleic acid species employing the biotin-NeutrAvidin interaction.

Selection Pool, Generation of a Start Pool

The selection pool DE.40 consists of a random region of 40 nucleotides, flanked by a T7-promoter-caryring 38nt-primer at the 5'-end and a 20nt reverse primer at the 3'-end. The T7 primer carries a transcription-initiating sequence followed by a forward primer sequence. The Forward primer starts with an guanosine-triplett to enhance the transcription efficiency.

DE.40-Pool: (Corrected for RNA)

```
RNA-Pool:                                (SEQ ID NO: 2)
5'-GGA GCT CAG ACT TCA CTC G TG-N40-CA CGT ACC ACT
GTC GGT TCC AC-3'

Rev. Compl.:                             (SEQ ID NO: 3)
5'-GTG GAA CCG ACA GTG GTA CG TG-N40-CA CGA GTG
AAG TCT GAG CTC C-3'

DE.40T7:                                 (SEQ ID NO: 4)
5'-TCT AAT ACG ACT CAC TAT AGG AGC TCA GAC TTC ACT
CG-3'

DE.40R:                                  (SEQ ID NO: 5)
5'-GTG GAA CCG ACA GTG GTA CG-3'
```

(T7 promoter is underlined)

The annealing temperature was calculated theoretically and optimized afterwards by several experiments varying the temperature and time for annealing of the primer.

| | $T_m$ (° C.) | $T_p$ (° C.) | used (° C.) | |
|---|---|---|---|---|
| For | 56.1 | 68.72 | RNA | 2'-F-RNA |
| Rev | 56.9 | 68.72 | 63 | 63 |

$T_m$ = melting temperature, $T_p$ = 22 + 1.46 × [2 × (#GC) + (#AT)] (Wu et al.: DNA and Cell Biology 10, 233 (1991)); without T7-promotor-region The pool was chemically synthesized, the base composition determined and a complexity of 1×10E15 different molecules=1,78 nmol single-stranded DNA (ssDNA) were amplified by one-step PCR. For the 2-F-RNA start pool 1,78 nmol of the double stranded DNA were transcribed using 2'fluoro-modified pyrimidines (Trilink) using protocol 1; the RNA pool was transcibed using protocol 2 with non-modified nucleotides.

protocol 1. protocol for transcription with 2'-fluoro-modified pyrimidines

| component | stock concentration | 100 µl reaction |
|---|---|---|
| T7 Buffer (Epicentre) | 5× | 20 |
| DTT | 100 mM | 5 |
| Mn2+ | 25 mM | 10 |
| 2'-F-CTP | 100 mM | 3 |
| 2'-F-UTP | 100 mM | 3 |
| rATP | 100 mM | 1 |
| rGTP | 100 mM | 1 |
| PCR-Template | ca. 100 pmol/µl | 0.5 |
| T7-Polymerase | 5 U/µl | 2 |
| ddH2O | — | 54.5 | protocol 2. protocol for transcription with non-modified nucleotides

| component | stock concentration | 100 µl reaction |
|---|---|---|
| 80 mM HEPES/KOH (pH 7.5) 22 mM MgCl₂ 1 mM spermidine 10 mM DTT 4 mM NTPs (i.e. each) 10 µl/ml Rnase-out (Invitrogen) 120 µg/ml BSA 5M Betain 2 µl/ml T7 RNA polymerase (=100 U) α-[32P]-ATP α-[32P]-GTP Template water (add to 100 µl) | 10× transcription-buffer 100 mM DTT 10 mM NTP-mix Rnase-Out (40 U/µl) 2 mg/ml BSA 0.75M Betain T7-RNA polymerase (100 U) 50-100 pmol | 10 µl 10 µl 40 µl 1 µl 6 µl 15 µl 2 µl 1 µl 1 µl 7.5 µl 6.5 µl |

In Vitro Selection of Rat D-Ghrelin Binding Aptamers

Selections Buffer

The selection buffer used during the whole selection was according to physiological conditions in human blood (20 mM Hepes, 150 mM NaCl, 5 mM KCl, 1 mM MgCl₂ und 1 mM CaCl₂). The pH 7.4 was adjusted at 37° C.

Selection and Stringency

Selection of D-ghrelin ('target') binding aptamers was carried out using a 2'-fluoro modifed DE.40 pool (2F-RNA) and a non-modified RNA pool (RNA). Binding of the pool to the target took place in solution for 2 hours (10 µM-10 nM of peptide) and for 12 hours (10 nM-500 pM). The immobilization of the peptide-RNA complexes was performed using the steptavidin/neutravidin-biotin system. The biotinylated peptide was incubated with neutravidin derivated agarose or streptavidin linked polyacrylamid (s.c. ultralink) for 10 min at 37° C. and separated by short centrifugation. Afterwards the matrix was washed with selection buffer to remove non-bound and weakly binding pool. A matrix switch every two rounds was performed (starting with neutravidin-agarose) to avoid the generation of bivalent aptamers, which require the matrix for binding to the target with high affinity. Elution of the bound RNA and 2' F-RNA was accomplished by denaturing the peptide-RNA complexes with 4M guanidinthiocyanate in two steps (37° C., 65° C.) for 10 min in a shaker. From round 13 on a third elution step was carried out at 95° C. The eluted RNA or 2' F-RNA was extracted with phenol-chlorform to remove the peptide, precipitated with iso-propanol and amplified by PCR.

Folding of the RNA/2'FRNA

To avoid a bivalent independent folding of the aptamer the denaturation and renaturation on ice was performed in the absence of Mg2+ and Ca2+. The pools were denatured for 5 min at 95° C. in a PCR Cycler and snap cooled on crushed ice for 2 min. Afterwards Tween 20 (final concentration 0,1%) and the bivalent cat ions were added from a 10 fold mix and incubated for further 10 min at 37° C. The reaction was directly added to the precolumn.

Precolumn

The pool RNA is incubated with the pure matrix before adding the peptide to the solution. This is performed to avoid the enrichment of matrix binding aptamers. The matrix volume of the precolumn was alwalys the same volume of the main column used for separating RNA-peptide complexes from unbound species. The pure matrix was incubated for 10-15 min at 37° C. in a shaker together with the folded DE.40 pool, non-bound pool was removed and directly added to the ghrelin binding reaction in solution.

Binding in Solution and Immobilization of the Complex

Biotinylated D-ghrelin with a certain concentration was directly added to the pool after removing it from the precolumn. The gradient of the peptide concentration used for the selections with RNA and 2' F-RNA are displayed in FIG. 4A and FIG. 4B. The immobilization of the bio-ghrelin bound RNA complex was carried out by direct addition of the matrix to the binding reaction and incubation for 10 min at 37° C. in a thermoshaker at 800 rpm.

Partitioning

The immobilized complex was washed several times with pre-warmed selection buffer to remove unbound and weakly binding molecules. Washing steps were performed with 5×100 μl and from round 13 on with 5×1000 μl selection buffer.

Elution of Bound Molecules

The elution of bound RNA and 2F'RNA was accomplished by denaturing the peptide-RNA complex with 4M guanidinthiocyanate in two steps (37° C., 65° C.) for 10 min in a shaker. From round 13 on, a third elution step at 95° C. was carried out. The course of the eluted RNA and 2'-F-RNA in percent to total nucleic acid used in each selection round is shown in FIG. 5 and FIG. 6. To distinguish between background signal and a ghrelin mediated signal, a control column (without adding any peptide) was performed every round. The signal on the control column was defined as noise or background signal. The ration of the ghrelin mediated signal to noise signal is displayed in FIG. 1 and FIG. 2. Every time the signal to noise ratio increases the stringency was increased by decreasing target concentration in the following selection round. Afterwards the peptide concentration was kept at a constant level until another increase in the signal-noise ratio at the distinct peptide concentation was achieved.

The increase of the ratio is a clue for the enrichment of binding aptamers at a certain peptide concentration. The eluted RNA or 2'-F-RNA was extracted with phenol-chloroform to remove the peptide, precipitated with iso-propanol and amplified by PCR.

Double Rounds and Binding Tests

A double round describes the process of two subsequent selection rounds without amplification. The first selection round s.c. collection round (CR) is used to collect all D-ghrelin binding aptamers at a relatively high concentration of the target to get rid of non binding aptamers. After elution and extraction of bound RNA/2-F-RNA the eluted nucleic acid is used for the next round without amplifying it. This round is called double round (DR) and is normally performed at a very low concentration of the target. This process of selection is used to eliminate the pressure of ampflification and folding/refolding of the aptamer. In these selections 3 double rounds were perfomed (round 12, 13, 14 for RNA and round 14, 15, 16 for 2'-F-RNA). Before every collection round (CR) a "test for binding" over a wide range of target concentration was carried out to evaluate the best target concentration to collect the aptamers. This test is also used to monitor the improvement of the pool enrichment from round to round. The results of these double rounds and test for binding are displayed in FIGS. 7A, 7B, 8A and 8B.

Amplification

Exraction and Precipitation

The eluted RNA or 2F' RNA was purified by phenol-chloroform extraction and precipitated with 2 μl glycogen as a carrier, 0,3M natriumacetat pH 5,5 and 1 volume of ice-cold isopropanol for 20-30 min at −20° C.

Reverse Transcription (RT)

The precipitated RNA/2' F-RNA was translated into single stranded DNA by using reverse transcriptase. Not more than 5 pmol template per 30 μl reaction were denatured together with the reverse primer for 5 min at 95° C. in 0,8M betain, the reverse primer was annealed on ice for 5 min, reaction buffer and nucleotides were added and the reaction was heated for 2 min at 48° C. before 5 units of reverse transcriptase were added. The reaction took place with a temperature gradient (30 min 48° C., 50° C. 20 min, 55° C. 10 min, 70° C. 15 min) in a thermocycler.

Polymerase Chain Reaction(PCR)

Three 10 μl aliquots of the RT-reaction was used as a template for the PCR reaction. The components for reaction were added as followed:

| Component | Stock concentration | 100 μl total |
|---|---|---|
| PCR-Puffer (Gibco) | 10× | 10 |
| MgCl2 | 50 mM | 5 |
| dNTP-Mix (A, T, G, C) | 10 mM je NTP | 2.5 |
| T7-Primer | 100 mM | 3 |
| reverse-Primer | 100 mM | 3 |
| Template (aus RT) | 1-5 pmol/100 μl | 10 |
| Betain | 5M | 15 |
| Taq-Polymerase (Gibco) | — | 1 |
| ddH20 | — | adjust to 100 μl |

Between 8-12 cycles of the following program were performed in a PCR cycler
denaturation 95° C.: 1 min
annealing 63° C.: 1 min
elongation 72° C.: 1 min An aliquot of the reaction was analysed on a polyacrylamide gel. The PCR reaction was precipitated afterwards with 1 µl glycogen, 0,3M sodium acetate pH 5.5 and 3 volumes of ice-cold 100% ethanol for 20-30 min at −80° C. The pellets was resuspended in water and 50-100 pmol were used as template for in vitro transcription.

2'-Fluoro Transcription 50-100 pmol dsDNA were used as template for in vitro transcription. The conditions were like described above for the generation of the start pool. The generated RNA is used for the next selection round. The amount used each round is mentioned in FIG. 3.

The results of this selection are depicted in FIG. 22 and FIG. 23 for the selection using the RNA pool, and in FIGS. 24 and 25 using the F' RNA pool. It is to be understood that any of the sequences shown in said Figs. are nucleic acids according to the present invention, including those truncated forms thereof which, however, are still capable of binding to the target.

EXAMPLE 2

Automated In Vitro Selection

In the following the automated selection of specifically binding rat D-ghrelin binding aptamers will be described.

Materials.

Biotinylated rat D-ghrelin (amino acid sequence, H-Gly-Ser-Ser(octanoyl)-Phe-Leu-Ser-Pro-Glu-His-Gln-Lys-Ala-Gln-Gln-Arg-Lys-Glu-Ser-Lys-Lys-Pro-Pro-Ala-Lys-Leu-Gln-ProArg-OH) (SEQ ID NO:1) was custom synthesized by Bachem (Basel, Switzerland). The peptide that was used during the selection contains a biotin moiety at the C terminus to enable partitioning from unbound nucleic acid species employing the biotin-NeutrAvidin interaction. For this, NeutrAvidin agarose and NeutrAvidin UltraLink Plus (both Perbio Science, Bonn, Germany) were used. The OneStep RTPCR Kit was purchased from Qiagen (Hilden, Germany). Taq DNA Polymerase, Superscript II Reverse Transcriptase and RNaseOUT RNase inhibitor were from Life Technologies (Karlsruhe, Germany), T7 RNA polymerase from Stratagene (Amsterdam, The Netherlands), and DNase I from Sigma-Aldrich (Taufkirchen, Germany). PicoGreen double stranded DNA detection dye was purchased from Molecular Probes, NTPs from Larova (Teltow, Germany).

Pools, primers and RNA spiegelmers

```
                                             (SEQ ID NO: 6)
The sequence of the DNA pool was 5'-TCT AAT ACG
ACT CAC TAT AGG AGC TCA GAC TTC ACT CGT G-N40-CAC
GTA CCA CTG TCG GTT CCA C-3' with N symbolizing an
equimolar mixture of A, C, G, and T.

Forward (T7)-primer DE.40T7:        (SEQ ID NO: 4)
5'-TCT AAT ACG ACT CAC TAT AGG AGC TCA GAC TTC ACT
CG-3'.

Reverse primer DE.40R:              (SEQ ID NO: 5)
5'-GTG GAA CCG ACA GTG GTA CG-3'.
```

Cloning and sequencing of enriched pools was done by GATC (Konstanz, Germany).

Process of Automated In Vitro Selection

Most liquid handling manipulations during automated in vitro selection were done in 96-well plates with removable lids (NCC plates; Bilatec AG, Germany); partitioning of unbound from bound RNA species was done in Mobicol columns (MoBiTec AG, Germany); automated purification of in vitro transcripts was done using Microcon YM-30 ultrafiltration units (Millipore, Eschborn, Germany).

Input RNA Used for the Automated Selection

RNA for the first automated selection round (round 3) was the same as used in the third manual selection round (see Example 1). 250 pmoles of this RNA were used as input per binding reaction in round 3 and 4; 100 pmoles in every further round.

Denaturation of RNA

All non-enzymatic selection steps except denaturation of the RNA before contacting with the target molecule rat D-ghrelin were done in selection buffer (20 mM Tris-HCl, pH 7.4; 150 mM NaCl; 5 mM KCl; 1 mM $MgCl_2$; 1 mM $CaCl_2$; 0.1% [wt/vol] Tween-20). For denaturation, 100-250 pmol RNA pool were heated to 95° C. for 5 min in 57 µl selection buffer without $CaCl_2$ and $MgCl_2$. After denaturation, the RNA was quickly cooled to 4° C. for 2 minutes and then equilibrated at 37° C. $MgCl_2$ and $CaCl_2$ were added to final concentrations of 1 mM each and the mixture was incubated for further 5 min at 37° C. (folding of the RNA).

Partitioning of Bound from Unbound RNA

Following denaturation, the RNA was contacted for 15 minutes at 37° C. with 10 µl of the selection matrix (NeutrAvidin agarose or NeutrAvidin UltraLink, respectively) without peptide. This so-called pre-selection was designed to remove potential matrix binding RNA species from the mixture. In order to keep the matrix particles in suspension, the samples were shaken at 1,400 rpm (37° C.). The matrix was then separated from the RNA in solution by simple sedimentation, the supernatant was transferred to fresh wells, and rat D-ghrelin was added to concentrations as shown in FIG. 9. After 60 minutes at 37° C., 10 µl of the biotin-binding matrix was added and the binding reaction was incubated for further 10 minutes under shaking (1,400 rpm, 37° C.). For washing, the matrix was then transferred to Mobicol columns and washed with up to 135 matrix volumes of pre-warmed selection buffer (37° C.) to remove unbound from bound RNA species. Wash volumes varied between 45 (round 3, i.e. first automated round) and 135 matrix volumes in later rounds (see FIG. 9).

Elution of Bound RNA

Elution of bound RNA was done by resuspending the matrix particles with bound RNA in 95 µl of RT-PCR buffer and heating to 95° C. for 3 minutes. Enzymes for reverse transcription and following PCR were added after equilibration at 50° C. for 2 minutes. Buffer conditions and amount of enzymes were used as suggested by the supplier Qiagen.

Amplification

In vitro transcription—Generation of RNA for Use in the Selection Process

Transcriptions were conducted with 150 U T7 RNA polymerase and 40 U RNaseOut RNase inhibitor in T7 reaction buffer (80 mM HEPES pH 7.5; 22 mM $MgCl_2$; 1 mM spermidine; 10 mM dithiothreitol; 4 mM [each] GTP, CTP, ATP and UTP; 80 µg/ml BSA) in a volume of 150 µl. In one transcription reaction, 25 µl RT-PCR reaction was used as template for in vitro transcription. The reactions were incubated at 37° C. for 3 hours. Finally, DNase I was added to digest the template DNA and the reactions were incubated at 37° C. for 15 minutes. Precipitated inorganic pyrophosphate was then dissolved by adding EDTA to a final concentration of 25 mM on the 50° C. workstation. The generated RNA was separated from remaining NTPs and other undesired reaction components either via denaturing gels containing 8 M urea or by using ultrafiltration employing Microcon YM-30 microconcentrators. Ultrafiltration purified RNA was just rinsed from the ultrafiltration membrane, for gel purification the RNA bands were excised under UV light, the RNA eluted from the gel, ethanol precipitated, dried and resuspended in water.

Reverse Transcription and PCR of Selected RNAs

Reverse transcription of selected RNA molecules was done using the Qiagen OneStep RT-PCR kit under conditions as recommended by the supplier in presence of the NeutrAvidin Agarose or UltraLink Plus matrix in a volume of 120 µl. The samples (RT-PCR reaction buffer together with matrix and adherent RNA) were heated for 3 minutes at 95° C. and equilibrated at 50° C. for 2 minutes before adding the enzymes. For reverse transcription, the reactions were kept at 50° C. for 20 minutes and 10 minutes at 60° C. Inactivation of RT enzymes as well as activation of the thermostable DNA polymerase was accomplished by incubation of the mixture at 95° C. for 15 minutes.

Thermocycling parameters were as follows: denaturing, 30 s at 95° C.; anealing, 30 s at 63° C.; polymerization, 30 s at 72° C.

Control of PCR Progress

In order to keep the number of PCR cycles to a minimum, the amount of double stranded DNA generated in the PCR was tracked semiquantitatively. The reaction was cycled only as long as enough template DNA for in vitro transcription had been generated. During the PCR, 3 µl-aliquots were sampled from the reactions after a given number of cycles and mixed with a PicoGreen solution (diluted 1:400 in TE buffer [10 mM Tris-HCl, pH 8; 1 mM EDTA]). PicoGreen is a fluorescent dye which shows almost no fluorescence when free in solution. If the dye, however, has bound to double stranded DNA, it fluoresces strongly (ex: 485 nm; em: 520 nm). Measurement of fluorescence in comparison with a control lacking the thermostable polymerase allows a quite exact estimation of PCR progress. After reaching the set threshold (fluorescence intensity with polymerase/fluorescence intensity without polymerase>2), an aliquot of the RT-PCR reaction was directly used as template for in vitro transcription.

Automated Manipulations

From round 3 on all manipulations except six gel purification steps were performed fully automated on a pipetting robot. The configuration of the modules used during the process is depicted in FIG. 10, the order of use of the modules was as shown in FIG. 11. The following modules were used during the selection process:

fluorescence reader for control of the amplification progress during PCR. Samples that had already generated sufficient amounts of dsDNA for in vitro transcription were intermediately stored at 4° C. and were not subjected to additional thermocycling double vacuum manifold with chamber A for partitioning and chamber B for purification of transcription reactions racks for disposable, conductive barrier tips thermocycler for running PCR programs as well as various incubation steps shaker for suspending particulate matrix in binding or reaction buffer 50° C. workstation for hot starts of enzymatic reactions or for keeping PCR reactions at elevated temperatures for taking samples during fluorescent measurements 4° C. workstation for intermediate storage of PCR or transcription reactions 4° C. reagent rack for storage of temperature sensitive reagents 37° C. reagent rack for storage and pre-warming of wash buffer 37° C. workstation for performing most pipetting steps fluoroplate workstation for preparing fluorescent measurement reactions hotel for storage of microtiter plates currently not in use waste station for disposal of used pipette tips The involvement of the modules in the context of this example as well as the order of participation during the process of automated in vitro selection is diagrammed in FIG. 11.

Results of the Selection

Course of the Selection

The course of the in vitro selection against rat D-ghrelin is depicted in FIG. 9. In every selection round, three binding reactions with different stringency plus one void column lacking the target molecule were performed. Stringency was adjusted by varying wash volumes as well as lowering the target concentration.

Selection rounds 1 and 2 were done manually, as the large amounts of RNA pool which are necessary to represent the desired pool complexity could not be handled safely by the robot. From round 3 on, the selection was done fully automated. Every two rounds, a decision was made which stringency should be used for the following two rounds.

In FIG. 9, that selection strand is highlighted which produced the sequences given in FIG. 13. Generally, the selected RNA of the most stringent strand (i.e. the one with the lowest target concentration or the greatest wash volume, respectively) which still showed significant signal relative to the background was used as input for the next round. The number of PCR cycles which was necessary to reach the threshold level (see "Control of PCR progress") was used as a measure. In total, 19 selection rounds—17 thereof automated—were performed.

The population of dsDNA molecules from round 17 and round 19 (each at 6.2 nM D-ghrelin) were cloned and sequenced. In total, 96 clones were sequenced (48 from round 17 and round 19, respectively). Frequencies and occurrence of the 14 different clones was as depicted in FIG. 12 (table 5).

Sequences

The result of the sequence analysis can be seen in FIG. 13. From the total of 96 clones, both primers could be found in 87.

It is to be understood that any of the sequences shown in FIG. 13. are nucleic acids according to the present invention, including those truncated forms thereof which, however, are still capable of binding to the target.

EXAMPLE 3

Characterization of RNA Aptamers to D-Ghrelin

Ranking of the Clones by Using the "Beadassay" (Binding in Solution)

All 14 clones which had been obtained from the automated in vitro selection against D-ghrelin were ranked in respect of their binding behaviour by using the beadassay.

For this purpose, 2 pmol (20 nM) RNA were denatured for 5 min at 95° C. in 100 µl selection buffer without $Ca^{++}$, $Mg^{++}$ and Tween 20 and subsequently snap cooled by directly putting on ice. Then $Ca^{++}$ and $Mg^{++}$ were added to a final concentration of 1 mM each and Tween 20 to a final concentration of 0,1%. The solution was equilibrated to 37° C.

This RNA was preincubated with different concentrations of biotinylated D-ghrelin for 1 h at 37° C. Then 40 µl of this solution were transferred into a microtiterplate and 30 µl of paramagnetic streptavidin magnetic particles ("beads"; Roche, 10 mg/ml) were added and the mixture incubated for 10 min at 37° C. to immobilise all biotinylated D-ghrelin on the beads (free peptide as well as RNA:peptide complexes). In order to monitor the decrease of RNA concentration in the supernatant in dependance of the D-ghrelin concentration, the amount of RNA in the supernatant was quantified using OliGreen fluorescent dye (Molecular Probes). Fluorescence of OliGreen is strongly dependent on binding of the molecule to oligonucleotides: when unbound in solution, OliGreen only shows weak fluorescence when excited with light of 485 nm. However, when nucleic acids are present, the fluorescent signal at 520 nm rises proportional to the concentration of the nucleic acid.

RNA-target complexes were then disrupted by resuspending the beads in 6 M urea and incubating for 10 min at 37° C. In order to monitor the increase of eluted RNA in dependance of target concentration, the amount of RNA in this eluate was quantified as well. All values were corrected for the background signal in the control without peptide. Representative binding curves for supernatant and eluate are depicted in FIG. 14A to E.

A first ranking using D-ghrelin concentrations of 0, 20, 100 and 500 nM showed that all clones tested bound similarly well with a $K_D$ of the active conformation of less than 100 nM. As judged from the decrease of the RNA concentration in the supernatant, about 40 to 50% of the RNA seems to be in the active conformation.

A more detailed ranking now deploying D-ghrelin concentrations of 0, 5, 10, 20, 50, 100, 200 and 400 nM for the clones B11, C11, C12, A8 and F 12 showed that all these clones bind with a $K_D$ of the active conformation of about 10 nM in this assay (FIG. 14A to E).

These figures show the increase of nucleic acid mediated fluorescence in dependance of concentration of biotinylated D-ghrelin. On the y-axis the increase of fluorescent signal [%] in the eluate relative to the background signal in the control without peptide (=0%) is depicted. The datapoints determined for clone A8 were fitted with a OneSiteBinding model using the formula $$y = \frac{B*x}{K+x}$$

$B_{max}$ is a value for the maximum plateau value for the increase of fluorescence at high peptide concentrations. $K_D$ shows the binding constant $K_D$ in [nM].

As binding constants below 10 nM can not be analysed with this assay, the binding properties of three selected clones were then characterized by a binding assay using radiolabeled RNA as well by the use of a Biacore 2000 instrument.

Ranking of Selected, Radiolabeled Clones in Respect of their Binding Behaviour

A ranking of the binding behaviour of 3 selected molecules towards the target molecule rat D-ghrelin was done. For this purpose, the clones B11, E3 and F12 were in vitro transcribed in the presence of $\alpha^{32}$P-GTP and $\alpha^{32}$P-ATP. 2-5 pmoles of the radiolabeled RNAs were denatured for 3 minutes at 95° C. in selection buffer without $Ca^{++}$ and $Mg^{++}$, folded by addition of these ions to a final concentration of 1 mM at 37° C., and incubated for 1 hour at 37° C. with biotinylated rat D-ghrelin in concentrations of 0, 3, 10, 30, 100, 300, 1000, and 3000 nM. Subsequently, a constant amount of NeutrAvidin agarose was added as matrix and the RNA:peptide complex was shaken at 37° C. for 10 more minutes. The matrix with bound peptide and peptide:RNA complexes was then separated, the supernatant was removed, and the difference between bound and unbound RNA was determined. From the calculated numbers, the control (0 nM D-ghrelin) was subtracted as background (FIG. 15, table 6). Binding curves with appendant numbers are depicted in FIG. 16 A to C.

Ranking of Clones by Using the Biacore 2000 Instrument

The biacore measurements of all 14 clones were performed as direct binding assays of RNA solution on a ghrelin-chip. The binding partners are free RNA and pre-immobilized ghrelin.

The ghrelin-chip consisted of a CM5 chip (Biacore) with 4 flowcells whose surface had been coupled with EDC/NHS-aminocoupling as follows:

Flowcell 1: 1265 RU of avidin as reference cell
Flowcell 2: 1270 RU of L-ghrelin (rat)
Flowcell 3: 740 RU of D-ghrelin (rat)
Flowcell 4: 600 RU of D-ghrelin (rat)

The samples to be tested were adjusted to a concentration 500 nM in selection buffer and equilibrated to 37° C. The measurement itself was performed on a Biacore 2000 instrument under the following conditions:

| | |
|---|---|
| Temperature | 37° C. |
| Flow | 20 µl/min |
| Association | 5 min |
| Dissociation | 5 min |
| Regeneration | 1M NaCl + 0.01% Triton X-100 |

It turned out that 13 out of the 14 tested D-RNAs had a $K_D$ in the range of 100 to 200 nM to amino-coupled D-ghrelin (FIG. 17). The D-RNA concentration of the C 12-preparation was much lower than for all others, which results in a much lower maximum signal. This makes interpretation difficult and the apparent low $K_D$ of about 20 nM is questionable.

Competition of Clones B11 with Free Rat D-Grelin

To assess the binding properties of clone D-B 111 for free rat D-ghrelin, a competition experiment was performed: A constant concentration of D-B11(100 nM) was preincubated with different concentrations of free D-ghrelin (0-500 nM) at 37° C. in selection buffer and then injected into the biacore. Immobilized ghrelin on the biacore chip and free ghrelin compete for the binding of the RNA which leads to a lower apparent concentration of RNA with increasing concentration of free ghrelin and thus to a lower biacore signal.

As shown in FIG. 18, the biacore signal decreases with increasing concentration of D-ghrelin in solution. This means that binding to immobilized D-ghrelin can be competed with free D-ghrelin.

EXAMPLE 4

Truncation of B11 and Characterization of the Spiegelmer

The secondary structure of aptamer B 11 was calculated by using the program rnafold (I. L. Hofacker et al., 1994. Monatsh. Chem 125: 167-188) as displayed in FIG. 19.

For production of RNA spiegelmers, it was necessary to truncate the B11 sequence in such a way that the resulting binding motif would allow chemical synthesis under reasonable efforts and affinity to ghrelin would not be lost.

In order to achieve this, bases 1 to 17 and 65 to 82 were deleted. The respective 47mer B11trc (for the calculated secondary structure by rnafold, see. FIG. 19) was produced as D-RNA enzymatically by synthesizing an ssDNA containing a T7 promoter sequence, filling in the ssDNA to transcribable dsDNA using a primer and Taq polymerase, and setting up a T7 RNA polymerase reaction with this template. The produced RNA was gel purified and dissolved in water. The corresponding spiegelmer was synthesized using standard β-cyanoethyl chemistry.

The truncated B 11 version were tested in both, the L- and the D-form as well as the full-length D-RNA on a Biacore 2000 instrument as described above in the same run and gave similar results for the $K_D$ between 100 and 200 nM (FIG. 20). An overlay of the biacore measurements of clone B11 (D-RNA) and truncated B 11 (D- and L-RNA, respectively) is shown in FIG. 21.

EXAMPLE 5

Method to Analyse the Inhibition of Ghrelin-Induced Calcium-Release by Ghrelin-Binding Spiegelmers Stable transfected CHO-cells expressing the human ghrelin receptor (GHS-R1a) (obtained from Euroscreen, Gosselies, Belgium) are seeded with $5-7 \times 10^4$ cells per well in a black 96 well-plate with clear bottom (Greiner) and cultivated overnight at 37° C. and 5% $CO_2$ in UltraCHO medium (Cambrex) which contained in addition 100 units/ml penicillin, 100 µg/ml streptomycin, 400 µg/ml geneticin and 2.5 µg/ml fungizone.

The Spiegelmers are incubated together with human or rat ghrelin (Bachem) in UltraCHO medium, containing 5 mM probenecid and 20 mM HEPES (CHO-U+) for 15 to 60 min at room temperature or 37° C. in a 0.2 ml low profile 96-tube plate.

Before loading with the calcium indicator dye fluo-4, cells are washed once with 200 µl CHO-U+. Then 50 µl of the indicator dye solution (10 µM fluo-4 (Molecular Probes), 0.08% pluronic 127 (Molecular Probes) in CHO-U+) are added and the cells are incubated for 60 min at 37° C. Thereafter cells are washed three times with 180 µl CHO-U+. Finally 90 µl CHO-U+ are added per well.

Measurement of fluorescence signals is done at an excitation wavelength of 485 nm and an emission wavelength of 520 nm in a Fluostar Optima multidetection plate reader (BMG), equipped with injection pumps.

To analyse the exact time course of the ghrelin-induced changes in calcium concentrations, the solutions for stimulation are prepared as 10x concentrated solutions in CHO-U+ and injected with the help of injection pumps. Each well is analysed separately in this kind of measurement. At the end of the recording from each well, 10 µl 1% Triton-X-100 are injected to control proper loading.

For parallel measurement of several samples, wells of one (perpendicular) row of a 96 well plate are recorded together. First three readings with a time lag of 4 sec are done for determination of the base line. Then the recording is interrupted and the plate is moved out of the instrument. Using a multi-channel pipette, 10 µl of the stimulation solution is added to the wells, then the plate is moved into the instrument again and the measurement is continued. In total 20 recordings with time intervals of 4 sec are performed.

For each well the difference between maximal fluorescence and base line value is determined and plotted against ghrelin concentration or, in the experiments on the inhibition of calcium release by Spiegelmers, against concentration of Spiegelmer.

EXAMPLE 6

Automated Reselection

In order to obtain RNA binders with improved binding affinities, a reselection on the basis of the ghrelin-binding aptamer C12 was performed. The sequence of the respective DNA pool was 5'-TCT AAT ACG ACT CAC TAT AGG AGC TCA GAC TTA GCA GGT GGG TGA GG caa aaa cgt aag acc gaa ggt aac cat t CCT ACC CAC CAT CGA GTG TCG GTT CCA C-3'(SEQ ID NO:128) with lower case letters symbolizing a mixture of the respective base at 34%, the three other bases at 22%. The forward primer DE2.T7 had the sequence 5'-TCT AAT ACG ACT CAC TAT AGG AGC TCA GAC TTA GCA GG-3'(SEQ ID NO:129), the reverse primer DE2.R had the sequence 5'-GTG GAA CCG ACA CTC GAT GG-3'(SEQ ID NO:130).

The first two selection rounds were done manually as described in Example 1 "Manual in vitro Selection"; rounds 3 to 10 were performed by the robot as described in Example 2 "Automated in vitro Selection".

The population of dsDNA molecules from round 10 (at 12 nM D-ghrelin) was cloned and sequenced. In total, 46 clones were sequenced. The nucleotide sequences of the 25 different clones for which binding properties were examined are depicted in FIG. 31.

EXAMPLE 7

Analysis of Individual Clones from Reselection 25 clones from the reselection pool (Example 6, FIG. 31) showing variations at different positions have been chosen for ranking using the "bead assay" described in Example 3. The binding of D-RNA aptamers was analysed at D-Ghrelin concentrations of 0, 10, 20, 50, 100, 200, 400, and 800 nM; as a reference, the aptamer NOX-SOT-D (C12) has been analysed in parallel. Several candidates were binding stronger to D-ghrelin than the control apatmer NOX-SOT-D (C 12), showing either a lower $K_D$ or a higher amount of the active conformation.

In addition, binding of these aptamers was analysed using the Biacore 2000 instrument (Example 3). It turned out, that all RNAs bind to bio-D-Ghrelin, although with deviations in the signal intensity, as well as the association and dissociation behaviour (see FIG. 32). The clones SOT-108-B1, SOT-108-C8, SOT-108-F2, SOT-108-B6, SOT-108-B7, SOT-108-D5, SOT-108-F7, SOT-108-G3, SOT-108-H4, SOT-108-E6, and SOT-108-C6 seem to have a better binding than the control clones NOX-SOT-C (B 11) and NOX-SOT-D (C 12), showing a higher signal in the measurement, or a slower dissociation rate. It has to be mentioned, that these clones were outstanding in the "bead assay" as well.

Therefore these clones have been tested for their activity as Spiegelmers in a cell culture assay (Example 5). At the same time, it was analysed, whether these sequences can be truncated to sizes below 50 nucleotides. The Spiegelmers tested are summarized in FIG. 33.

In a first set of cell assays, the inhibitory influence of the Spiegelmers on Ghrelin-dependent calcium release was detected at L-RNA concentrations of 10 nM and 3 nM, respectively. This allows a rough estimation of the biological activity of the truncated clones. Results of this two-point-measurements are given in FIG. 34.

Under cell assay conditions, these truncated reselection clones show an inhibitory activity comparable to that of NOX-SOT-D (C12). However, the Spiegelmers sot_d_lr_054, sot_d_lr_056, and sot_d_lr_064 inhibit Ghrelin activity at 3 nM and 10 nM significantly stronger, compared to the controls NOX-SOT-C (B 11) and NOX-SOT-D (C12).

A second set of experiments analyses the inhibitory activity of these Spiegelmers sot_d_lr_054, sot_d_lr_056, and sot_d_lr_064 at different concentrations of L-RNA (Example 5). The resulting dose-response curves are shown in FIG. 35. All clones showed nearly maximal inhibition of Ghrelin-induced calcium release at 10 nM. The apparent $IC_{50}$ can be detected at ~5 nM, while at Spiegelmer concentrations of 1 nM no response can be observed. In comparison, the $IC_{50}$ of NOX-SOT-C (B11) in this assay was detected above 10 nM.

It has to be considered, that the cell assay works at a Ghrelin concentration of 5 nM, which makes it difficult to analyse binding events with lower $IC_{50}$; complete inhibition can not be observed, when Spiegelmer is present in sub-stoichiometric amounts compared to Ghrelin. However, the almost complete inhibition of Ghrelin-activity at 10 nM indicates, that the biological activity of the Spiegelmers sot_d_lr_054, sot_d lr_056, and sot_d_lr_064 may even be better than detected.

EXAMPLE 8

Investigation of the Effect of i.v. Administered Anti-Ghrelin-Spiegelmer on Food Intake of Normal Mice Prior to the start of the study, mice (NMRI) were acclimatized for at least 5 days. The mice had free access to food and water and were housed individually. The experiment was carried out with 3 groups of 8 animals each. The groups received either saline solution, a non-active control Spiegelmer, or the PEGylated B 11 Spiegelmer by i.v. injection at the end of the light phase. The Spiegelmers were applied at a dose of 90 mg/kg (1,8 µM/kg). After administration the animals had unrestricted access to food and water and the food intake was recorded in intervals of five minutes for 24 hours. The experiment with a total of 24 animals was split in two sets of 12 animals each and was carried out at two different days.

Figure 37:
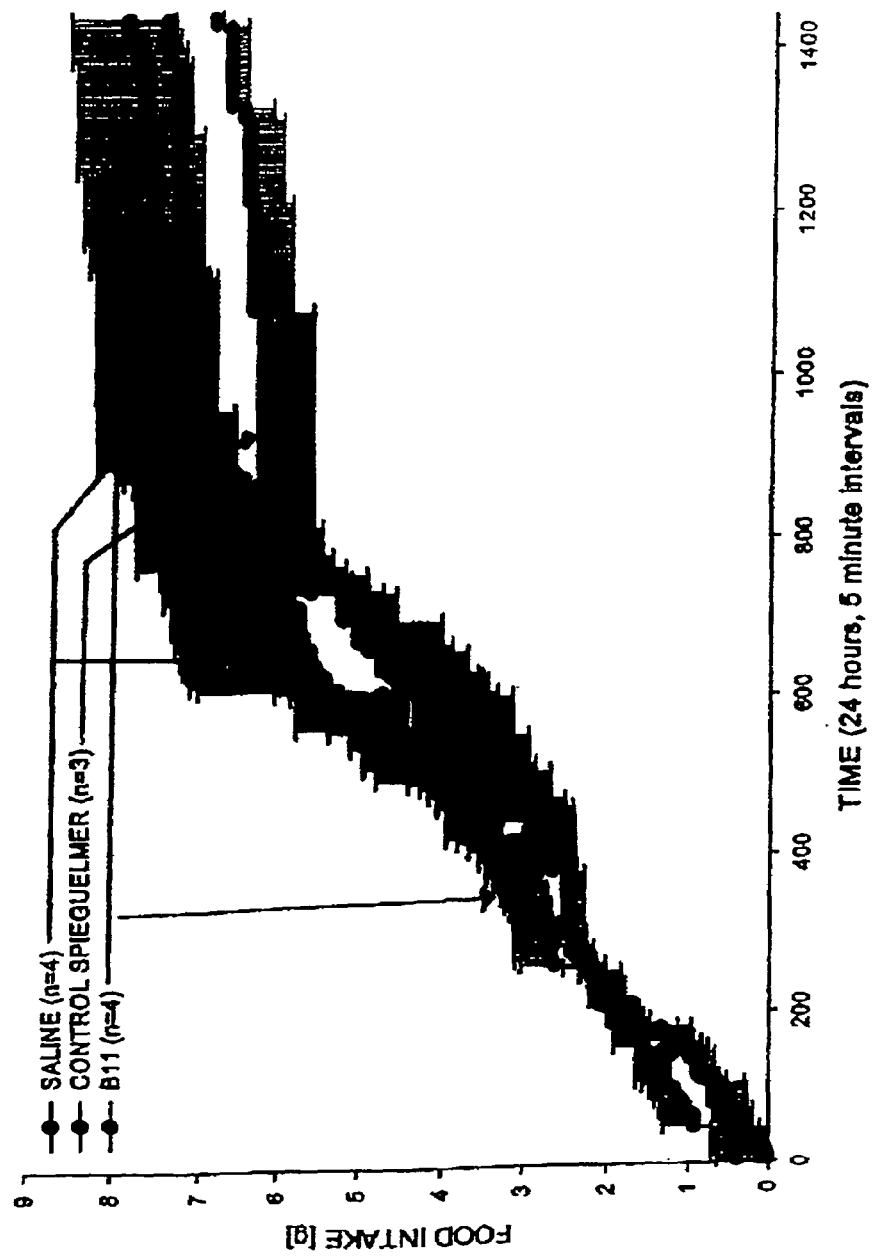
Figure 37:
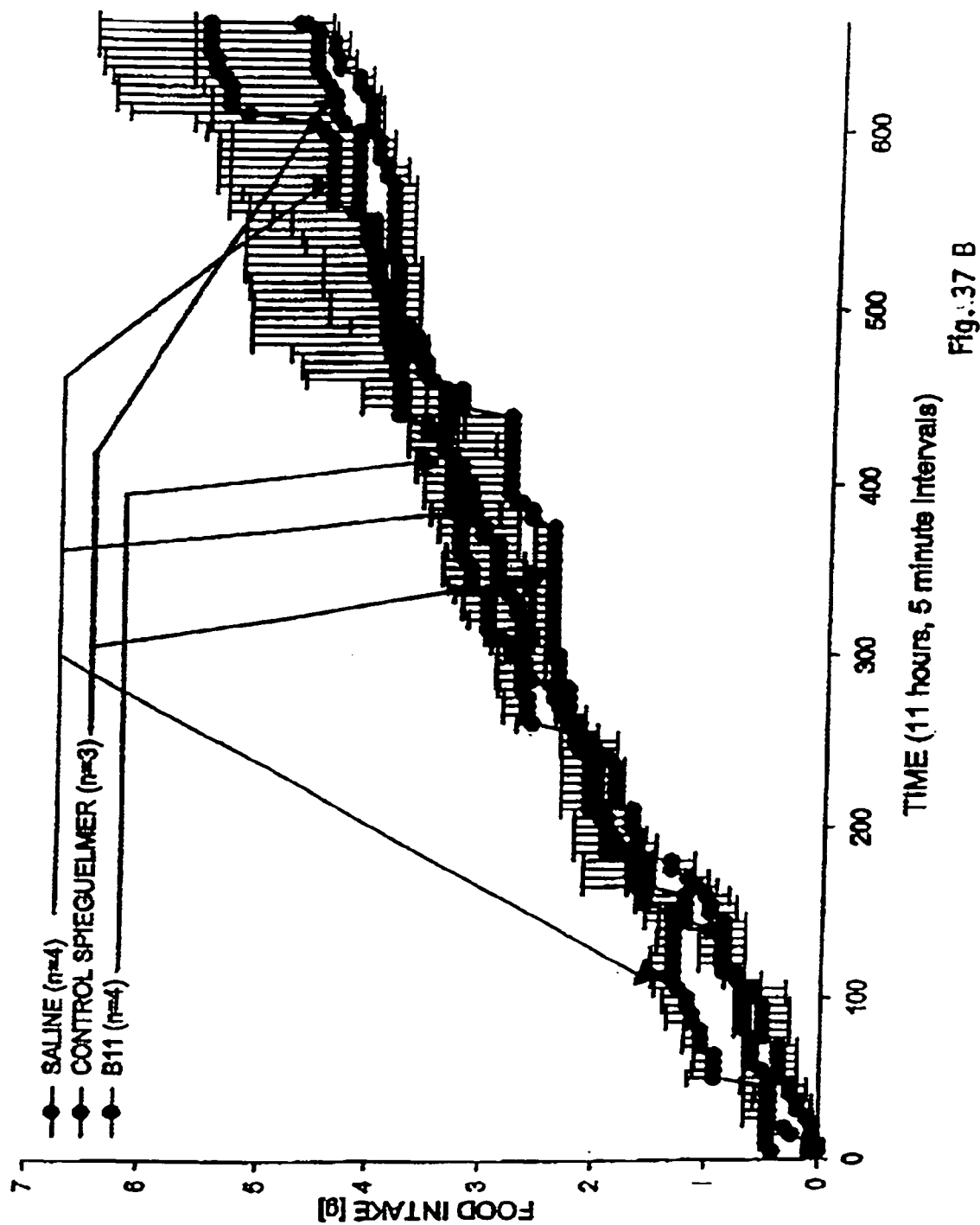
Figure 38:
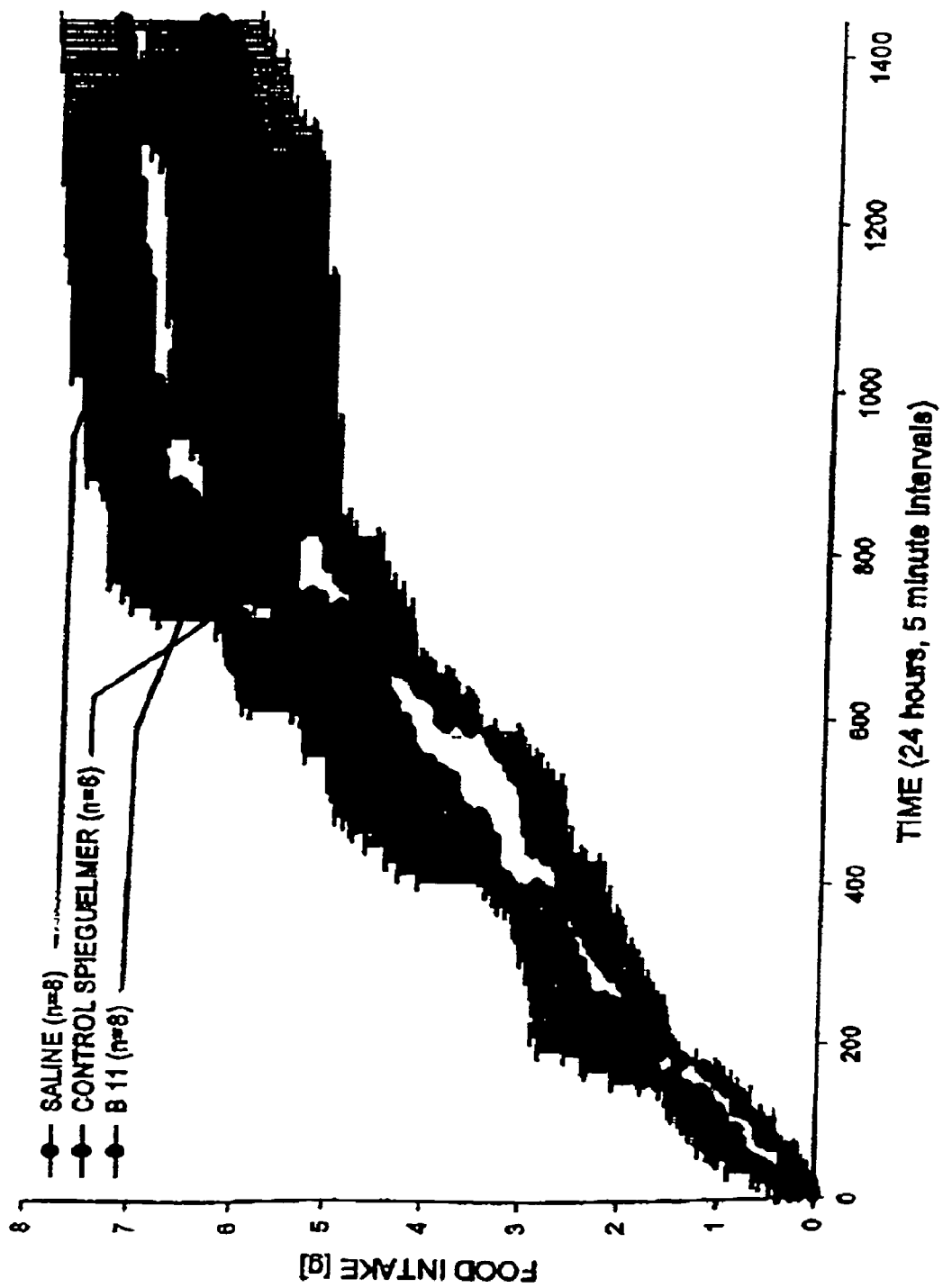
Figure 38:
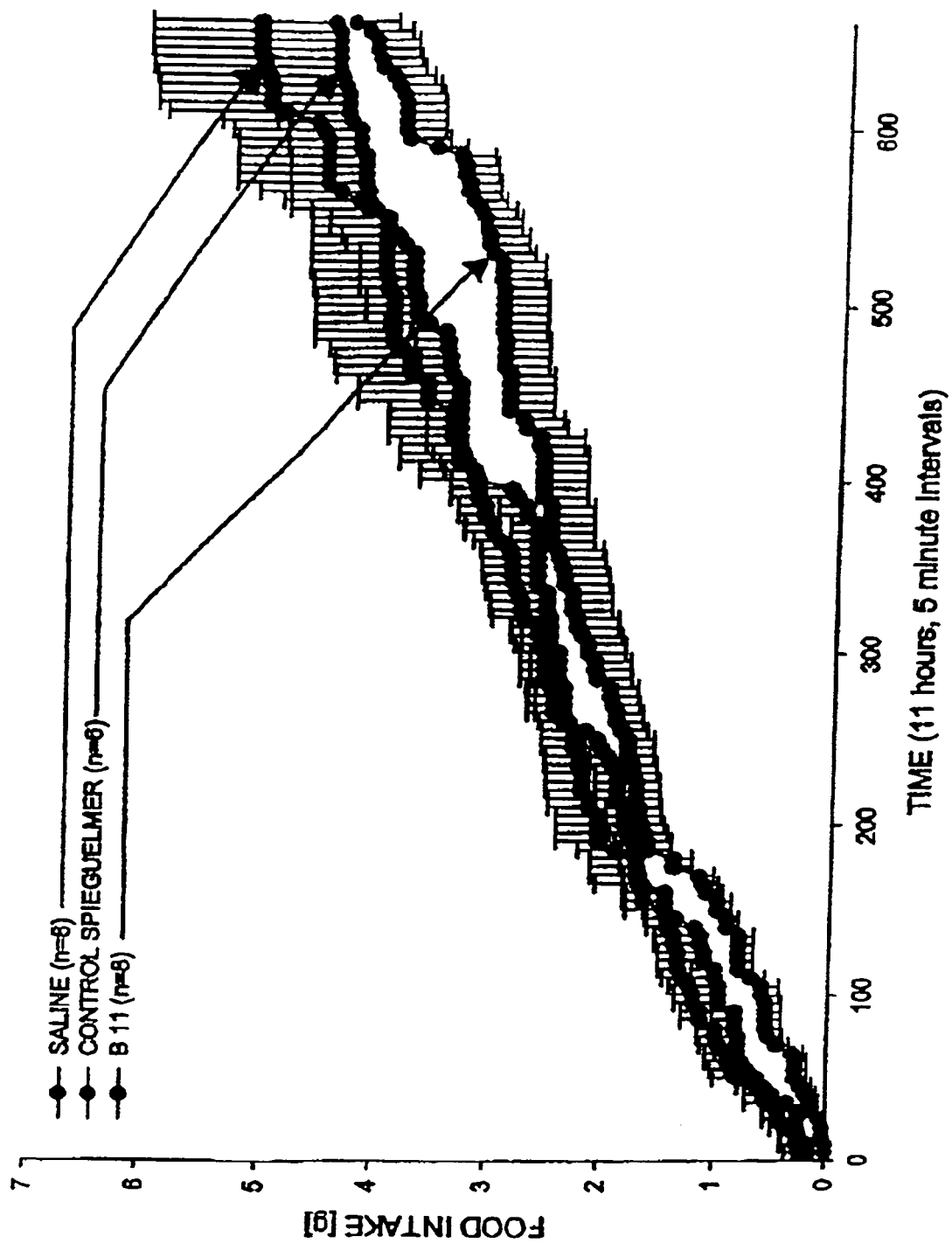

In the first set a decrease in food intake was observed (FIGS. 36 A and 36 B) whereas in the second set no difference between the anti-Ghrelin and the control Spiegelmer can be seen (FIGS. 37 A and 37 B). In total a trend towards decrease in food intake in the time period following the administration of anti-Ghrelin Spiegelmer is indicated (FIGS. 38 A and 38 B).

EXAMPLE 9

Investigation of the Effect of i.v. Administered Anti-Ghrelin-Spiegelmer on Food Intake of Meal-Trained Mice Mice (NMRI) were trained to have access to food only twice during the dark phase for the period of 1 hour. Under these conditions they learn quickly to feed during that time to meet their dietary requirements. The rational for this approach is to achieve a better comparability between individual test animals and the groups in total.

The experiment was carried out with 3 groups of 8 animals each. The groups received either saline solution, a non-active control Spiegelmer, or the PEGylated B 11 Spiegelmer by i.v. injection at the end of the light phase. The Spiegelmers were applied at a dose of 60 mg/kg (1 µM/kg). The experiment with a total of 24 animals was split in two sets of 12 animals each and was carried out at two different days. The test animals were given access to food for the period of 1 hour at 1 and 7 hours after the administration. The amount of consumed food was determined manually after each feeding period. FIG. 39 shows the food intake of 12 animals in the first experiment and FIG. 40 summarize the second experiment. The total food intake of all animals per group is shown in FIG. 41.

Especially during the first feeding period the animals showed a trend towards a decrease in food consumption (FIGS. 39 A and 39 B). However, in total only a weak and transient effect of the anti-Ghrelin Spiegelmer on food consumption could be observed.

EXAMPLE 10

Investigation of the Effect of i.c.v. Administered Anti-Ghrelin-Spiegelmer on Food Intake of Cannulated Rats Male Wistar rats were housed in a light-controlled room (12-h light/12-h dark cycle) and allowed free access to standard rat food. 1-2 weeks prior to experiments male Wistar rats were prepared for intracerebroventricular injection. A stainless steel intracerebroventricular (icv) cannula was implanted under anesthesia in the skull of rats. The icv cannula placement was confirmed in all rats by introducing dye after the experiment. On treatment day 4 rats per group received a single icv administration of a) control Spiegelmer (0,7 mM/5 µl/rat) b) Spiegelmer B 11 (0,7 mM/5 µl/rat) or c) vehicle (0,9% saline/5 µl/rat) at the end of the light phase. Food intake was measured for 24 hours and compared with the day before injection (baseline recording) FIG. 42.

In this experiment the effect of the anti-Ghrelin Spiegelmer was not significantly different from the results observed in the control groups.

EXAMPLE 11

Inhibition of the Growth Hormone Release after Exogeneous Ghrelin Administration by Anti-Ghrelin-Spiegelmer The experiment was done with Sprague Dawley rats after 7 days of adaptation in three groups of 6 animals per group. Two groups received either a single i.v. injection of 150 nmol of PEGylated anti-Ghrelin Spiegelmer or PEGylated control Spiegelmer. 30 min after the Spiegelmer administration each rat received an intravenous injection of 3 nmol Ghrelin (250 μl). Blood samples were drawn under anesthesia before Ghrelin administration for baseline recording of the Growth hormone level and 5 min, 15 min, 30 min and 45 min after injection. The resulting plasma samples were analysed by a radioimmunassay system (Growth hormone, Rat, Biotrak Assay Kit, RPN2561, Amersham Biosciences Europe GmbH, Freiburg).

The GH release was inhibited with sustained suppression for the whole period of observation in the Spiegelmer-treated group (FIG. 43) demonstrating the in vivo activity of the anti-Ghrelin Spiegelmer in the model described.

Moreover, the inhibition of GH release was investigated by administering different doses of anti-ghrelin spiegelmer (FIG. 45). A single dose of 15 nmol suppressed the effect of ghrelin on GH release, whereas a dose of 3 nmol did not suffice.

EXAMPLE 12

Neutralisation of the Stimulation of Food Intake of Exogeneous Ghrelin by an Anti-Ghrelin Spiegelmer The study was split in two experiments with four groups of animals using thirty-two male Sprague Dawley rats in total.

After 7 days of adaptation, the animals were be randomly allocated to four groups of 8 animals each. The rats were housed individually and were maintained on a normal light-dark cycle. The animals had free access to food and water. Animals, feeding jars and water bottles were weighed (to the nearest 0,1 g) approximately 2 hours after the onset of the light period. The feeding jars and water bottles were weighed 4 hours later and food and water intakes of the different groups of rats were calculated.

In the first set the optimal dose of exogeneous Ghrelin was tested. Three different doses of Ghrelin (16,7 nmol/kg, 33,4 nmol/kg and 83,5 nmol/kg, respectively) were administered by the intraperitoneal route. Food and water intakes of the different dose groups were determined concurrently. Feeding jars and water bottles were weighted at the time of drug administration and after 1, 2 and 4 hours (FIG. 44). The optimal dose for the stimulation of food intake in rats after i.p. administration was 10 nmol/animal (FIG. 44)

In a subsequent experiment done according to the same protocol as described before the neutralisation of the effect of exogeneous Ghrelin on food intake by an anti-Ghrelin Spiegelmer was investigated. First Spiegelmer in two dose levels of 150 nmol/animal and 30 nmol/animal was administered s.c. One hour later rats received Ghrelin by i.p. administration. The control group received vehicle. Food and water intakes were monitored after 1, 2 and 4 hours as described above. The anti-Ghrelin Spiegelmer showed an effect on the food intake.

The features of the present invention disclosed in the specification, the sequence listing, the claims and/or the drawings may both separately and in any combination thereof be material for realizing the invention in various forms thereof.

The invention claimed is:

1. An antagonist of ghrelin, wherein the antagonist is a nucleic acid which specifically binds ghrelin, wherein said nucleic acid has the sequence of SEQ ID NO:8.

2. The antagonist according to claim 1, wherein the nucleic acid comprises at least one L-nucleotide.

3. The antagonist according to claim 1, wherein the antagonist is an L-nucleic acid.

4. The antagonist according to claim 1, wherein said ghrelin is L-ghrelin.

5. The nucleic acid of claim 4, wherein the nucleic acid is selected from the group consisting of DNA, RNA and combinations thereof.

6. A method for making the nucleic acid of claim 1, comprising the steps:
   a) generating a heterogeneous population of nucleic acids;
   b) contacting the population of step a) with a ghrelin;
   c) separating the nucleic acid(s) not interacting with the ghrelin to obtain the nucleic acid of claim 1;
   d) optionally separating the nucleic acid(s) interacting with the ghrelin; and
   e) optionally sequencing the nucleic acid(s) interacting with the ghrelin.

7. The method according to claim 6, further comprising amplification of the nucleic acid(s) interacting with the ghrelin.

8. The method according to claim 6 or 7, wherein steps b) to d) are repeated.

9. A method for making the L-nucleic acid of claim 3 comprising the following steps:
   a) generating a heterogeneous population of D-nucleic acids;
   b) contacting the population of step a) with D-ghrelin;
   c) separating the D-nucleic acid not interacting with D-ghrelin;
   d) sequencing the D-nucleic acid interacting with D-ghrelin; and e) synthesizing the L-nucleic acid sequence identical to the sequence of the D-nucleic acid obtained in step d) to obtain the nucleic acid of claim 3.

10. The method according to claim 9 further comprising amplifying the D-nucleic acid interacting with D-ghrelin.

11. The method according to claim 9 or 10, characterized in that steps b) to e) are repeated.

12. A method of treating a disorder requiring reducing ghrelin or GHSR1a function, comprising the step of administering to a patient in need of treatment the antagonist of claim 1.

13. The method of claim 12 wherein the disorder is selected from the group consisting of obesity; improper regulation of energy balance; improper appetite or body weight; eating disorders; diabetes; improper glucose metabolism; tumour; improper blood pressure and cardiovascular disease.

14. A composition comprising the antagonist of claim 1, and a pharmaceutical acceptable carrier.

15. A complex comprising ghrelin and the nucleic acid of claim 1.

16. A method for screening for a ghrelin antagonist comprising the steps:
  a) providing a candidate ghrelin antagonist,
  b) providing the antagonist according to claim 1,
  c) providing a test system providing a signal in the presence of a ghrelin antagonist, wherein a reagent is labeled, and
  d) determining whether the candidate ghrelin antagonist is a ghrelin antagonist.

17. A kit comprising the antagonist of claim 1.

18. The complex of claim 15, wherein said complex is crystalline.

* * * * *